US012569174B2

(12) United States Patent
Hatamian

(10) Patent No.: US 12,569,174 B2
(45) Date of Patent: *Mar. 10, 2026

(54) ADJUSTABLE LANCET AND TEST CARTRIDGE FOR AUTOMATED MEDICAL SAMPLE COLLECTION AND TESTING

(71) Applicant: 2Pi-Sigma Corp., Newport Beach, CA (US)

(72) Inventor: Mehdi Hatamian, Mission Viejo, CA (US)

(73) Assignee: 2Pi-Sigma Corp., Newport Beach, CA (US)

( * ) Notice: Subject to any disclaimer, the term of this patent is extended or adjusted under 35 U.S.C. 154(b) by 812 days.

This patent is subject to a terminal disclaimer.

(21) Appl. No.: 17/864,364

(22) Filed: Jul. 13, 2022

(65) Prior Publication Data

US 2022/0346680 A1     Nov. 3, 2022

Related U.S. Application Data

(63) Continuation of application No. 17/548,514, filed on Dec. 11, 2021, now Pat. No. 11,389,097, which is a (Continued)

(51) Int. Cl.
*A61B 5/15*          (2006.01)
(52) U.S. Cl.
CPC ...... *A61B 5/150167* (2013.01); *A61B 5/1411* (2013.01); *A61B 5/1444* (2013.01); *A61B 5/150358* (2013.01); *A61B 5/150412* (2013.01)
(58) Field of Classification Search
None
See application file for complete search history.

(56) References Cited

U.S. PATENT DOCUMENTS 3,626,929 A  *  12/1971  Sanz ................ A61B 5/150022
                                                                600/583
4,031,399 A       6/1977  Klein et al.
                        (Continued)

FOREIGN PATENT DOCUMENTS

WO     WO 2011/029794      3/2011
WO     WO 2016/025843      2/2016
WO     WO 2018/195544     10/2018

OTHER PUBLICATIONS

U.S. Appl. No. 17/882,585, filed Aug. 7, 2022, Hatamian, Mehdi.
(Continued)

*Primary Examiner* — Matthew D Krcha
(74) *Attorney, Agent, or Firm* — Makoui Law, PC Ali Makoui

(57)                    ABSTRACT

A test cartridge includes an adjustable lancet. The adjustable lancet is controlled by a controller. The adjustable lancet automatically detects a subject's finger, adjusts the lancet's height, pricks the finger to draw blood, moves a tube to collect the blood, moves the tube away from the finger, and empties the blood from the tube into a vial or receptacle. The adjustable lancet may include safety features to prevent the lancet to trigger when the subject's fingernail is facing the lancet, to control the amount that the lancet pierces the subject's finger, and/or to prevent the reuse of a test cartridge for multiple persons or multiple times by the same person. The adjustable lancet may include a massager wheel and/or a pressure bar to rub the subject's finger after the finger is pierced to facilitate drawing of the blood from the finger.

20 Claims, 31 Drawing Sheets

Related U.S. Application Data continuation of application No. 16/663,711, filed on Oct. 25, 2019, now Pat. No. 11,202,593, which is a continuation-in-part of application No. 15/959,555, filed on Apr. 23, 2018, now Pat. No. 11,103,163, which is a continuation-in-part of application No. 15/954,442, filed on Apr. 16, 2018, now Pat. No. 10,791,972, which is a continuation-in-part of application No. 15/785,755, filed on Oct. 17, 2017, now Pat. No. 10,928,411.

(60) Provisional application No. 62/488,174, filed on Apr. 21, 2017.

(56) References Cited

U.S. PATENT DOCUMENTS

| | | | |
|---|---|---|---|
| 5,405,510 A | 4/1995 | Betts et al. | |
| 5,502,651 A | 3/1996 | Jackson et al. | |
| 5,662,127 A | 9/1997 | De Vaughn | |
| 5,916,230 A | 6/1999 | Brenneman et al. | |
| 5,971,941 A | 10/1999 | Simons et al. | |
| 6,506,165 B1 | 1/2003 | Sweeney | |
| 6,506,168 B1 | 1/2003 | Fathallah et al. | |
| 6,770,190 B1 | 8/2004 | Milanovski et al. | |
| 7,374,949 B2 | 5/2008 | Kuriger | |
| 8,413,886 B2 | 4/2013 | Creaven et al. | |
| 10,791,972 B2 | 10/2020 | Hatamian | |
| 10,816,545 B2 | 10/2020 | Hatamian | |
| 10,928,411 B2 | 2/2021 | Hatamian | |
| 11,103,163 B2 | 8/2021 | Hatamian et al. | |
| 11,175,303 B2 | 11/2021 | Hatamian | |
| 11,202,593 B2 | 12/2021 | Hatamian | |
| 11,389,097 B2 | 7/2022 | Hatamian | |
| 2002/0022789 A1* | 2/2002 | Perez | A61B 5/15117 |
| | | | 600/573 |
| 2003/0067599 A1 | 4/2003 | Carrillo | |
| 2003/0083685 A1 | 5/2003 | Freeman et al. | |
| 2003/0088191 A1 | 5/2003 | Freeman et al. | |
| 2003/0136183 A1 | 7/2003 | Neal et al. | |
| 2004/0092995 A1 | 5/2004 | Boecker et al. | |
| 2004/0173456 A1 | 9/2004 | Boos et al. | |
| 2005/0032204 A1 | 2/2005 | Rodgers et al. | |
| 2005/0101981 A1 | 5/2005 | Alden et al. | |
| 2005/0130292 A1 | 6/2005 | Ahn et al. | |
| 2005/0208648 A1 | 9/2005 | Sage et al. | |
| 2006/0068490 A1 | 3/2006 | Tang et al. | |
| 2007/0276290 A1* | 11/2007 | Boecker | A61B 5/150068 |
| | | | 600/583 |
| 2008/0077048 A1 | 3/2008 | Escutia et al. | |
| 2008/0082117 A1 | 4/2008 | Ruf | |
| 2008/0194987 A1 | 8/2008 | Boecker | |
| 2008/0194988 A1 | 8/2008 | Nakamura et al. | |
| 2008/0297169 A1 | 12/2008 | Greenquist et al. | |
| 2009/0269837 A1 | 10/2009 | Shevkoplyas et al. | |
| 2009/0298097 A1 | 12/2009 | Harris et al. | |
| 2010/0045267 A1 | 2/2010 | Dittmer et al. | |
| 2010/0174211 A1 | 7/2010 | Frey et al. | |
| 2010/0196207 A1 | 8/2010 | Steinmiller et al. | |
| 2011/0053289 A1 | 3/2011 | Lowe et al. | |
| 2011/0137208 A1 | 6/2011 | Valk et al. | |
| 2011/0201312 A1 | 8/2011 | Peterson et al. | |
| 2012/0208283 A1 | 8/2012 | Gheorghiu et al. | |
| 2012/0301967 A1 | 11/2012 | Nadkarni | |
| 2013/0114075 A1 | 5/2013 | Hukari et al. | |
| 2013/0158432 A1 | 6/2013 | Escutia et al. | |
| 2013/0309778 A1 | 11/2013 | Lowe et al. | |
| 2014/0295433 A1 | 10/2014 | Chen et al. | |
| 2014/0378800 A1 | 12/2014 | Richter et al. | |
| 2015/0377814 A1 | 12/2015 | Schindelholz et al. | |
| 2017/0016753 A1 | 1/2017 | Shi et al. | |
| 2022/0065889 A1 | 3/2022 | Hatamian | |

OTHER PUBLICATIONS

Portions of prosecution history of U.S. Appl. No. 15/785,755, filed Feb. 3, 2021, Hatamian, Mehdi.

Portions of prosecution history of U.S. Appl. No. 15/954,442, filed Sep. 16, 2020, Hatamian, Mehdi.

Portions of prosecution history of U.S. Appl. No. 15/959,555, filed Aug. 11, 2021, Hatamian, Mehdi.

Portions of prosecution history of U.S. Appl. No. 15/959,576, filed Oct. 7, 2020, Hatamian, Mehdi.

Portions of prosecution history of U.S. Appl. No. 16/664,746, filed Oct. 27, 2021, Hatamian, Mehdi.

Portions of prosecution history of U.S. Appl. No. 16/663,711, filed Dec. 1, 2021, Hatamian, Mehdi.

Portions of prosecution history of U.S. Appl. No. 17/521,853, filed Aug. 17, 2022, Hatamian, Mehdi.

Portions of prosecution history of U.S. Appl. No. 17/548,514, filed Jun. 29, 2022, Hatamian, Mehdi.

International Written Opinion of PCT/US18/28913, May 10, 2018 (mailing date), 2PI-SIGMA CORP.

International Search Report of PCT/US18/28913, May 10, 2018 (mailing date), 2PI-SIGMA CORP.

International Preliminary Search Report of PCT/US18/28913, Oct. 22, 2019 (mailing date), 2PI-SIGMA CORP.

* cited by examiner

100

100

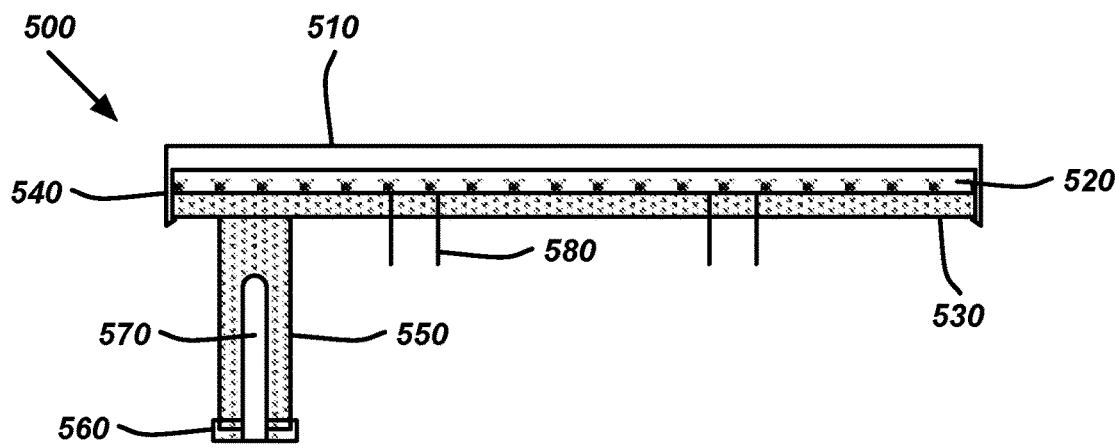
FIG. 5
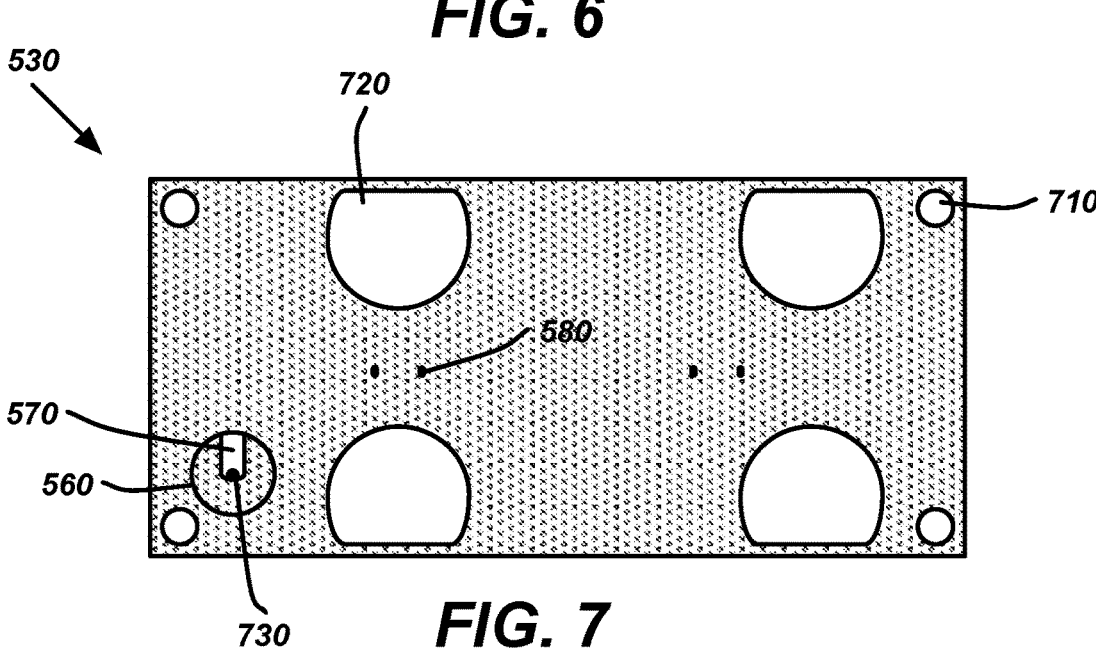
FIG. 6
FIG. 7

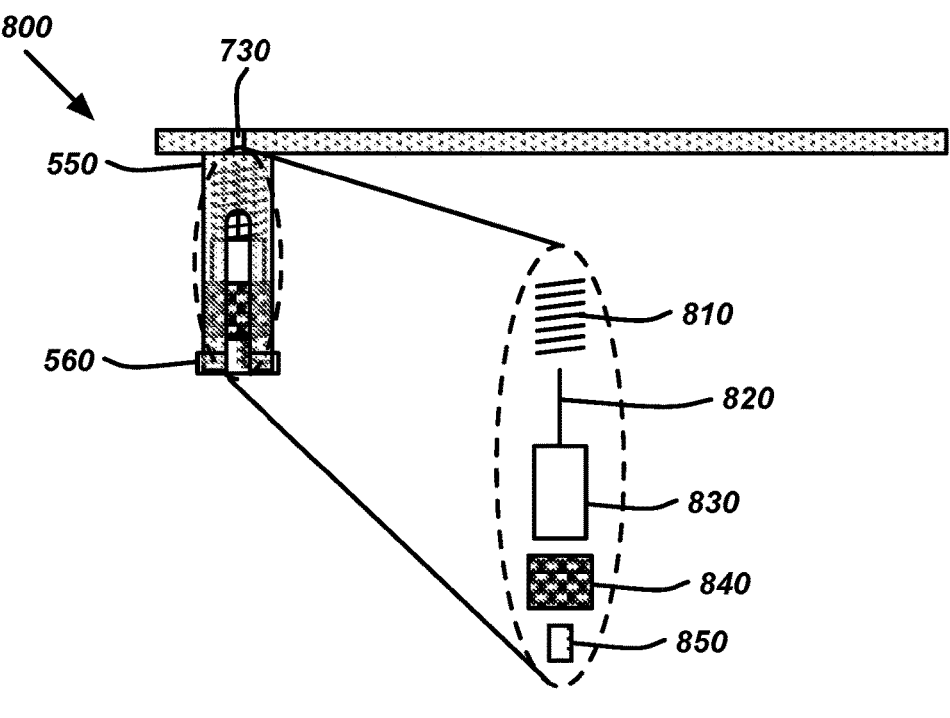
FIG. 8
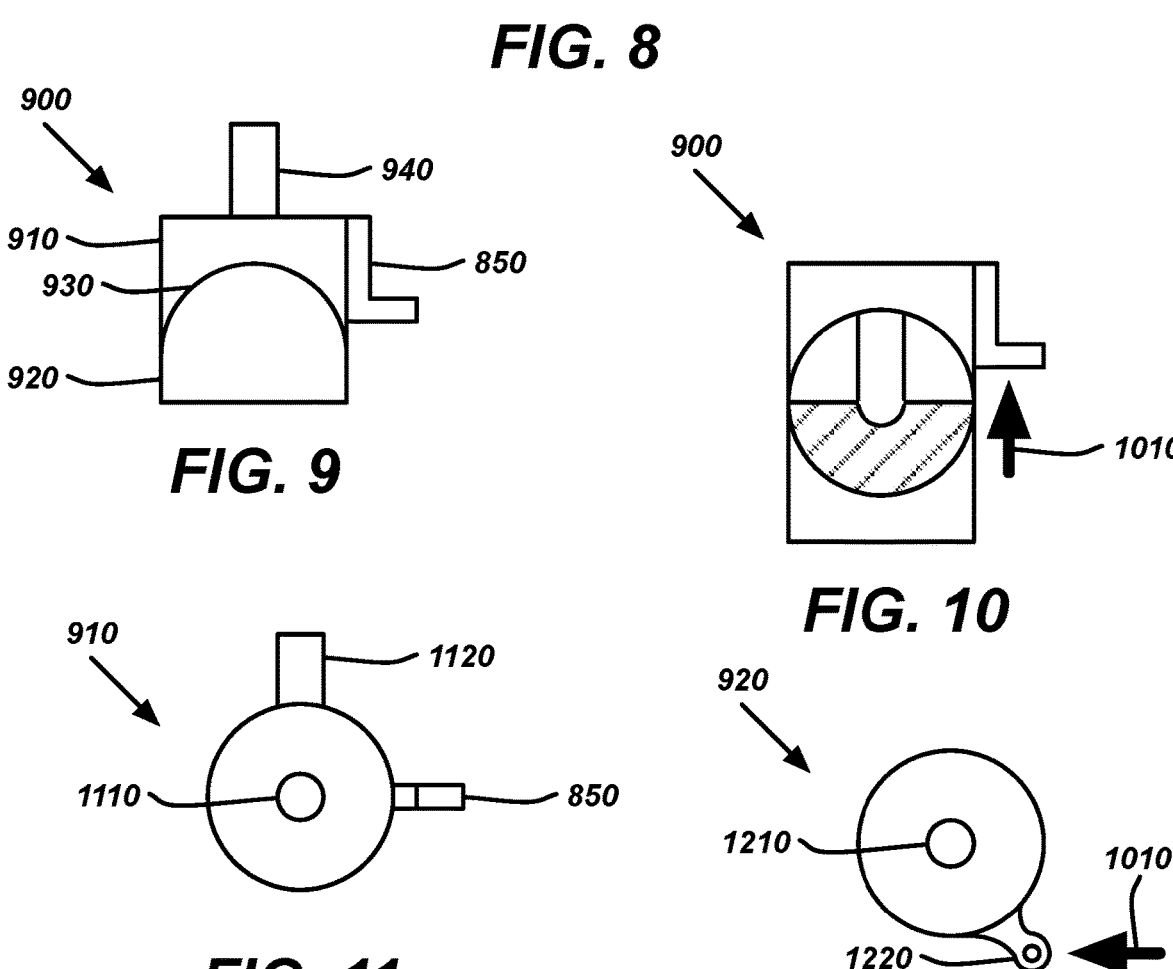
FIG. 9
FIG. 10
FIG. 11
FIG. 12

1300

*110*

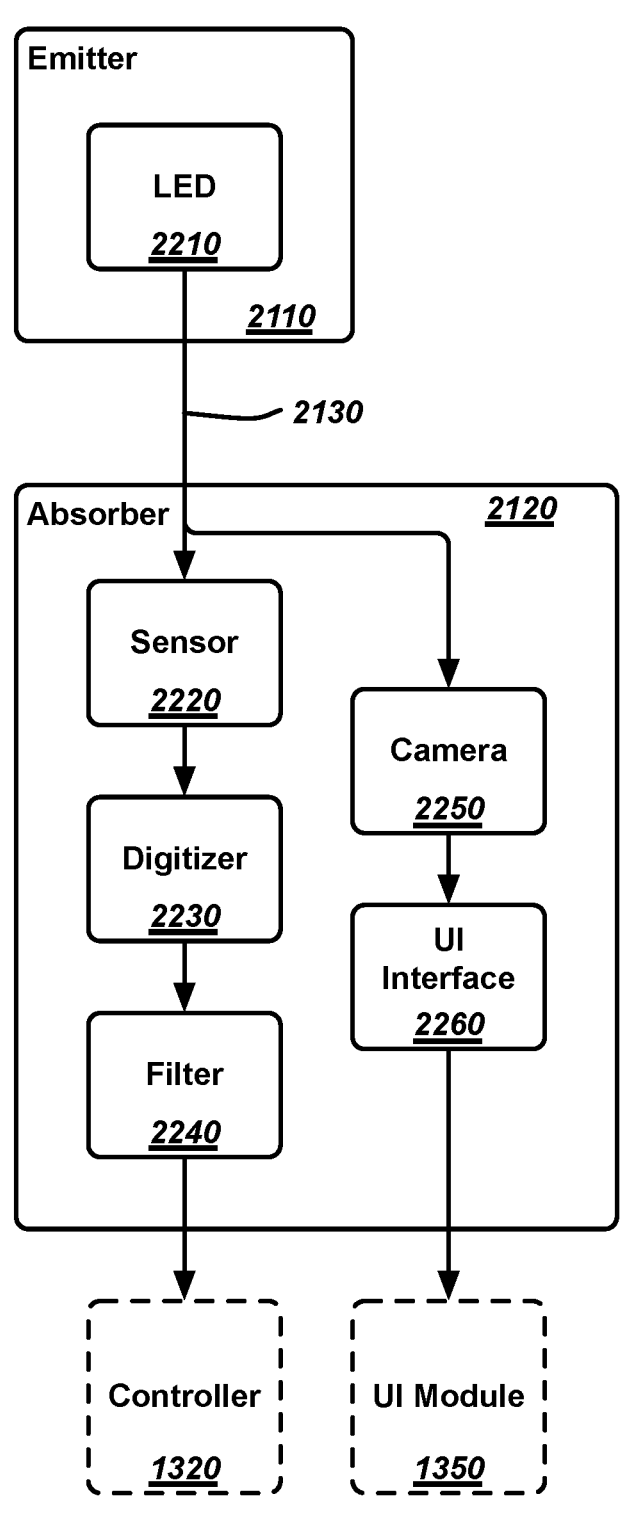
FIG. 22

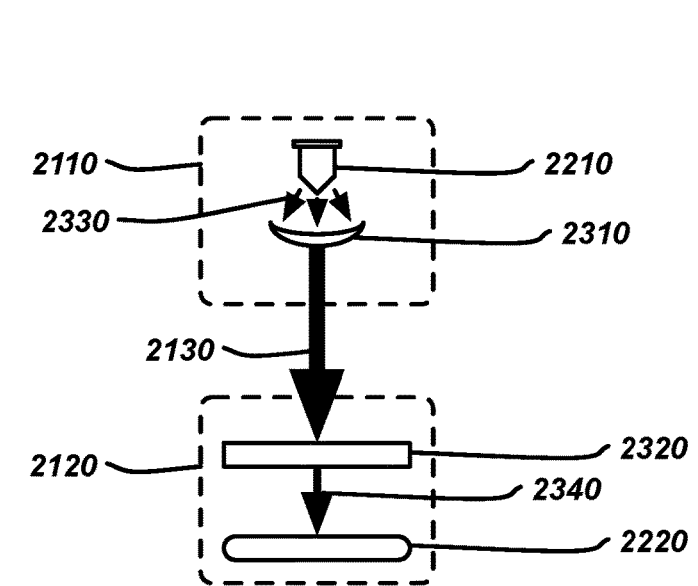
FIG. 23
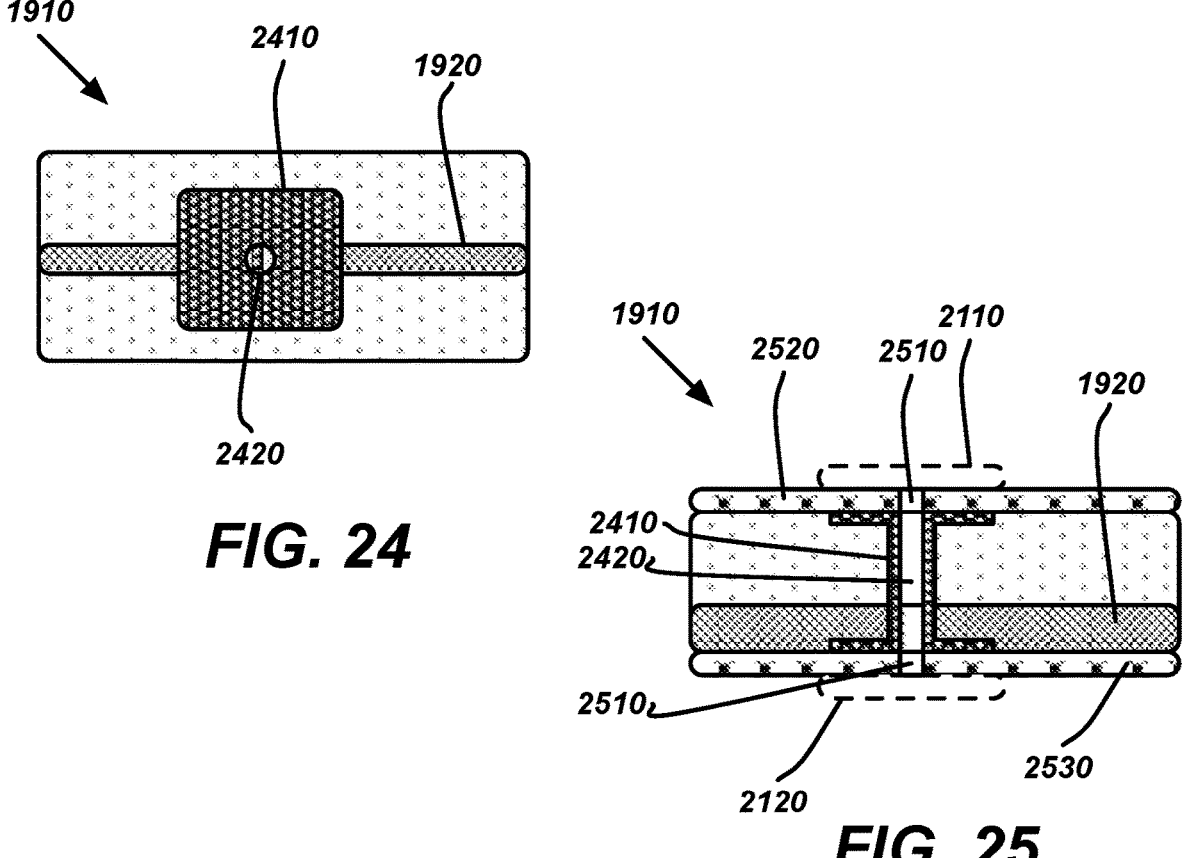
FIG. 24
FIG. 25

2600

2800

```
                        ┌─────────────┐
                        │    Begin    │
                        └──────┬──────┘
                               │
                        ┌──────▼──────────────┐
                        │ Retrieve sample     │────── 2810
                        │ parameters          │
                        └──────┬──────────────┘
                               │
                        ┌──────▼──────────────┐
                        │   Activate pump     │────── 2820
                        └──────┬──────────────┘
                               │
              ┌───────▶┌──────▼──────────────┐
              │        │ Monitor balloon     │────── 2830
              │        │ pressure            │
              │        └──────┬──────────────┘
              │               │
         No   │        ◇──────▼──────◇
              └────────│ Specified pressure │────── 2840
                       │   reached?          │
                       ◇──────┬──────◇
                              │ Yes
                       ┌──────▼──────────────┐
                       │   Extend actuator   │────── 2850
                       └──────┬──────────────┘
                              │
                       ┌──────▼──────────────┐
                       │   Retract actuator  │────── 2860
                       └──────┬──────────────┘
                              │
         No   ┌───────◇──────▼──────◇
              └───────│  Sample complete?   │────── 2870
                      ◇──────┬──────◇
                             │ Yes
                      ┌──────▼──────────────┐
                      │ Deactivate rubber   │────── 2880
                      │ pump                │
                      └──────┬──────────────┘
                             │
                      ┌──────▼──────┐
                      │     End     │
                      └─────────────┘
```

```
                    ┌─────────┐
                    │  Begin  │
                    └────┬────┘
                         │
                         ▼
        ┌────────────────────────────────┐
        │     Retrieve sample volume     │──── 3010
        └────────────────┬───────────────┘
                         │
                         ▼
        ┌────────────────────────────────┐
        │         Activate pump          │──── 3020
        └────────────────┬───────────────┘
                         │
    ┌─────────┐          ▼
    │         │      ╱────────╲
    │    No   │◄────╱ Fluid    ╲──── 3030
    │         │     ╲ detected? ╱
    └─────────┘      ╲────────╱
                         │ Yes
                         ▼
    ┌──►┌────────────────────────────────┐
    │   │          Run counter           │──── 3040
    │   └────────────────┬───────────────┘
    │                    │
    │    ┌─────┐         ▼
    │    │ No  │     ╱────────╲
    └────┤     │◄───╱  Sample   ╲──── 3050
         └─────┘    ╲ complete? ╱
                     ╲────────╱
                         │ Yes
                         ▼
        ┌────────────────────────────────┐
        │          Stop counter          │──── 3060
        └────────────────┬───────────────┘
                         │
                         ▼
        ┌────────────────────────────────┐
        │        Calculate volume        │──── 3070
        └────────────────┬───────────────┘
                         │
                         ▼
        ┌────────────────────────────────┐
        │     Send fulfillment message   │──── 3080
        └────────────────┬───────────────┘
                         │
                         ▼
                    ┌─────────┐
                    │   End   │
                    └─────────┘
```

Begin

Collect sample ⟶ *4110*

Add buffer solution ⟶ *4120*

Mix with antibodies ⟶ *4130*

Mix with magnetic solution ⟶ *4140*

Activate magnet ⟶ *4150*

Pump non-magnetic portion to first measurement cavity ⟶ *4160*

Deactivate magnet ⟶ *4170*

Measure charge difference ⟶ *4180*

End

ADJUSTABLE LANCET AND TEST CARTRIDGE FOR AUTOMATED MEDICAL SAMPLE COLLECTION AND TESTING

CROSS-REFERENCE TO RELATED APPLICATIONS

This application is a continuation application of U.S. patent application Ser. No. 17/548,514, filed on Dec. 11, 2021, published as U.S. Patent Publication 2022/0095971. U.S. patent application Ser. No. 17/548,514 is a continuation application of U.S. patent application Ser. No. 16/663,711, filed on Oct. 25, 2019, issued as U.S. Pat. No. 11,202,593. U.S. patent application Ser. No. 16/663,711 is a continuation-in-part of U.S. patent application Ser. No. 15/959,555, filed Apr. 23, 2018, issued as U.S. Pat. No. 11,103,163. U.S. patent application Ser. No. 15/959,555 is a continuation-in-part of U.S. patent application Ser. No. 15/954,442, filed on Apr. 16, 2018, issued as U.S. Pat. No. 10,791,972. U.S. patent application Ser. No. 15/954,442 is a continuation-in-part of U.S. patent application Ser. No. 15/785,755, filed on Oct. 17, 2017, issued as U.S. Pat. No. 10,928,411. U.S. patent application Ser. No. 15/785,755 claims priority to U.S. Provisional Patent Application Ser. No. 62/488,174, filed on Apr. 21, 2017. The contents of U.S. patent application Ser. No. 17/548,514, published as U.S. Patent Publication 2022/0095971, U.S. patent application Ser. No. 16/663,711 issued as U.S. Pat. No. 11,202,593 and U.S. patent application Ser. No. 15/959,555, issued as U.S. Pat. No. 11,103,163, are hereby incorporated by reference.

BACKGROUND

Many users, whether professional or home-based, may wish to take blood samples (and/or other fluid samples) on a regular basis. For instance, people with type I diabetes may need to measure blood sugar at least four times per day.

Existing sampling methods require users to manually prick a fingertip to generate and collect a sample for testing. Such sampling results in inconsistent sample quantities, stress and anxiety for the subject, potential for sample contamination, and/or other issues related to manual collection and processing. In addition, even current lancing devices require a user to manually align the device and lancet. A user also has to manually specify desired device parameters, such as extension force.

Furthermore, after generating a sample, a subject may need to perform additional operations such as collecting the sample, applying the sample to a test strip, inserting the strip into a testing device, etc.

In addition, as collection may be performed frequently, subjects may wish to collect the minimum sample needed for testing.

When conducting trials or otherwise collecting samples, current solutions require a significant time commitment for each subject (e.g., fifteen minutes or to draw a sample, perform a test, collect measurements, etc.).

Thus there is a need for a way to automatically and quickly generate and collect a sample for testing with accurate and controllable lancet alignment and extension.

SUMMARY

A sample collection and testing device (SCTD) of some embodiments may be able to collect a sample from a test subject. The SCTD may utilize removable cartridges. Such cartridges (or portions thereof) may be intended for single use.

Some embodiments are able to automatically collect a blood sample from a subject's finger. Such sample collection may involve detection of the subject (or finger in this example), piercing or pricking of the subject, collection, and/or storage of the sample. Although blood is used as one example, various other fluids may be collected and/or analyzed.

The sample may be collected via a receptacle (e.g., a recess in a surface of the cartridge) using a pump, valve, fluid sensing chip, tubing or other flow pathways, storage cavities, and/or other appropriate features.

A piercing element of some embodiments may include a needle and spring, actuator, and/or other appropriate elements. The piercing element may be automatically extended an appropriate amount to draw blood through the skin in this example. The amount of extension may be specified and/or limited in various appropriate ways (e.g., physical or mechanical barriers or stops, a value associated with the actuator extension, etc.). The extension may be set by a user, may be based on default values, or may be determined automatically using various sensors associated with the SCTD and/or cartridge.

A disposable cartridge of some embodiments may include a top plate, a microfluidic chip, a bottom plate, and a removable top cover. The top cover may be removed to provide access to the cartridge (e.g., collection points) and replaced to secure the contents for disposal. The bottom plate may include a lancet assembly. The lancet assembly may include a spring, lancet, lancet cup, and actuator receptacle. The bottom plate may include a lancet guide.

In some embodiments, a fluid sensing device (and/or other elements of the cartridge) may include and/or be at least partially enclosed in a flexible material (e.g., silicone). Such enclosed elements may come into contact with the sample fluid and thus be intended to be single use or disposable. Other elements, such as the piercing element, that come into contact with the sample fluid may also be included in a disposable cartridge (or disposable portion thereof). Throughout the specification, any reference to "disposable" elements or components indicates single use components (e.g., components that will directly contact a blood sample).

Some embodiments may include non-contact sensing elements such that the fluid sensing device is able to be reused. Such non-contact elements may include, for instance, embedded sensors or leads that are able to be accessed via terminals along an outer surface of the cartridge. In some embodiments, the sensing elements may be able to sense properties of the sample through the enclosure without use of any exposed leads or contacts.

The non-contact elements may include fluid measurement features in some embodiments. The fluid measurement features may include optical measurement elements that are able to detect and measure properties associated with fluid samples. Such measurements may include, for example, volume, viscosity or flow rate, color density or saturation, etc.

One example cartridge may be able to perform a test for cancer using human aspartyl (asparaginyl) β-hydroxylase (HAAH) protein and its associated antibodies. Such a cartridge may utilize magnetic beads and charge detection to evaluate samples.

Some embodiments of the SCTD (and/or associated cartridges) may be able to measure small amounts of fluid using optical components such as lasers, light-emitting diode (LED) lights sources, and/or other optical components to detect fluid within a transparent or semitransparent fluid pathway.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The exemplary features of the disclosure are set forth in the appended claims. However, for purpose of explanation, several embodiments are illustrated in the following drawings.

FIG. 5 illustrates a side elevation view of an exemplary embodiment of a cartridge used by the sample collection and testing device of FIG. 1;

FIG. 6 illustrates a top plan view of the exemplary cartridge of FIG. 5;

FIG. 7 illustrates a bottom plan view of the exemplary cartridge of FIG. 5;

FIG. 8 illustrates a side elevation view of the exemplary cartridge of FIG. 5, including an exploded view of an exemplary lancet;

FIG. 9 illustrates a side elevation view of an exemplary embodiment of a lancet actuator included in the sample collection and testing device of FIG. 1;

FIG. 10 illustrates a side elevation view of the lancet actuator of FIG. 9 in an extended position;

FIG. 11 illustrates a top plan view of the lancet actuator of FIG. 9;

FIG. 12 illustrates a bottom plan view of the lancet actuator of FIG. 9;

FIG. 22 illustrates a schematic block diagram of an optical measurement element according to an exemplary embodiment;

FIG. 23 illustrates a schematic block diagram of various optical processing components associated with an optical measurement element in some embodiments;

FIG. 24 illustrates a top plan view of a portion of a cartridge associated with an optical measurement element in some embodiments;

FIG. 25 illustrates a side elevation view of a portion of a cartridge associated with an optical measurement element in some embodiments;

FIG. 28 illustrates a flow chart of an exemplary process that controls a sampling element of the automated sample collection and testing device of FIG. 1;

FIG. 30 illustrates a flow chart of an exemplary process that impels a small amount of fluid within the exemplary embodiments of the sample processing module included in the sample collection and testing device of FIG. 1;

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide an automated sample collection and testing device (SCTD).

Some embodiments may include lancet assemblies that allow automatic sample generation (e.g., finger pricking) and collection. Such lancet assemblies may include a spring, lancet, actuator, various guides, etc.

A first exemplary embodiment provides a disposable lancet assembly comprising: a spring aligned along a linear axis; a lancet aligned along the linear axis adjacent to the spring; a needle cup aligned along the linear axis adjacent to the lancet; and a housing comprising a channel that accepts an actuator interface such that the needle cup and lancet are able to be moved along the linear axis via the actuator interface.

A second exemplary embodiment provides a medical test cartridge comprising: a bottom plate; a microfluidic chip; and a top plate, wherein the top plate is coupled to the bottom plate such that the microfluidic chip is retained between the top plate and the bottom plate.

A third exemplary embodiment provides a sample collection and testing device comprising: a lancet assembly; a lancet actuator coupled to the lancet assembly; and a microfluidic test chip.

Several more detailed embodiments are described in the sections below. Section I provides a description of hardware architectures of some embodiments. Section II then describes various methods of operation of some embodiments. Lastly, Section III describes a computer system which implements some of the embodiments.

I. Hardware Architecture

Figure 1:
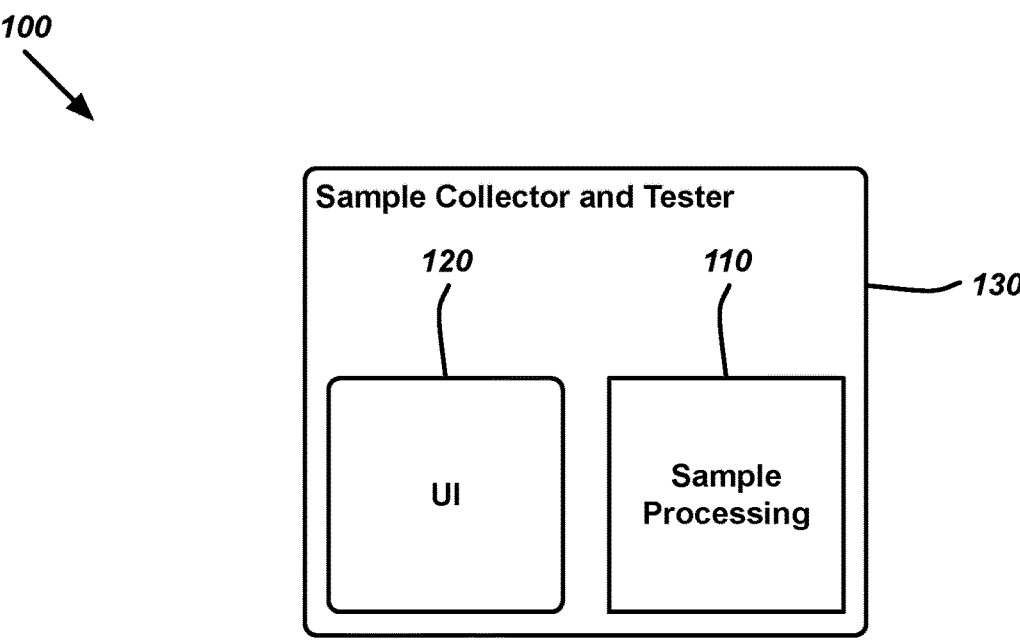
FIG. 1 illustrates a top view of an automated sample collection and testing device according to an exemplary embodiment.

FIG. 1 illustrates a top view of an automated SCTD 100 according to an exemplary embodiment. As shown, the device may include a removable test sample processing module 110, various user interface (UI) features 120, such as buttons, displays, touchscreens, keypads, LEDs, etc., and a housing 130.

The sample processing module 110 will be described in more detail in reference to FIG. 2 below. The housing 130 may be able to sit flat on a surface such as a tabletop or counter. The housing may include receptacles, sockets, etc. that may allow the housing to be attached to various elements, as appropriate (e.g., stands, carts, etc.). The housing may include various mechanical features (e.g., a cartridge release lever and associated mechanism, a hinged lid or door that provides access to elements within the housing, etc.).

Figure 2:
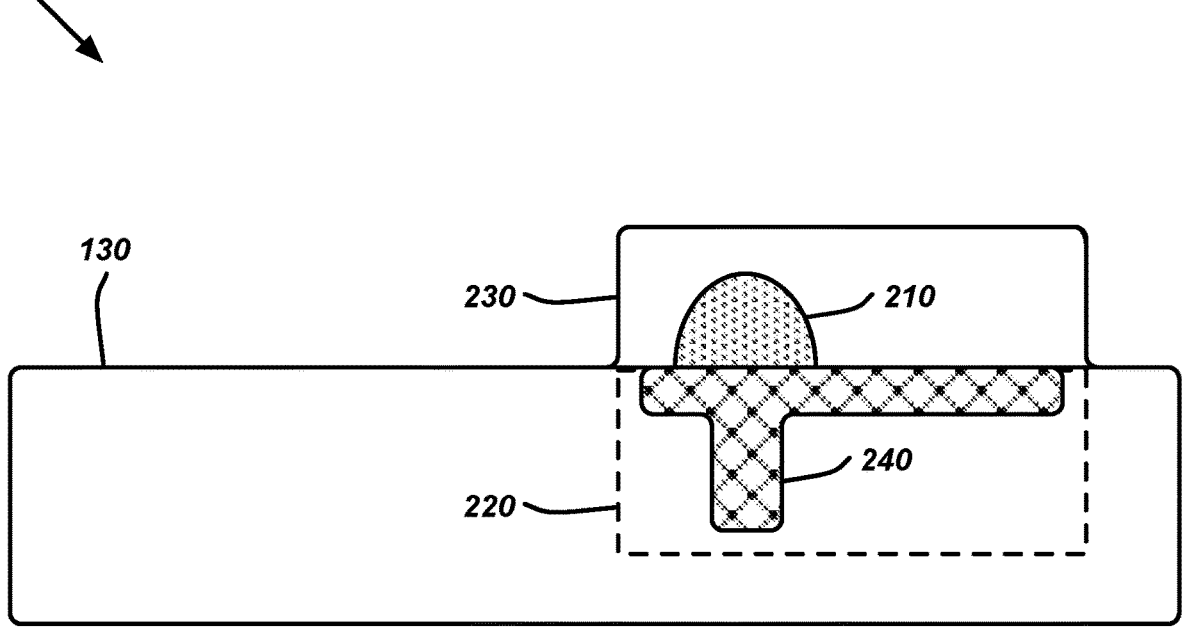
FIG. 2 illustrates a front elevation view of the automated sample collection and testing device of FIG. 1.

FIG. 2 illustrates a front elevation view of the automated sample collection and testing device 100. As shown, the sample processing module 110 of this example includes a receptacle 210 sized and shaped appropriately for a human finger, a bottom portion 220, a top portion 230, and a disposable cartridge 240 (or cavity if no cartridge has been inserted) that is able to be added to or removed from the sample processing module 110. In this example, the top portion 230 may include a hinge such that the top portion may be pulled away from the bottom portion to expose the cartridge 240 (or cavity).

Figure 3:
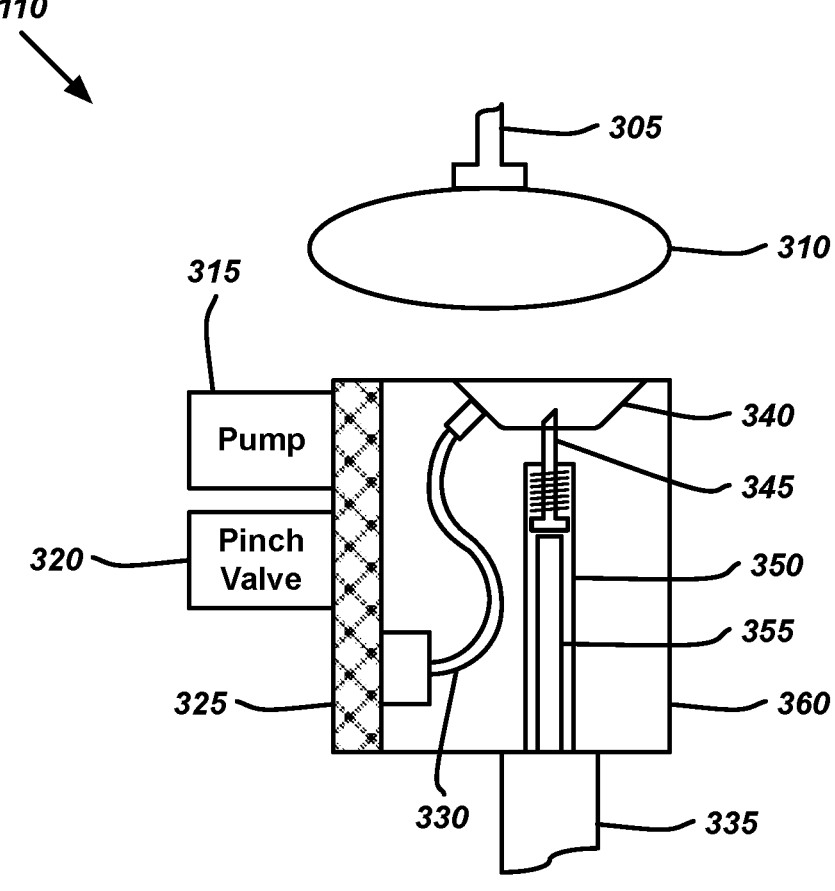
FIG. 3 illustrates a side elevation view of an exemplary embodiment of a sample processing module included in the sample collection and testing device of FIG. 1.

FIG. 3 illustrates a side elevation view of an exemplary embodiment of the sample processing module 110, showing various internal components of the cartridge. As shown, the cartridge may include a rubber pump 305, retention element 310, sample pump 315, pinch valve 320, chip 325, tubing or other connectors 330, an actuator 335, a receptacle 340, needle and spring 345, needle housing 350, needle connector 355, and cartridge housing 360.

In this example, elements 325-330 and 340-360 may typically be included in the disposable cartridge portion 240 of the sample processing module 110, while the other components may be included in a reusable portion of the sample processing module 110 or otherwise included in the SCTD 100.

The rubber pump 305 may be a device capable of pumping fluid (e.g., air) into the retention element 310. The fluid may be in a liquid and/or gaseous form. The retention element 310 may be a balloon or flexible bladder that is able to accept an appropriate amount of fluid and, in turn, provide adjustable resistance to pressure. In some embodiments, the balloon may be coupled to a door of the housing, where the door may be opened, an appendage inserted, and the door closed. Such a door may include an electromagnetic latch.

The sample pump 315 may be a pump capable of moving fluid along a pathway. In some embodiments, the sample pump may be associated with a measurement element or meter (not shown) that is able to determine an amount of fluid moved by the pump. The pinch valve 320 may be a controllable valve capable of permitting or restraining fluid flow within the sample processing module 110.

The "chip" 325 or fluid sensing plate may be able to store and/or interact with various fluids (e.g., sample fluids, reactants, catalysts, etc.). The chip may include electronic circuitry (e.g., sensors, integrated circuits, etc.) that may be able to detect or measure attributes of the fluid(s) and generate signals that provide the measured attributes to other components (e.g., a processor).

Some embodiments may include a fluid sensing plate that is reusable across multiple samples. Such a plate may either contact a sample indirectly (e.g., using disposable probes that are part of the cartridge and are able to provide electrical connection via some external connectors to the device 100). In some embodiments, the plate may be completely non-contact and sense fluid attributes through a silicone membrane or other appropriate cartridge material.

The tubing or other connectors 330 may allow fluid flow among the elements of the sample processing module 110. In some embodiments, the tubing 330 may be formed by cavities within a solid element. For instance, in some embodiments, the chip 325, tubing 330, and receptacle 340 may be included in cube-shaped silicone.

The actuator 335 may be able to apply force to the connector 355. The actuator 335 may be able to extend and retract the connector 355. The actuator 335 may include components such as a linear solenoid, a rotary motor, etc. In some embodiments, the actuator may be controllable such that attributes such as depth or height, pressure, velocity, acceleration, torque, etc. may be able to be controlled based on various parameters (e.g., default values, user selections, measured values, etc.).

The receptacle 340 may include a recess or tub appropriate for placement of a finger in this example. Different embodiments may include different receptacles. For instance, some embodiments may include a connector that allows vials or other containers (e.g., micro tubes or other industry standard micro containers) to be coupled to the sample processing module 110. In some embodiments, the fluid may be collected and tested at the receptacle 340. For instance, a droplet of blood from a fingertip may be applied to a paper test strip located at the receptacle. In some embodiments, a micro tube or other container may be removed (after a sample has been collected) and sent elsewhere for testing (or attached to another testing device).

The extendable and retractable needle and spring 345 (or other piercing element such as a blade) may be able to extend out into the receptacle 340 such that a sample may be taken. The spring may cause the needle 345 to automatically retract when pressure is released from the actuator 335. The height and/or other attributes of the needle 345 may be adjusted manually or electronically (e.g., using actuators). For instance, some embodiments may include a physical knob that may allow users to adjust the height of housing 350, thereby controlling the maximum extension of the needle 345.

As another example, some embodiments may allow a desired height or extension of the needle 345 to be entered using a UI element or external device. Such desired height may be set in relative (e.g., discrete values from one to ten) or absolute terms (e.g., height in millimeters). The desired height may be used to control the operation of the actuator 335 to control the extension of the needle 345. Some embodiments may include various sensors that may automatically determine a desired height and apply such determined height to the operation of the needle 345. Such adjustment parameters may be stored such that a user may collect additional samples once comfortable needle use has been achieved.

The needle housing 350 may be a rigid hollow column. In this example, the housing is associated with a round needle and spring 345 and a cylindrical connector 355. Different embodiments may have elements with different shapes, based on the particular application.

The needle connector 355 may be a rigid member that couples the actuator 335 to the needle 345 such that the extension (or retraction) of the actuator 335 causes the needle 345 to be extended (or retracted).

The cartridge housing 360 in this example has a cube shape. The housing may include multiple portions. Some embodiments may include hinges, latches, etc. that may couple the portions. The housing may include various interfaces for use with the SCTD 100. Such interfaces may include, for instance, sockets or other connectors, terminals, wireless communication interfaces, etc.

During use, a subject's finger may be retained using the rubber pump 305 and balloon 310. The punching needle and associated spring 345 may be manipulated by the actuator 335 via the connector 355 to pierce the subject's finger and a blood sample may be collected using the chip 325, pinch valve 320, pump 315, and collection receptacle 340 under the finger. In addition, various tubes, connectors, etc. 330 may be utilized to transport fluid from the collection receptacle 340 to the chip 325.

The pressure of the balloon 310 (or other retaining element) may be adjustable. Such pressure may be set to retain the finger in place without causing a feeling that the finger is trapped or any other discomfort. Such a pressure adjustment may utilize various appropriate UI elements, including, for instance, up/down buttons, touchscreen features, received command from an external device, etc. Such adjustments may be stored for future use by a particular subject. The pressure may be determined (and/or controller) in various appropriate ways, such as measuring (and/or varying) pump current and/or using an electronic pressure sensor device.

In this example, the sample processing module 110 includes automated collection and processing. Some embodiments may be able to receive a cartridge that includes a previously collected sample (e.g., held in a microtube). Such embodiments may be able to pierce (and/or otherwise interact with) the microtube in order to retrieve and analyze the collected sample.

Some embodiments may include at least one flowmeter. Such a flowmeter may follow the collection point in order to monitor the flow of fluid and/or measure volume. Such elements may be omitted in some embodiments in order to reduce cost of the sample processing module 110 (or disposable portions thereof).

In some embodiments, the SCTD 100 may automatically detect the finger and activate the device. Some embodiments may include a manual control such as a button or touchscreen 120 that can be used to activate the device 100. Such a control may be received as a command message from an external user device.

Figure 4:
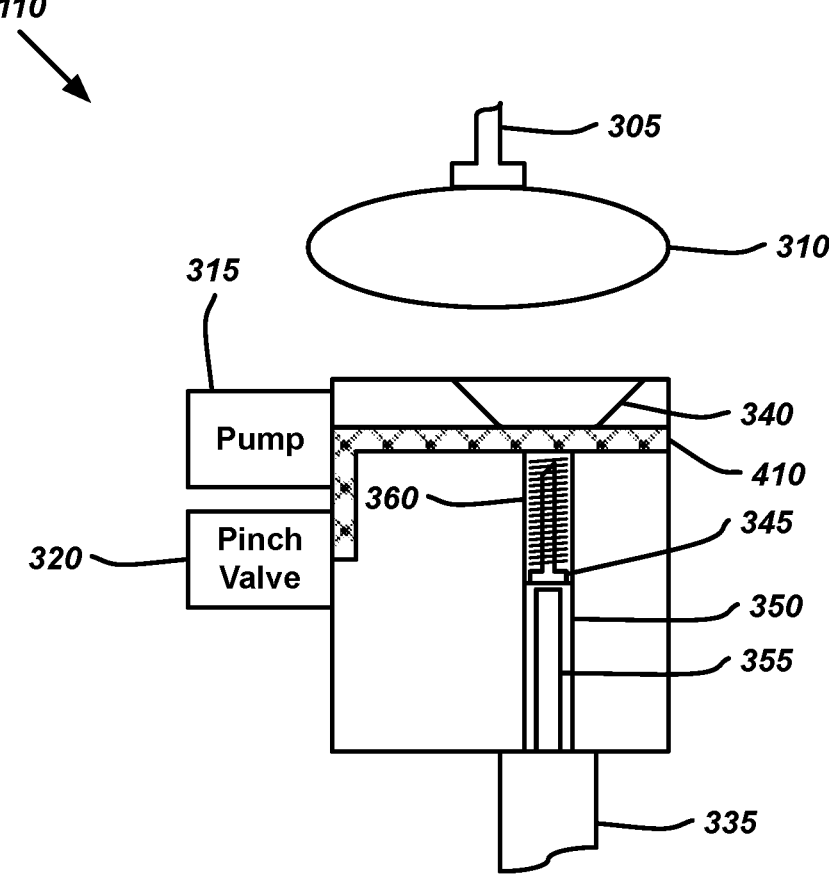
FIG. 4 illustrates a side elevation view of another exemplary embodiment of the sample processing module included in the sample collection and testing device of FIG. 1.

FIG. 4 illustrates a side elevation view of another exemplary embodiment of the sample processing module 110. In this example, the chip 410 may be located at the sample collection point (e.g., receptacle 340 where the finger is placed). The chip 410 may be made from a flexible material such as silicone. In such embodiments, the needle 345 may be placed below the chip 410 and pierce the chip 410 before pricking the finger. The material may then seal itself after the needle 345 is retracted such that the blood is retained within the chip or sample collection cavity 410. In this example, the needle 345 is in a fully retracted position whereas in the example of FIG. 3, the needle was in a partially or fully extended state.

In this example, the needle housing 350 may be split into two portions (a top portion and a bottom portion from this view), where one portion (i.e., the top portion in this example) is included in the disposable insert 360 of some embodiments. Other components may be included in the disposable insert, such as the needle and spring 345, the chip 410, and the receptacle 340. As above, any electronic sensing plate may be included in the removable cartridge 360 along with the chip 410 or may be included with the non-disposable components.

In the examples of FIG. 3 and FIG. 4, different embodiments may include different components within the disposable cartridge of some embodiments. Likewise, various different components may be included within the non-disposable elements of the device 100. Such components may be distributed among the disposable and non-disposable portions based on various relevant criteria (e.g., component cost, availability of components, cartridge footprint, device sensing capabilities, etc.).

FIG. 5 illustrates a side elevation view of an exemplary embodiment of a cartridge 500 used by some embodiments (e.g., cartridge 240 described above). FIG. 6 illustrates a top plan view of the exemplary cartridge 500. FIG. 7 illustrates a bottom plan view of the exemplary cartridge 500. As shown, the cartridge may include a top plate 510, microfluidic chip 520, and a bottom plate 530.

The top plate 510 may be made of rigid or semi-rigid material (e.g., plastic, metal, etc.). The top plate may include various clips or fasteners 540 or other elements that may secure the top plate 510 to the bottom plate 530 (thus securely housing the chip 520). Different embodiments may couple the top plate 510 to the bottom plate 530 in various appropriate ways using various appropriate elements (e.g., screws, magnets, nuts and bolts, adhesives, tabs and slots, latches, etc.). Fasteners 540 may be distributed about the perimeter of the top plate 510.

The top plate 510 may also include a receptacle 610 with an opening 620 for sample collection. The receptacle 610 and opening 620 may be sized such that a typical user is able to put a fingertip in contact with the edges of the opening 620 such that a tight seal is formed between the skin and the receptacle 610. For instance, the opening 620 may be sized to have a larger diameter than shown, as compared to the receptacle 610. In addition, other attributes of the receptacle 610 and/or opening 620 may be varied (e.g., slope, contour, size, shape, material, texture, etc.) in order to generate necessary pressure for sample collection.

The top plate 510 may further include various through-holes 630 that correspond to "pinch points" of the chip 520. Such pinch points may prevent fluids from flowing within the chip until a test is conducted. In addition, after a test is completed, the pinch points may allow a used chip to be sealed such that fluids will not leak out. The pinch points may also be used when manufacturing cartridges. Cartridges may include various cavities that may be pre-filled with various fluids (e.g., thinners, test solutions, antibodies, etc.). Such cavities may be filled by injecting a syringe into the cavity, depositing the fluid, retracting the syringe, and sealing the entry hole. By activating the pinch points, the fluid may be retained in the designated cavities during manufacturing and storage prior to use.

In addition to the top plate 510, some embodiments may include a cover (not shown). Such a cover may be included over the top plate such that elements of the test cartridge 500 are protected (e.g., the sample collection point may be covered to prevent contamination). In addition, the cover may include various prongs that engage the pinch points of the chip 520 via through-holes 520. The cover may include various clips or connectors that may secure the cover to the other elements of the cartridge 500. The clips or connectors may be automatically released with the cartridge is placed in the SCTD 100 such that the cover may be removed. When the test is complete, the cover may be reattached to secure the cartridge 500 for disposal.

The chip 520 may be similar to chip 325 and chip 410 described above. The chip 520 may include various cavities, fluid conduits, optical access points, and/or other appropriate elements. The chip may include cavities that are pre-filled with various solutions, materials, etc. In some embodiments, the chip may include fluid sensing plates, connectors, etc. Such sensing elements may be contact and/or non-contact with respect to the fluid under test. The chip may be made of flexible material such as silicone.

The bottom plate 530 may be made of rigid or semi-rigid materials (e.g., plastic, metal, etc.). The bottom plate may include a lancet housing 550 and cap 560, which include a channel 570 for use by a lancet actuator of some embodiments. In addition, the bottom plate 530 may include various test leads or other connectors 580 that may be used to analyze samples, interface with various cartridge elements, etc. In some cases, the leads may extend into the chip 520 such that direct contact measurements may be conducted.

The bottom plate 530 may include various placement guides 710 that may align the cartridge 500 with a complementary receptacle of the SCTD 100. In addition, the bottom plate 530 may include various cavities or access areas 720 that may allow various elements of the SCTD 100 to engage the chip 520. For instance, some embodiments may include an access area 720 for each pump that will engage the chip 520.

The bottom plate 530 may include a needle guide 730. The needle guide may be an appropriately-sized through-hole that maintains needle alignments during sample generation.

FIG. 8 illustrates a side elevation view of the exemplary cartridge 500, including an exploded view of an exemplary lancet assembly 800. As shown, the lancet assembly may include a spring 810, a needle or lancet 820, a needle base or housing 830, a needle cup 840, and an actuator interface 850.

The spring 810 may include a linear spring and/or other components that are able to retain the lancet assembly 800 at a starting position (and return the assembly to the starting position).

The needle 820 and base 830 may be standard lancet-type needles typically used for blood sample collection. The length of the exposed portion of the needle 820 may be varied across different embodiments depending on various relevant factors (e.g., test type, user attributes, user preferences, etc.).

The needle cup 840 may be made from rigid material such as plastic or metal. The needle cup may be sized and shaped such that it is able to move along the housing 550 when manipulated by actuator interface 850. In addition, the interior cavity of the needle cup 840 may be sized and shaped to securely hold the lancet base 830 such that the needle 820 is extended along a consistently straight path.

The actuator interface 850 may be shaped and sized appropriate to move along groove 570 such that lancet alignment is maintained through guide 730. Different embodiments may include different actuator interfaces, depending on the type of lancet assembly, type of actuator, and/or other relevant factors. In this example, the bottom of the cup 840 may rest on the actuator interface 850 as the cartridge 500 is inserted into the SCTD 100. The actuator interface 850 may be coupled to the actuator.

FIG. 9 illustrates a side elevation view of an exemplary embodiment of a lancet actuator 900 included in the SCTD 100. FIG. 10 illustrates a side elevation view of the lancet actuator 900 in an extended position. FIG. 11 illustrates a top plan view of the top portion 910 of the lancet actuator 900. FIG. 12 illustrates a bottom plan view of the bottom portion 920 of the lancet actuator 900.

As shown, the actuator 900 may include a top portion 910 and a bottom portion 920 movable coupled along contour 930. In addition, some embodiments may include a center shaft or guide 940. The contour 930 of the coupling between the portions 910-920 may at least partially define various attributes of the lancet extension and retraction (e.g., depth, speed, acceleration, torque, duration, etc.). As such, different embodiments may utilize differing contours 930 depending on various relevant factors (e.g., type of test, user attributes, user preferences, etc.). In addition, some embodiments may adjust various parameters associated with the motor or driver for the actuator 900 (e.g., voltage, current, etc.).

The top portion 910 may be made from rigid materials such as metal or plastic. The top portion may include a through-hole or other receptacle 1110 that is able to be movably coupled to guide 940 such that the top portion 910 is able to move back and forth (or up and down in the pictured orientation) along the guide 940. In addition, the top portion 910 may include the actuator interface 850 and one or more additional guides 1120 that may engage associated receptacles (not shown) of the SCTD 100 (or cartridge 500, and/or other appropriate elements). Such alignment guides may help ensure that the lancet 820 is projected along a consistent path and is thus consistently aligned relative to a subject.

The bottom portion 920 may be made of rigid materials such as metal or plastic. The bottom portion may include a through-hole or other receptacle 1210 that is able to be movably couple to guide 940 such that the bottom portion 920 is able to rotate about the guide 940. The bottom portion 920 may include a drive arm 1220 that is able to engage an arm or other member coupled to a motor (e.g., a rotary motor, a linear actuator, etc.).

During operation, the bottom portion 920 may be rotated up to ninety degrees, such that the actuator interface 950 is moved along the guide 940 in an upward direction 1010 (or appropriate direction for the orientation of a particular lancet assembly and cartridge) toward the extended position shown in FIG. 10. The bottom portion 920 may then be returned to the starting position (e.g., zero degrees of rotation), thus returning the actuator interface 850 to the starting position shown in FIG. 9. Of course, the lancet assembly will also move along an axis aligned with guide 940 such that the lancet 820 is extended beyond the top plate 510 in order to engage a subject and then return to a starting position where the needle 820 is safely below the top plate 2510.

Some embodiments may utilize a two-step extension and retraction process where the bottom portion may be rotated such that the lancet 820 pierces the microfluidic chip 520 and is located as close to the finger as possible. The process may then extend and retract the lancet 820 to engage the subject and generate a sample. Such an approach may allow the chip to be pierced at a slow speed but the finger poking speed may be relatively higher.

Figure 13:
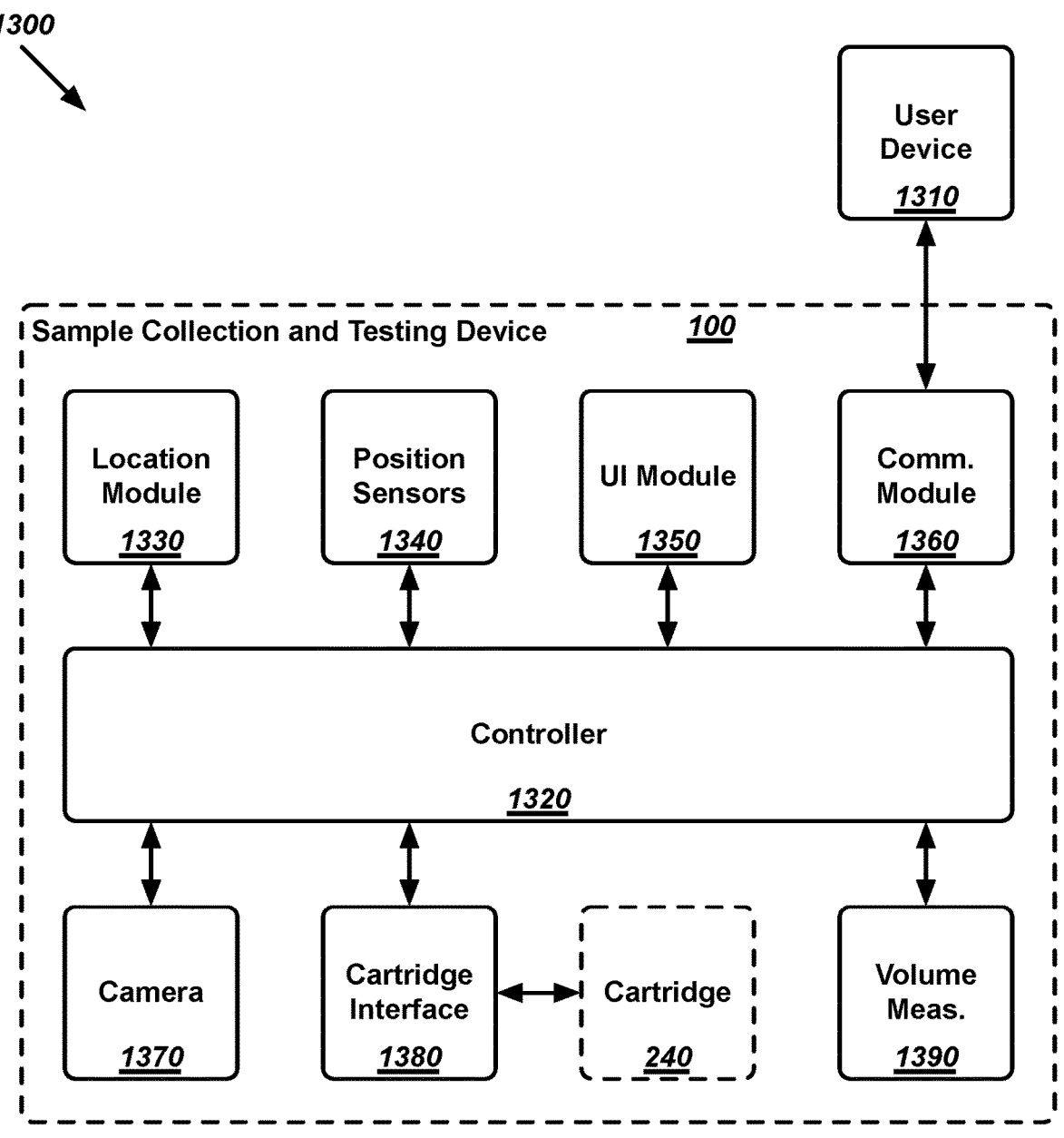
FIG. 13 illustrates a schematic block diagram of a system including the automated sample collection and testing device of FIG. 1.

FIG. 13 illustrates a schematic block diagram of a system 1300 including the automated SCTD 100, sample processing module 110, and a user device 1310. As shown, the SCTD 100 may include a controller 1320, location module 1330, position sensors 1340, UI module 1350, communication module 1360, camera 1370 (and/or other appropriate sensors), cartridge interface 1380, and volume measurement module 1390.

The sample processing module 110 may be similar to that described above in reference to FIG. 2, FIG. 3, and FIG. 4. The module 110 may include a removable test cartridge. The cartridge, or portions thereof, may be disposable (i.e., intended for a single use). several exemplary modules 110 will be described in more detail in reference to FIG. 16-FIG. 18 below.

The user device 1310 may be an electronic computing device, such as a smartphone, tablet, personal computer, medical device, etc. The user device may provide various system features, such as UI output elements (e.g., display of test results, status, etc.), UI input elements (e.g., menus, buttons, etc.), and/or connectivity (e.g., via a cellular or wireless network connection). In some embodiments, the user device may be able to at least partly control the operations of the SCTD 100. For instance, a user such as a medical professional may initiate a test sequence by pressing a button on a tablet after a subject has been properly positioned with respect to the SCTD 100 (and sample collection element thereof).

The controller 1320 may be an electronic device that is able to execute instructions and/or process data. The controller may be able to at least partly direct the operations of the other components. The controller may be associated with a local memory (not shown) that is able to store instructions and/or data.

The location module 1330 may include various electronic components that are able to determine a geographic location. Such components may include, for instance, global positioning system (GPS) components.

The position sensors 1340 may include various sensors, accelerometers, gyroscopes, etc. that may be able to determine a relative position of the SCTD. Such components may be used to ensure, for instance, that the SCTD is on a level surface. Some embodiments may include components that are able to automatically adjust device position based on such sensor measurements.

The UI module 1350 may include various buttons, touch-screens, displays, indicators, keypads, microphones, speakers, etc. that may allow interaction with a user and/or subject.

The communication module 1360 may be able to communicate across one or more wired or wireless pathways. Such pathways may include, for instance, universal serial bus (USB), Bluetooth, Wi-Fi, Ethernet, the Internet, etc.

The camera 1370 (and/or other appropriate sensors) may be a color, HD camera that is able to capture video and/or still photographs. Such captured data may be able to be automatically analyzed by the controller and/or other components. Other embodiments may include different types of sensors such as environmental sensors (e.g., temperature, humidity, elevation, barometric pressure, etc.), subject attribute sensors (e.g., temperature, pulse rate, blood pressure, etc.), etc. In some embodiments, the sensors may be provided by one or more external components, with a resource such as controller 1320, via communication module 1360, may retrieve the data from such external components.

The cartridge interface 1380 may include various components appropriate for interaction with a removable test sample processing module 110. For instance, some embodiments may utilize the camera 1370 to scan a graphic code on the test cartridge. As another example, some embodiments may include components that are able to read radio frequency identification (RFID) tags or other similar tags. As still another example, some embodiments may be able to retrieve information through a digital or analog connection to the sample processing module 110. As yet another example, some embodiments may utilize near-field communication (NFC).

In some embodiments, the cartridge interface 1380 and sample processing module 110 may have shared elements, complementary elements, and/or otherwise associated components that may together provide various functions described in reference to the cartridge.

The volume measurement module 1390 may be able to interact with the cartridge interface 1380 (and/or other appropriate elements) in order to determine volume measurements associated with sample fluids. As described in more detail in reference to FIG. 21 below, the volume measurement module 1390 may include and/or interact with various other elements (e.g., optical sources and sensors) that are able to determine a volume of a fluid sample.

Figure 14:
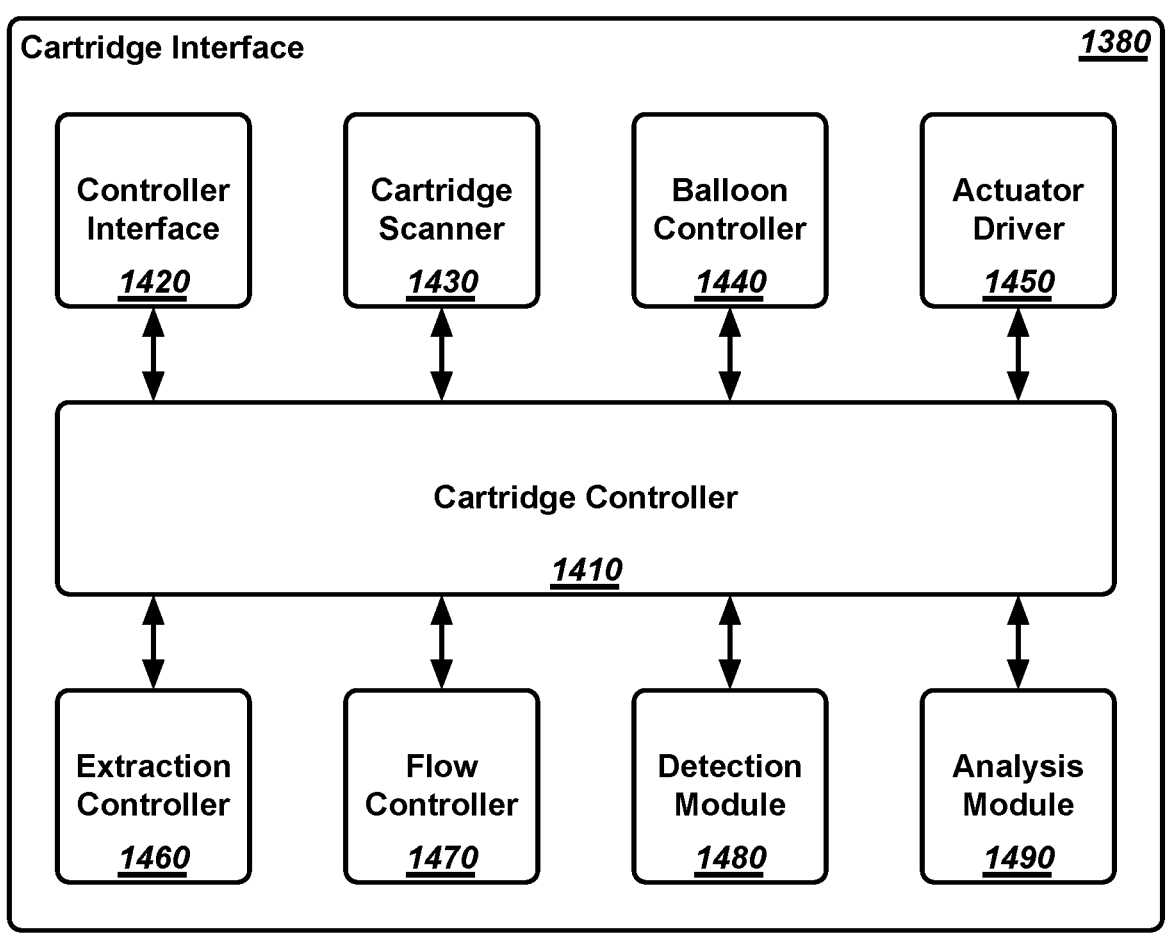
FIG. 14 illustrates a schematic block diagram of a cartridge interface included in the automated sample collection and testing device of FIG. 1.

FIG. 14 illustrates a schematic block diagram of a cartridge interface 1380 included in the automated sample collection and testing device 100. The interface 1380 may be able to access various components of the SCTD 100 and/or the cartridge 240. As shown, the cartridge interface 1380 may include a controller 1410, a controller interface 1420, a cartridge scanner 1430, a balloon controller 1440, an actuator driver 1450, an extraction controller 1460, a flow controller 1470, a detection module 1480, and an analysis module 1490.

The controller 1410 may be an electronic device that is able to execute instructions and/or process data. The controller may be able to at least partly direct the operations of the other components. The controller may be associated with a local memory (not shown) that is able to store instructions and/or data.

The controller interface 1420 may interface with the controller 1320 of the SCTD 100. In some embodiments, controller 1320 may serve as controller 1410 and interface 1420.

The cartridge scanner 1430 may be able to scan a cartridge using radio frequency scanning (for cartridges with RF tags, NFC tags, etc.), optical scanning (for cartridges with graphic codes), and/or other appropriate components that may be used to determining identifying information regarding a cartridge.

The balloon controller 1440 may control operations of a balloon (e.g., balloon 310) and/or associated pumps or other components in order to ensure sufficient retention of a subject appendage for sample collection.

The actuator driver 1450 may control operations of an actuator (e.g., actuator 335 or 900) in order to control lancet extension and retraction.

The extraction controller 1460 may be able to direct elements, such as pumps, that may be used to extract and collect a sample.

The flow controller 1470 may be able to direct elements, such as pumps, valves, etc., that may affect flow along various pathways of the chip 520.

The detection module 1480 may measure information related to a test associated with a cartridge. Such detection may include, for instance, charge detection, magnetic detection, impedance measurements, etc.

The analysis module 1490 may analyze detected measurements and/or identify test results.

Figure 15:
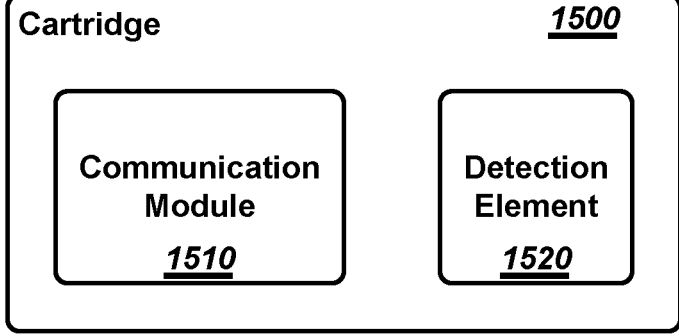
FIG. 15 illustrates a schematic block diagram of a cartridge used by the automated sample collection and testing device of FIG. 1.

FIG. 15 illustrates a schematic block diagram of a cartridge 1500 used by the automated SCTD 100. The cartridge 1500 may be similar to cartridge 240 or cartridge 500 described above. As shown, the cartridge 1500 may include a communication module 1510 and one or more detection elements 1520.

The communication module 1510 may provide NFC and/or other communication capabilities. The module may have an associated storage. Such elements allow used cartridges to be "tagged" such that the cartridges are prevented from being used by multiple users or multiple times by the same user.

The detection elements 1520 may include various contact and/or non-contact elements that may provide measurement capabilities. Such elements may include various leads or connectors that may interface with the SCTD 100. In some embodiments, the detection elements 1520 may transmit data via the communication module 1510.

Figure 16:
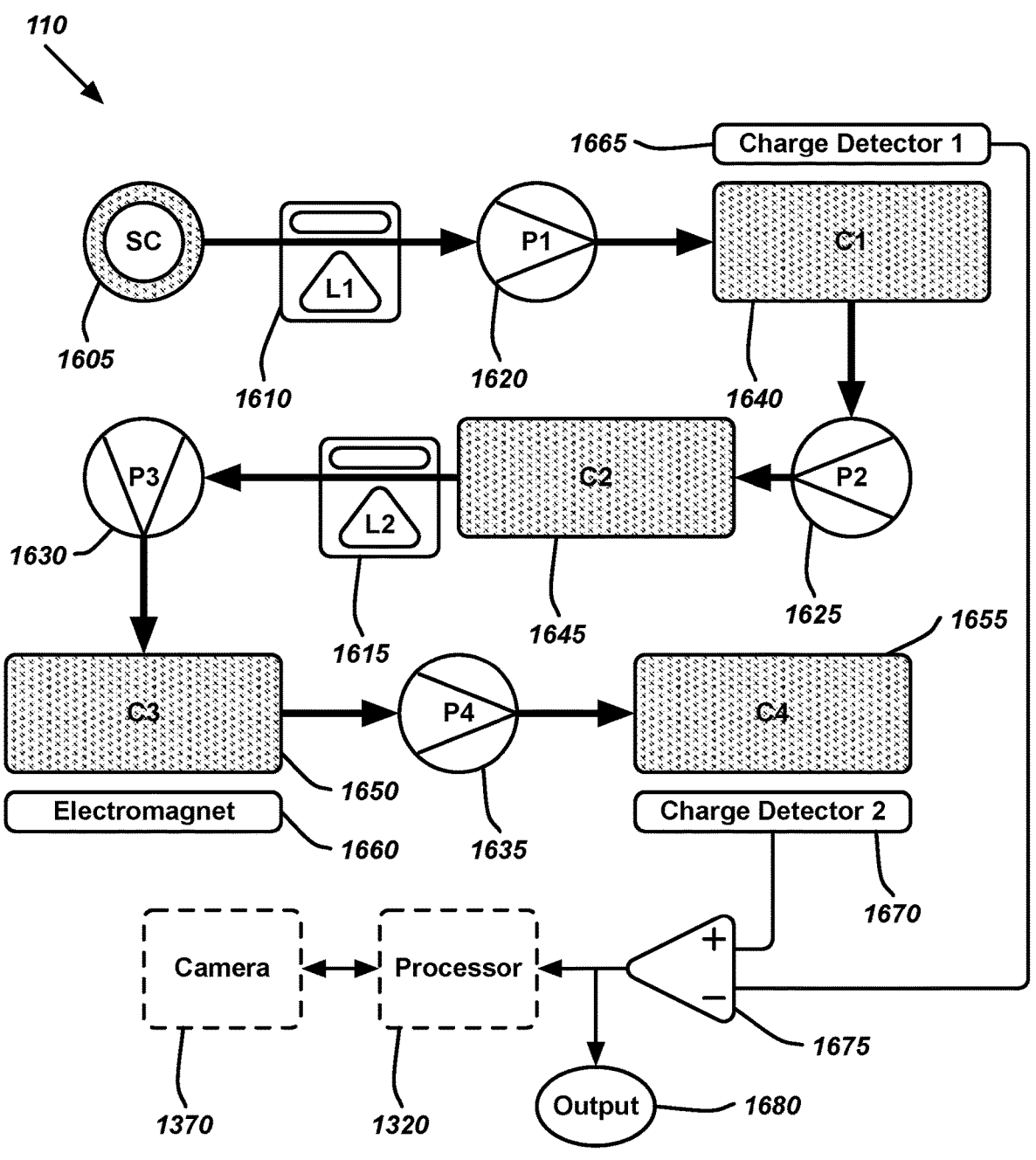
FIG. 16 illustrates a schematic block diagram of an exemplary embodiment of the sample processing module included in the sample collection and testing device of FIG. 1.

FIG. 16 illustrates a schematic block diagram of an exemplary embodiment of the sample processing module 110. As shown, this example module may include a sample collection element 1605, multiple optical measurement elements 1610-1615 (e.g., lasers, LED light sources, etc.), multiple bi-directional pumps 1620-1635, multiple cavities 1640-1655, an electromagnet 1660, a pair of charge detectors 1665-1670, a differential output generator 1675, a camera 1370, and a processor 1320. This example sample processing module 110 is associated with tests to diagnose cancer. Different embodiments may include different components and/or arrangements of components when associated with other tests (e.g., blood sugar levels).

The sample processing module 110, or portions thereof, may be self-contained such that each subject may use a new disposable cartridge. As such, the fluid collected by the cartridge may be completely contained within the cartridge and not exposed to the SCTD device 100. The cartridge elements may be made out of (and/or enclosed or embedded in) appropriate materials that are impervious to the various fluids collected or used within the sample processing module 110. Such materials may include plastics, silicone, composites, etc. In this example, the fluid flow pathway is indicated by thicker arrows, while communicatively coupled elements are indicated by thinner lines or arrows. In addition, the components that contact the sample are indicated by a fill pattern.

In some embodiments, the disposable cartridge portion may include the sample collection element 1605, the cavities 1640-1655, and the tubing between them. Such a configuration allows the more expensive components (such as pumps, optical detectors, etc.) to be reused across multiple cartridges.

The sample collection element 1605 may be similar to that described above in reference to FIG. 3 or FIG. 4. At minimum, the sample collection element may include a cavity that is able to receive an amount of fluid for testing. In some embodiments, the cavity may include a fluid sensing chip. Some elements of the sample collection element (e.g., the pump or pinch valve) may be shared with other elements of the sample processing module 110. For instance, pump 1620 may act as pump 315 in some embodiments.

Each of the pumps 1620-1635 may be a peristaltic or other appropriate pump that is able to move fluid along a flow pathway (e.g., the areas indicated by the fill and thick arrows). Such a pathway may include various flexible tubes or cavities within a fluid retaining housing (e.g., a silicone housing). In some embodiments, a peristaltic pump may move fluid along the pathway. Such pumps may also act as valves, such that when the pumps are not operating, fluid flow between cavities (and/or other elements along the pathway) is prevented.

Each of the multiple optical measurement elements 1610-1615 (or other optical sensors, or other types of volume measurement sensors) may include a source and a collector or absorber. The optical measurement elements may be placed along the fluid flow pathway such that fluid flow is able to be detected. The optical sensors 1610-1615 of some embodiments may be utilized without contacting the fluid sample. In this way, the cost of cartridges may be reduced as the sensors are able to be used across numerous samples.

Each of the multiple cavities 1640-1655 may be able to store an appropriate amount of fluid. The cavities may be connected to the flow pathway at multiple locations (e.g., an input and an output).

The electromagnet 1660 may include various appropriate components that are able to provide a controllable magnet.

The pair of detectors 1665-1670 (e.g., charge detectors, impedance detectors, conductivity detectors, etc.) may include various elements such as metal plates, capacitors, circuitry, etc. that may be able to detect and/or store charge, and/or otherwise sense qualities of the cavity contents.

The differential output generator 1675 may be able to receive the outputs of the charge detectors 1665-1670 and generate a signal 1680 that is proportional to a difference in sensed charge at each charge detector 1665-1670. The differential output 1680 may be provided as an analog and/or digital signal. The output may be provided to a processor 1320, as shown, and/or may be provided directly to an external resource such as the SCTD 100.

The camera 1370 may be able to capture images and/or video associated with the sample processing module 110. The camera 1370 may be placed above the sample processing module 110 such that activity inside the cartridge may be monitored. The camera 1370 may be able to track fluid movement (and/or other appropriate factors) in real time such that adjustments may be made or problems identified. In some embodiments, the camera may be associated with the SCTD 100 rather than included in the disposable cartridge in order to reduce cartridge cost. The camera 1370 may be high definition, 4K, and/or other appropriate formats of any resolution. Higher resolutions may provide more image processing capability if needed.

The processor 1320 may be an electronic device capable of executing instructions and/or processing data. The processor may be able to at least partly control the operations of the various other components (although various connections have been omitted for clarity). For instance, the processor may direct the operations of the electromagnet 1660. As another example, the processor 1320 may receive and analyze data from the optical measurement elements 1610-1615. The processor 1320 may have an associated memory (not shown).

Although this example includes charge detectors 1665-1670 and an electromagnet 1660 that are used for charge differential detection, other embodiments may utilize other sensing components. For instance, some embodiments may include active electronic components such as sensors that directly contact the fluid sample. In such cases, a signal from such a component may be received and analyzed by the processor 1320 of some embodiments (and/or other appropriate components such as a sensor interface). Some embodiments may utilize inductive power and wireless data exchange such that no physical connections to the chip are needed.

Figure 17:
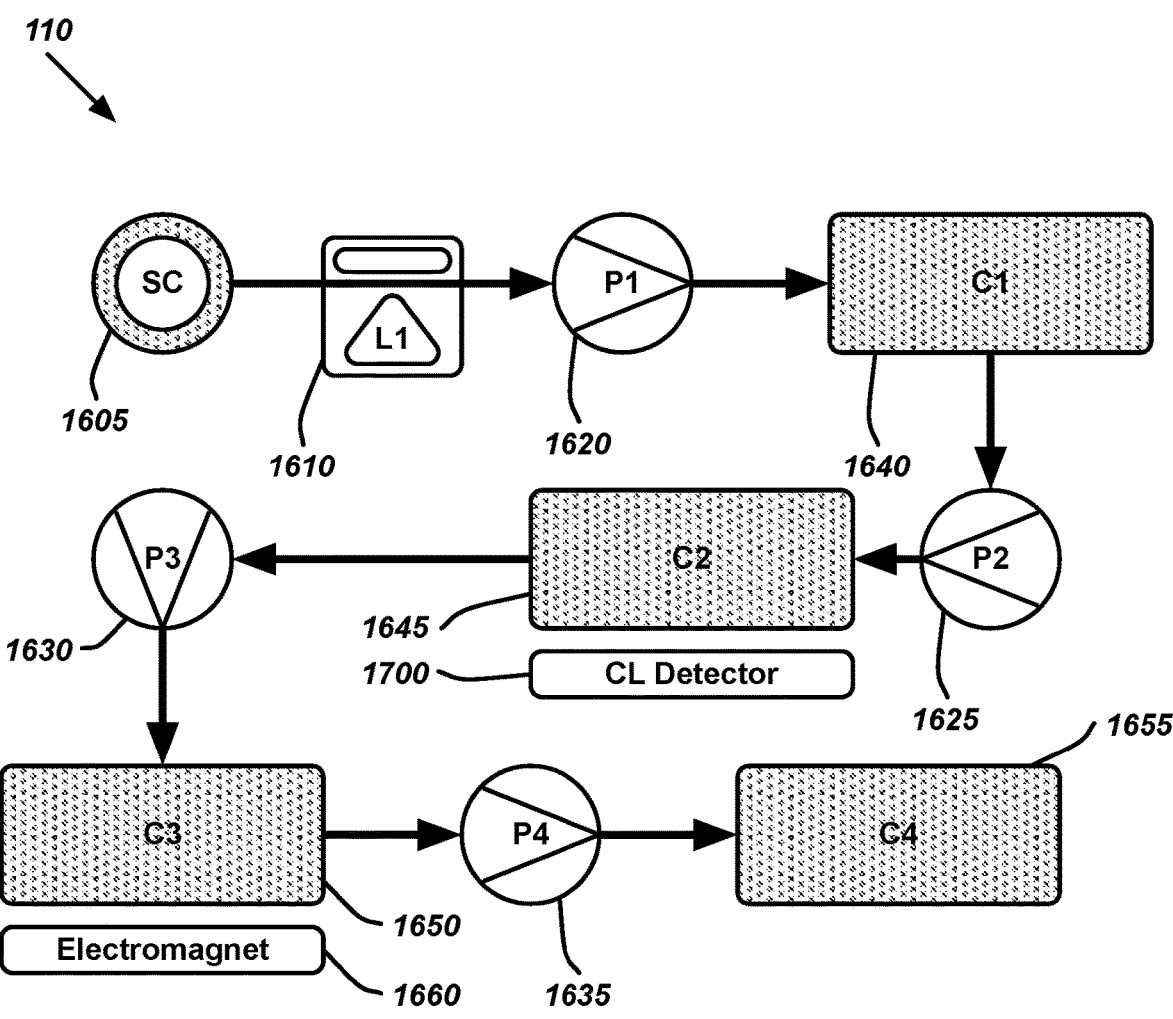
FIG. 17 illustrates a schematic block diagram of a second exemplary embodiment of the sample processing module included in the sample collection and testing device of FIG. 1.

FIG. 17 illustrates a schematic block diagram of a second exemplary embodiment of the sample processing module 110. As shown, the module may include many of the same components as the module of FIG. 16. In the example of FIG. 17, the second cavity 1645 may be associated with a chemiluminescence (CL) detector 1700. Such a detector may be able to sense photons emitted from CL particles. In addition, unlike the example of FIG. 16, the charge detectors 1665-1670 and second measurement element 1615 are not needed. The output of the CL detector 1700 may be converted to a discrete value and supplied to a processor (and/or other appropriate elements), as in FIG. 16. Similar such processing elements may at least partly direct the operations of the components of the sample processing module 110.

As above, in this example, the fluid flow pathway is indicated by thicker arrows, while communication pathways among elements are omitted for clarity. In addition, the components that contact the sample are indicated by a fill pattern.

Figure 18:
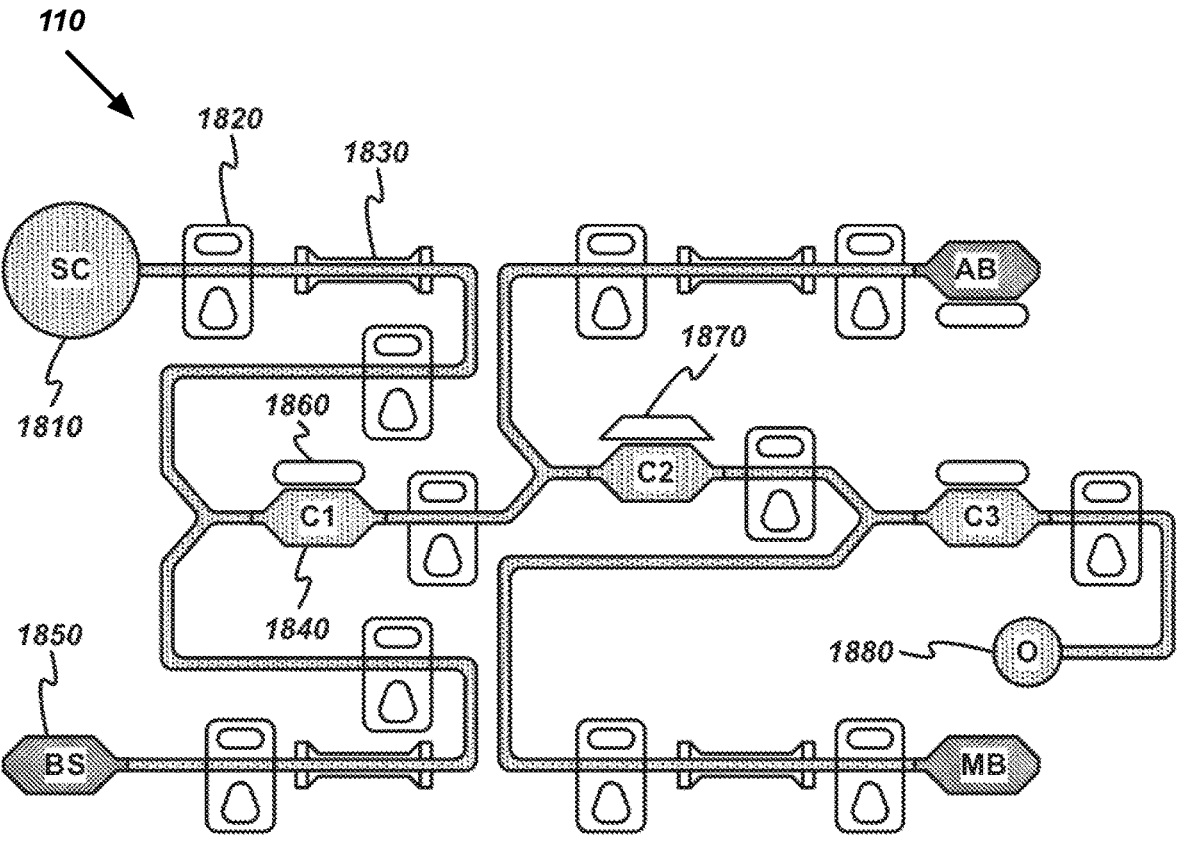
FIG. 18 illustrates a schematic block diagram of a third exemplary embodiment of the sample processing module included in the sample collection and testing device of FIG. 1.

FIG. 18 illustrates a schematic block diagram of a third exemplary embodiment of the sample processing module 110. As shown, the module may include a sample collection element 1810, multiple optical measurement elements 1820, multiple bi-directional pumps 1830, multiple empty cavities

1840, multiple pre-filled cavities 1850, multiple detectors 1860, at least one electromagnet 1870, and a fluid output port 1880.

The sample collection element 1810 may be similar to element 1605 described above. Each optical measurement element 1820 may be similar to measurement elements 1610-1615 described above. In this example, measurement elements 1820 are located throughout the module 110. Such an arrangement may be useful while developing or testing a new module or cartridge. Some embodiments may omit some such elements in order to reduce cost. Each bi-directional pump 1830 may be similar to pumps 1620-1635 described above. The electromagnet 1870 may be similar to electromagnet 1660 described above.

Each empty cavity 1840 may be similar to cavities 1640-1655 described above. Each pre-filled cavity 1850 may be similar to cavities 1640-1655 described above and may include various solutions, materials, etc. that may be used during performance of the associated test. In this example, a first pre-filled cavity 1850 includes a buffer solution (BS), a second pre-filled cavity includes antibodies (AB) that may be electrically charged or tagged with particles that are attached to the AB molecules (e.g., gold particles of various sizes), and a third pre-filled cavity includes certain agents or proteins attached to magnetic beads (MB). The size and/or other characteristics of each cavity 1840-1850 may depend on various relevant factors (e.g., desired volume, properties of stored solutions or materials, etc.).

Each detector 1860 may be capable of detecting various attributes of the contents of an associated chamber 1840 or 1850. Such attributes may include, for instance, charge, impedance or conductance, pH level, color or other visual attributes, and/or any other measurable attribute of the fluid.

The fluid output port 1880 may allow fluid to be provided to an external element via the cartridge of some embodiments. For instance, the cartridge may be removed and fluid collected from the cartridge for further analysis.

In this example, elements having a fill pattern are associated with a disposable portion of the module 110, while elements having no fill pattern are associated with the reusable portion of the module.

The outputs of the detectors 1860 may be converted to a discrete value and supplied to a processor (and/or other appropriate elements), as in FIG. 16. Likewise, such elements may be able to at least partly direct the operations of the various pumps 1830, measurement elements 1820, sample collection element 1810, detectors 1860, electromagnet 1870, etc.

Several sample operations of the sample processing modules of FIG. 16-FIG. 18 will be described in more detail in references to processes 3900-4100 below. In these examples, the sample collection modules may include similar (or the same) reusable components. For instance, although the different examples may include different numbers of cavities within the disposable cartridge, each example uses the same number of pumps (where the layout of each different cartridge may be arranged to utilize those pumps). Different embodiments may utilize different numbers of pumps (or other such reusable components) as well. In addition, the reusable components may include elements (e.g., the CL detector 1700) that are only used by some embodiments of the disposable cartridge.

Figure 19:
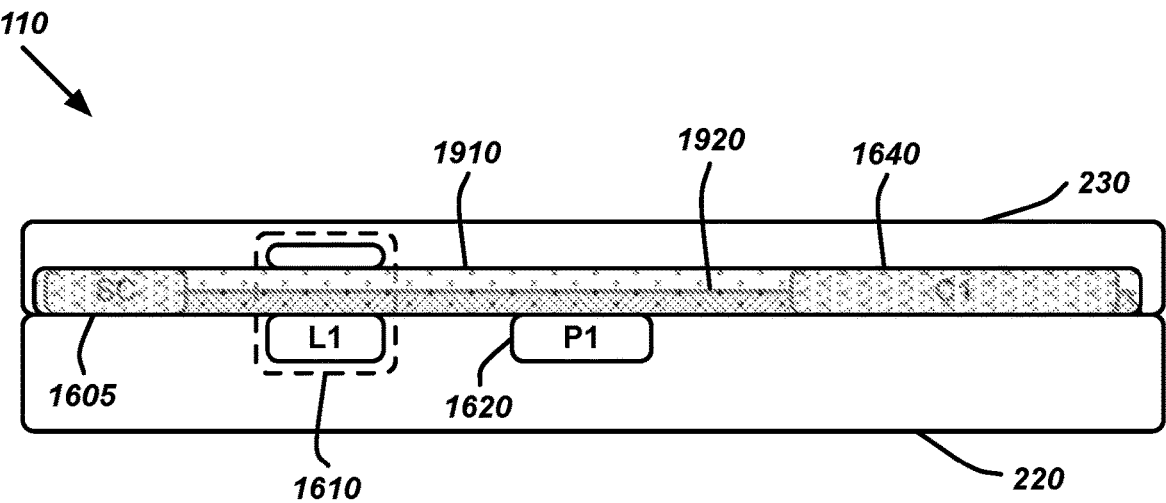
FIG. 19 illustrates a partial side view of a sample processing module according to an exemplary embodiment.

FIG. 19 illustrates a partial side view of a sample processing module 110 including a disposable cartridge (or "insert") 1910 according to an exemplary embodiment. This example includes a sub-set of the components described above in reference to FIG. 16.

As shown, the sample processing module 110 of FIG. 19 may include the removable insert 1910 including a fluid flow pathway 1920, a top portion 230, and a bottom portion 220. In some embodiments, the top and bottom 220-230 may be reusable and may include a solid housing made of, for example, plastic or metal. The top and bottom may be coupled together (and/or to the device housing) in various appropriate ways, including hinges, latches, tabs and sockets, nuts and bolts, compression fit, magnets, etc.

The removable insert 1910 may be made of (or housed within) a flexible material such as silicone such that inserts may be inserted into and/or removed from the cartridge housing. The insert may include various ridges, notches, slots, cavities, receptacles, etc. that may engage complementary elements of the cartridge housing.

Figure 20:
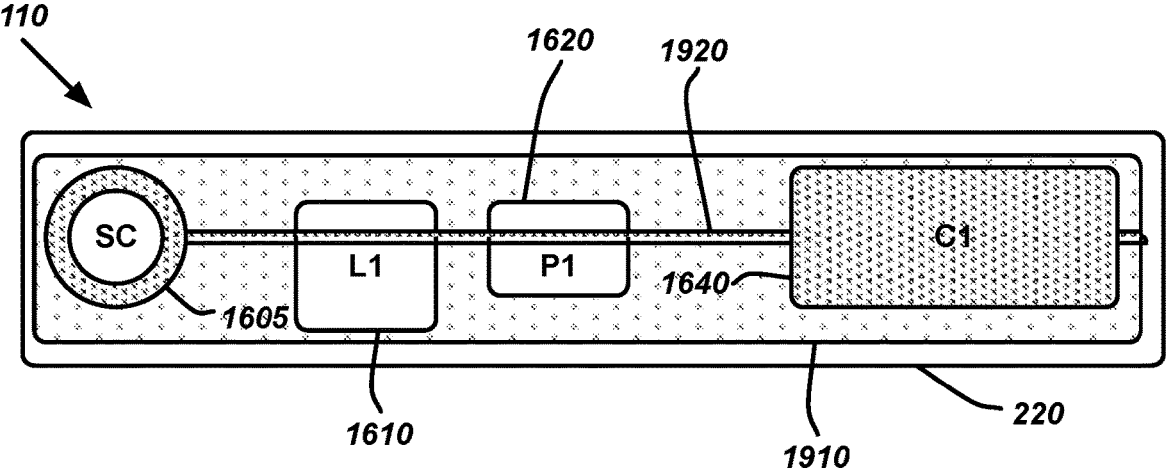
FIG. 20 illustrates a partial top view of a sample processing module according to an exemplary embodiment.

FIG. 20 illustrates a partial top view of a disposable insert 1910 and sample processing module 110 according to an exemplary embodiment. This example includes the same sub-set of components shown in FIG. 19. In the view of FIG. 20, the top portion 230 has been omitted for clarity.

As shown, the disposable insert 1910 may house at least a portion of the sample collection element 1605, cavity 1640, and cylindrical tubes or other appropriate connectors. The pump 1620 may engage a portion of the flow pathway 1920 without contacting the sample. For instance, the pump 1620 may be a peristaltic pump that includes a rotating member with a number of protruding ridges aligned with a portion of the insert tubing 1920. The optical measurement element 1610 may be associated with a transparent or semitransparent portion of the insert 1910 and associated tubing 1920. The optical measurement element 1910 may be oriented vertically, as in FIG. 19, horizontally, as in FIG. 20, and/or other may utilize other appropriate orientations.

Figure 21:
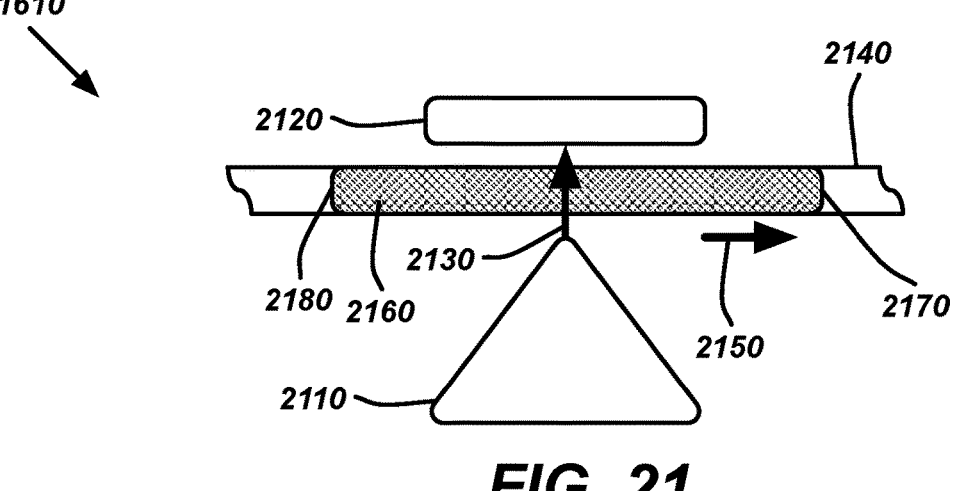
FIG. 21 illustrates a side elevation view of an optical measurement element according to an exemplary embodiment.

FIG. 21 illustrates a side elevation view of an optical measurement element 1610 or 1615 according to an exemplary embodiment. As shown, the optical measurement element may include an emitter 2110, an absorber 2120, a beam 2130, a fluid path 2140, forward flow direction 2150, fluid sample 2160, starting edge (or "leading" edge) 2170, and ending edge (or "trailing" edge) 2180. The operation of the components of the optical measurement element 1610 may be at least partly controlled by a resource such as controller 1320.

At least some portions of the pathway 2140, including any portions associated with a beam 2130, may be translucent or semi-translucent such that more energy is able to be measured at the absorber 2120. When an opaque or semi-opaque fluid (such as blood) passes through that portion of the pathway 2140, the amount of energy measured at the absorber 2120 may decrease versus the energy absorbed when there is a lack of fluid in the pathway. An appropriate threshold may be set such that fluid flow at the particular location may be detected. The optical sensors 1610 may be placed before and/or after an associated pump (and/or other appropriate components).

In this example, the emitter 2110 is on one side of the fluid path 2140 while the absorber 2120 is on an opposite side. The path 2140 may be embedded into an insert, such as path 1920 in insert 1910. In some embodiments, the emitter 2110 and absorber 2120 may both be on one side of the fluid path 2140 (e.g., both may be housed within the bottom portion 220 of the sample processing module 110), while a reflective element is located on the opposite side. Such embodiments may reduce the cost of components included in the disposable cartridge 240. In some embodiments, the absorber(s)

2120 may be located within the top portion 230 of the sample processing module. In other embodiments, the emitter(s) 2110 may be located within the top portion 230 of the sample processing module while all other components are included within the bottom portion 220.

Some embodiments may include other types of optical sensors. For instance, some embodiments may utilize an LED light source and a photodetector. The photodetector may have an analog output that is fed to an analog to digital converter for processing. Such a scheme may be used to measure volume by determining a length of fluid (e.g., several microns), and calculating a volume based on a diameter of a tube or other connecting element. The output of the photodetector may be analyzed by a processor to determine the beginning and end of a volume of fluid. Such an approach may allow very accurate measurement of volumes.

Some embodiments may capture, store, and/or analyze a signal that is generated based on the output of the photodetector or other absorbing element. Such an approach may allow the device to handle issues such as gaps in the fluid sample along the pathway. The signal may be stored (along with other test parameters) for future analysis.

In some embodiments, the detector 1610 may measure a volume of fluid by incrementing a counter while the detector 1610 senses an opaque fluid, where the count may be able to be translated to a fluid volume based on the sizing of the tubing 2140 and count value. As each count increment may be associated with a very small amount of fluid, counting a large number of increments (e.g., five hundred, one thousand, etc.) may provide an accurate measure of volume.

In some embodiments, multiple detectors may be placed serially along a path in order to measure flow rate or viscosity. Of course, as in the example of FIG. 18, such detectors may be utilized for other purposes as well. Such flow rate detection may be used to measure performance of blood thinners. For instance, a leading edge of a sample may be detected at a first detector at a first time. The leading edge of the sample may be detected at a second detector at a second time. The difference between the first time and the second time may be used to calculate a "thickness" or viscosity parameter that may be used to evaluate the performance of the blood thinner.

FIG. 22 illustrates a schematic block diagram of an optical measurement element 1610 according to an exemplary embodiment. As shown, the optical measurement element may include an emitter 2110 and an absorber 2120. The emitter 2110 may include one or more optical sources 2210. The absorber 2120 may include a sensor 2220, digitizer 2230, filter 2240, camera 2250, and UI interface 2260.

Each optical source 2210 may include an optical output element such as an LED, bulb, laser, etc. The optical source(s) may be arranged in an array in some embodiments. As described in more detail in reference to FIG. 23 below, the emitter 2110 may include various other elements associated with the source 2210. The beam (or "light pipe") 2130 formed by the source(s) 2210 may be adjustable or configurable in various ways (e.g., power to the source may be varied, different numbers of sources may be activated, etc.).

The sensor 2220 may include various components that are able to sense the beam 2130. Such an output may represent a relative amount of sensed light expressed from a minimum value to a maximum value. Performance of the sensor 2220 may be configurable in various ways. For instance, some embodiments may allow parameters such as light sensitivity, gain, output range, input range, etc. to be modified depending on various appropriate criteria (e.g., test type, sample properties, practitioner or patient preferences, etc.).

The digitizer 2230 may receive the output signal generated by sensors 2220 and convert any analog outputs into digital signals. The digitizer 2230 and sensor 2220 may be combined into a single sensor element that generates a digital output signal. In some embodiments, for example, the sensor 2220 may produce an output between zero volts (no light sensed) to five volts (maximum light sensed, i.e., fluid path is clear). Such an output may be digitized to reflect values between zero and one thousand twenty-four (or other appropriate values, depending on available number of bits and capabilities of the sensing devices). The output of the digitizer 2230 may be used to determine a color density, depth, or saturation.

The filter 2240 may perform various processing operations on the digital output signal received from the digitizer 2230 or sensor 2220. Such processing may include, for instance, averaging or other smoothing, gain or other normalizing adjustments, color filtering or other signal processing, etc. The filtered output may be provided to a resource such as controller 1320.

The camera 2250 may be able to capture images or video associated with a portion of the fluid path 1920 that is illuminated by beam 2130 (and/or another appropriate resource). The UI interface 2260 may receive captured data from the camera 2250 and provide the data to a resource such as UI module 1350. The camera 2250 and UI interface 2260 may allow a patient or practitioner to monitor sample flow during a test.

FIG. 23 illustrates a schematic block diagram of various optical processing components associated with an optical measurement element 1610 in some embodiments. As shown, the optical measurement element may include a source 2210, a first optical filter 2310, and a second optical filter 2320.

In some embodiments, the source 2210 may radiate light over a range of output directions 2330. Filter 2310 may focus the beams 2330 into a single more powerful beam 2130 and/or otherwise manipulate the beams 2330 (e.g., by modifying the color of the beams). In some embodiments, the filter 2310 may be integrated into the housing of source 2210 or may be omitted. Some embodiments, as described below, may focus or filter the beam through an appropriately-sized opening in a portion of the cartridge 1910.

The filter 2320 may be similar to filter 2310. Some embodiments may omit one or bother filters 2310-2320. The output beam 2340 produced by filter 2310 may be provided to sensor 2220.

Different combinations of filters and/or other elements may be utilized to maximize contrast. For instance, when measuring red blood, some embodiments will utilize a light source 2210 and/or filter 2310 that produce a blue beam 2130. Continuing the blood example, filter 2320 may be a blue filter and the sensor 2220 may be specifically configured and/or selected to have peak sensitivity to light at the blue wavelength. Thus a clear fluid path 1920 would produce a very clear blue light pipe 2130 with maximum contrast versus a blood-filled portion of the fluid path 1920.

FIG. 24 illustrates a top plan view of a portion of a cartridge 1910 associated with an optical measurement element 1610 in some embodiments. FIG. 25 illustrates a side elevation view of a portion of a cartridge 1910 associated with an optical measurement element 1610 in some embodiments.

As shown, an area associated with optical element 1610 may include opaque or light-absorbing material 2410 (e.g., dark paint or other surface coating, embedded plastics, metals and/or other opaque elements, etc.). The light absorbing material may be applied to various surfaces of a cartridge 1910 (and/or other appropriate elements). In some embodiments, the material 2410 may be embedded into portions of the cartridge 1910.

Such material may reduce interference among multiple optical elements 1610 and/or other sources of light. The cartridge 1910 may include an opening (or "optical pathway") 2420 that is used to generate the light pipe 2130. In some embodiments, the opening 2420 may have a diameter of three millimeters. The size of the opening may be based at least partly on the size of the fluid pathway 1920 (e.g., the opening, and thus the light pipe, may be sized to have a slightly smaller diameter than the pathway). The opening may simply be an area with no opaque material 2410. In some embodiments, the opening 2420 may include a cavity or through-hole with opaque material 2410 lining the interior wall or surface of the cylinder 2420 along the portions that do not intersect the pathway 1920.

Some embodiments may include one or more light guides 2430. Such light guides may be located in a top plate 2440 and/or bottom plate 2450 of some embodiments. The top plate 2440 and bottom plate 2450 may be adjacent to the cartridge 1910 during operation. The source 2110 and absorber 2120 may be attached to PC boards that sit on the opposite sides of the plates 2440-2450 from cartridge 1910. Some embodiments may include a surround (e.g., a black plastic tube) that encloses either or both light guides 2430. Some embodiments may include one or more surrounds and omit one or more of the light guides. The light guides 2430, surrounds (not shown), light absorbing material 2410, and/or other elements may together form the "light pipe" 2130 of some embodiments.

One of ordinary skill in the art will recognize that the example architectures described above are exemplary in nature and different embodiments may be implemented in different specific ways without departing from the scope of the disclosure. For instance, various components may be combined or separated. As another example, various components may be distributed differently than shown (e.g., one or more pumps may be included in a disposable cartridge in some embodiments). As still another example, different embodiments may include different numbers of pumps, optical measurement elements, cavities, etc. Furthermore, different embodiments may be sized or shaped differently depending on the application. Such differences may include different layouts of internal components, circuitry, etc.

II. Methods of Operation

Figure 26:
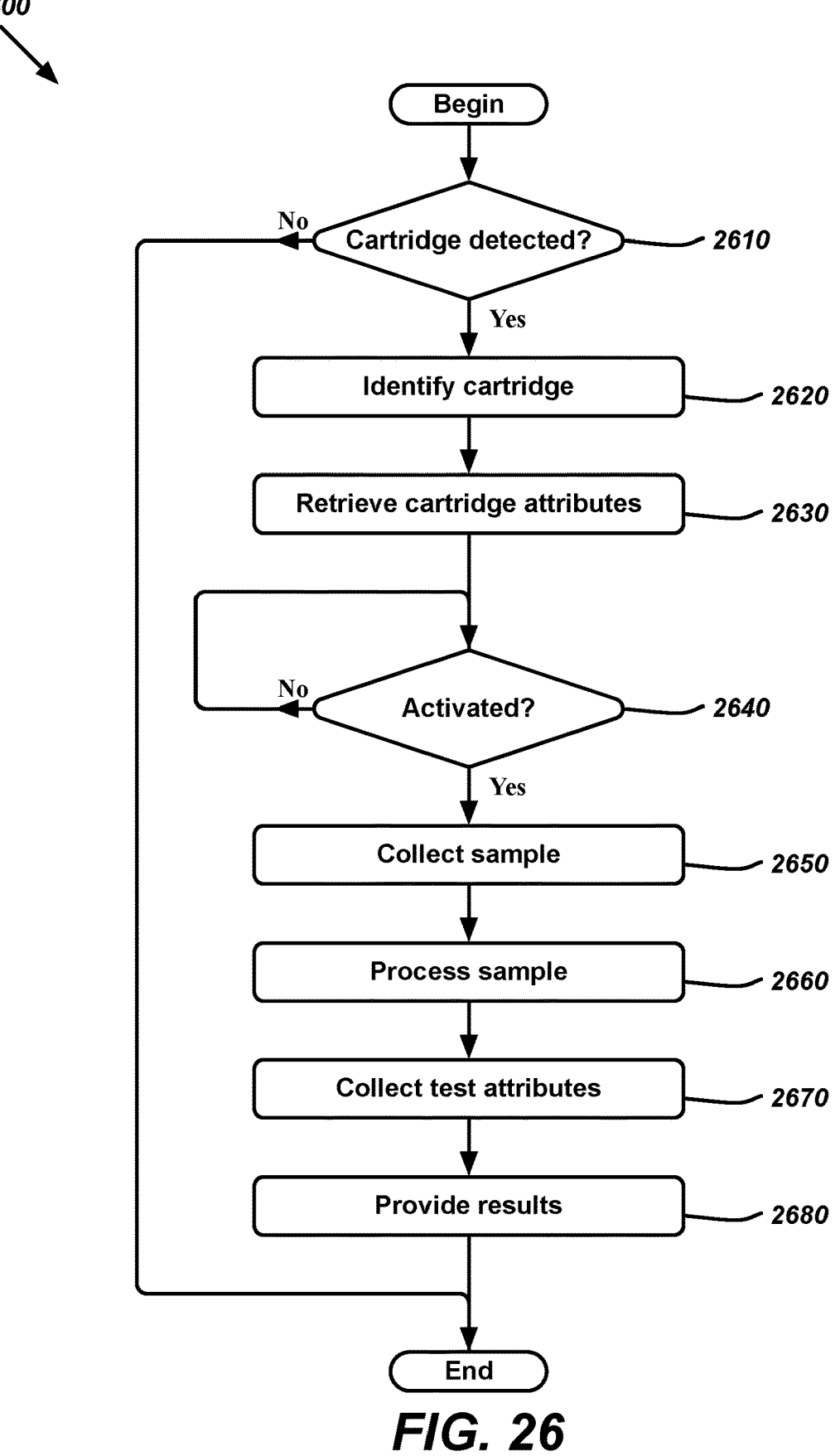
FIG. 26 illustrates a flow chart of an exemplary process that collects and tests a sample using the automated sample collection and testing device of FIG. 1.

FIG. 26 illustrates a flow chart of an exemplary process 2600 that collects and tests a sample using the automated SCTD 100. The process may begin when the device is powered on, when a sample processing module 110 is inserted, and/or other appropriate times.

As shown, the process may determine (at 2610) whether a cartridge is present. If the process determines that no cartridge is present, the process may end. If the process determines that a cartridge is present, the process may identify (at 2620) the cartridge. Such identification may include scanning of a graphic code, reading an RFID, receiving user input from an external device, etc.

Next, the process may retrieve (at 2630) cartridge attributes. Such attributes may be retrieved from the cartridge itself, from a local or remote database or look-up table, from user inputs, etc. The cartridge attributes may include, for instance, test type, fluid amounts (e.g., minimum sample volume), durations of operations (e.g., pulse counts associated with fluid measurements, reaction times, etc.), test or evaluation thresholds, etc.

The process may then determine (at 2640) whether the sample collection has been activated. Such a determination may be made based on various relevant factors, such as whether a finger (or other appropriate sample collection point) has been detected. Such a determination may be made using, for instance, the camera of some embodiments, a user input, a pressure sensor, etc.

If the process determines that no finger is detected, the process may continue trying to detect a finger until the process determines that a finger is detected. If the process determines that a finger is detected, the process may collect (at 2650) a sample. Such a sample may be collected using a needle and/or other appropriate elements as described above. Sample collection will be described in more detail in reference to process 2700 below.

Next, process 2600 may process (at 2660) the sample. Several example of such processing is described in more detail in reference to processes 3900-4100 below.

The process 2600 may then collect (at 2670) test attributes. Such attributes may include, for instance, charge difference at a pair of charge detectors, impedance or conductance of a sample (and/or processed sample), pH level, and/or any other measurable attribute of the fluid.

Next, the process may provide (at 2680) the results, and then may end. Such results may be based on comparison of the test attributes to one or more threshold values. The results may include discrete values (e.g., "pass", "fail", "inconclusive", etc.), measured values (e.g., weight or percentage of some tested parameter), and/or other appropriate result formats. The results may be provided via the SCTD 100 (e.g., using UI 120), a user device or medical device 1310, and/or other appropriate ways. Some embodiments may send the results (and/or measure or intermediate values) to multiple external devices or systems using an element such as communication module 1360.

Figure 27:
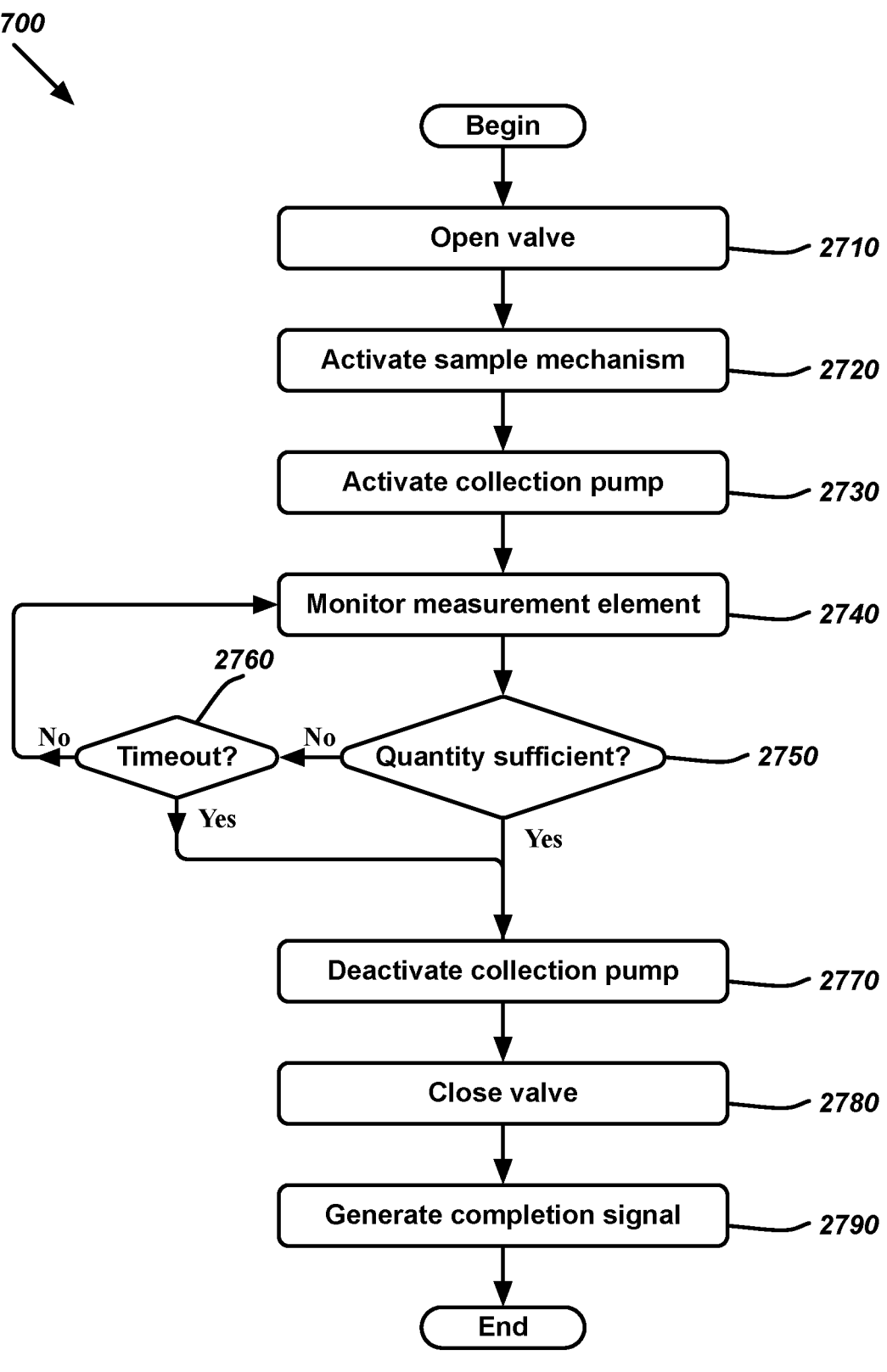
FIG. 27 illustrates a flow chart of an exemplary process that collects a sample using the automated sample collection and testing device of FIG. 1.

FIG. 27 illustrates a flow chart of an exemplary process 2700 that collects a sample using the automated SCTD 100. The process may begin when sample collection is activated as described in reference to operation 2640 above.

As shown, the process 2700 may open (at 2710) a valve such as pinch valve 320. Next, the process may activate (at 2720) a sample mechanism. Such a mechanism may include elements such as needle and spring 345, receptacle 340, and chip 325 described above. Activation of the sampling mechanism will be described in more detail in reference to process 2800 below.

Next, process 2700 may activate (at 2730) a collection pump, such as pump 315. The process may then monitor (at 2740) a measurement element such as element 1610 described above. Alternatively, some embodiments may monitor collection using a camera, scale, etc. Some embodiments may simply utilize a timer rather than attributes associated with the sample itself.

The process may then determine (at 2750) whether the collected quantity is sufficient for the associated test. Such a determination may be made based on various relevant factors (e.g., counter value, weight of sample, etc.).

If the process determines the quantity is not sufficient, the process may then determine (at 2760) whether a sample timeout has been exceeded. If the process determines (at 2760) that the sample timeout has not been exceeded, the process may repeat operations 2740-2760 until the process determines (at 2750) that the quantity is sufficient or the process determines (at 2760) that the timeout has been exceeded.

If the process determines (at 2750) that the quantity is sufficient, or if the process determines (at 2760) that the sample timeout has been exceeded, the process may deactivate (at 2770) the collection pump, close (at 2780) the valve, generate (at 2790) a completion signal, and then end. The completion signal may be an internal signal that is relayed to an element such as controller 1320 and may be used as a trigger to continue operations of process 2600 after collecting a sample at 2650. In some cases, no further processing may be performed after sample collection, and the completion signal may include indications at UI 120, via user device 1310, and/or other appropriate signals.

The automated sample collection process (drawing the sample, performing a test, measuring the results) may be completed in two minutes or less in most cases, thus allowing large-scale trials to be completed with less time spent collecting and testing samples and also reducing the amount of staff support needed to implement the trials.

In cases where the process determines (at 2760) that the timeout has been exceeded, the completion signal may indicate that the sample quantity is insufficient. Such a signal may cause the process to be re-run, or may provide a UI indication that the sample is insufficient and instruct the subject to insert another finger (or take other appropriate actions to successfully complete a sample collection, such as the insertion of a new cartridge).

FIG. 28 illustrates a flow chart of an exemplary process 2800 that controls a sampling element of the automated SCTD 100. The process may begin when sample collection is activated as described in reference to operation 2720 above.

As shown, process 2800 may retrieve (at 2810) sample collection parameters. Such parameters may include, for instance, balloon pressure, needle extension, etc.

Next, the process may activate (at 2810) a pump such as rubber pump 305 and monitor (at 2830) pressure at a retaining element such as balloon 310. Next, the process may determine (at 2840) whether the specified pressure (or other parameter) has been reached. The process may repeat operations 2830-2840 until the process determines (at 2840) that the specified pressure has been reached.

Next, the process may extend (at 2850) an actuator such as actuator 335, such that the needle 345 or other sampling element is extended. The actuator may be extended to a specified value or may be full extended and limited by physical features of the needle, actuator housing, stops, etc.

The process may then retract (at 2860) the actuator and determine (at 2870) whether the sampling is complete. Such a determination may be made in various appropriate ways. For instance, some embodiments may wait for a completion message as described above in reference to operation 2790. As another example, some embodiments may wait for a specified amount of time. As still another example, some embodiments may wait for a user input to be received via a UI element, user device, medical device, etc.

Some embodiments may extend the actuator using a two-step process to maximize comfort and efficiency. The process may first move the needle such that a microfluidic chip of some embodiments is pierced and the needle is "ready for sample". Next, the process may extend and retract the needle in order to generate the sample. Such an approach may optimize speed of movement of the lancet.

If the process determines (at 2870) that the sample is complete, the process may deactivate (at 2880) the rubber pump (and/or other retaining elements) and then may end.

Figure 29:
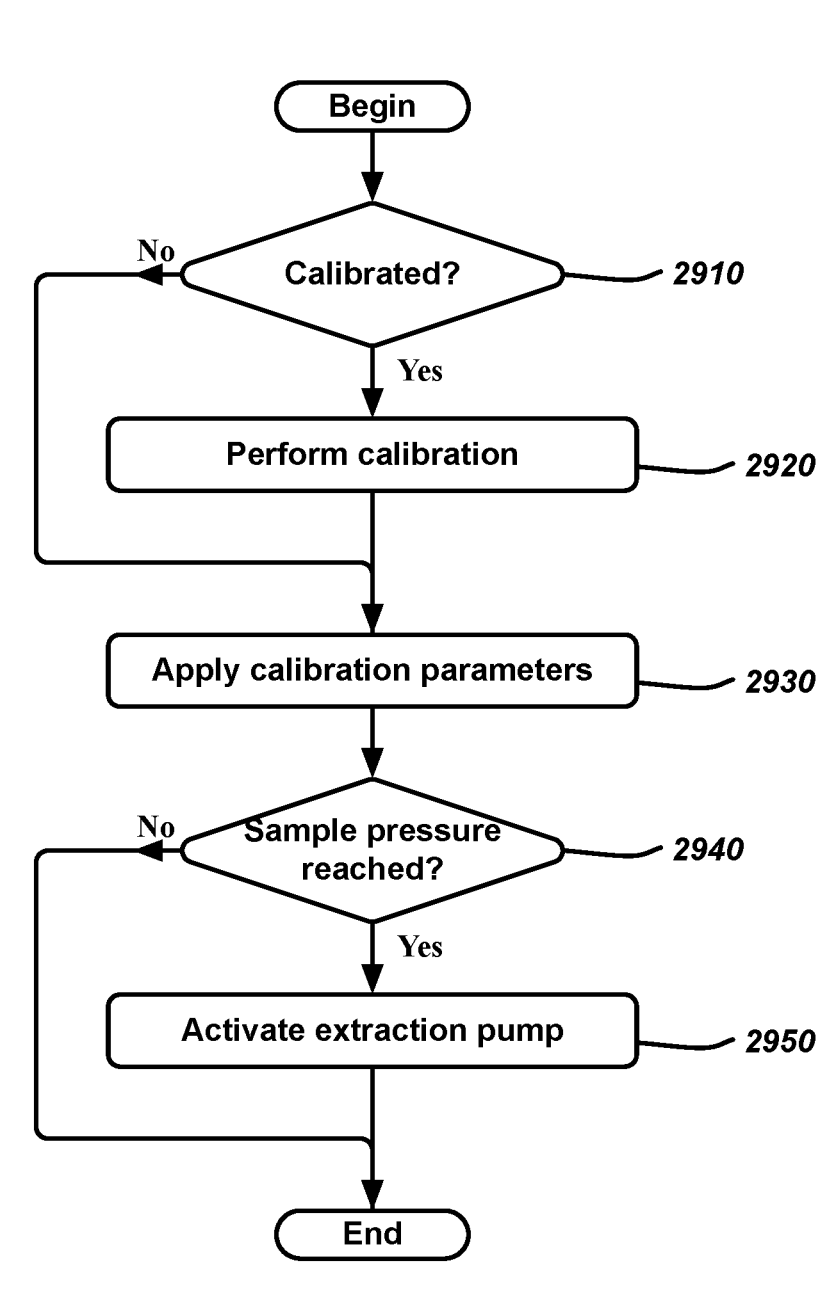
FIG. 29 illustrates a flow chart of another exemplary process that controls a sampling element of the automated sample collection and testing device of FIG. 1.

FIG. 29 illustrates a flow chart of another exemplary process 2900 that controls a sampling element of the automated SCTD 100. The process may begin when calibrating an SCTD for a particular test type and/or to engage additional suction power when collecting a sample. Process 2900 may be performed in serial or parallel with processes 2700 and/or 2800.

As shown, the process may determine (at 2910) whether an SCTD 100 has been calibrated. Such a determination may be made based on stored parameters, hardware settings, etc. If the process determines that the SCTD has not been calibrated, the process may then perform (at 2920) calibration.

Calibration may involve successively performing a lancet extension and retraction until a sample is generated. Feedback may be provided by a user, or the process may automatically determine when a sample is extracted (e.g., by monitoring an optical element of some embodiments in order to detect fluid flow), thus identifying an optimum sample depth. Alternatively, some embodiments may allow a user to specify a desired depth (or utilize a default depth). Calibration may be performed using a calibration cartridge. Such a cartridge may omit various included features, materials, etc. in order to reduce cost and waste. Some embodiments may be able to calibrate depth to a resolution of one hundred microns.

After determining (at 2910) that calibration has already been performed, or after performing (at 2920) calibration, the process may apply (at 2930) calibration parameters. Such parameters may include, for instance, depth, speed, duration, force, etc. Some embodiments may utilize default parameters when no user-specific and/or test-specific calibration parameters are available.

Next, during sample collection, the process may determine (at 2940) whether sufficient extraction pressure has been reached. Such a determination may be made based on various relevant criteria (e.g., sample pressure may be measured directly, fluid pathways may be monitored to determine if fluid is flowing from a collection point, etc.). If the process determines that there is not sufficient extraction pressure, the process may activate (at 2950) additional extraction pump(s).

For instance, in the example cartridge 110 of FIG. 18, multiple pumps 1830 may be activated in order to draw fluid from collection point 1810. As another example, flexible microfluidic chips such as chip 520 included in cartridge 500 may include an exhaust port (e.g., similar to port 1880) such that air (and/or other fluids) may be expelled when a sample fluid is collected. Such an exhaust port may be coupled to a pump that may be activated to supply additional extraction pressure. Some embodiments may couple a pump such as balloon pump 315 to the exhaust port.

After determining (at 2940) that the sample pressure has been reached or after activating (at 2950) the extraction pump(s), the process may end.

FIG. 30 illustrates a flow chart of an exemplary process 3000 that impels a small amount of fluid within the exemplary embodiments of the sample processing module 110. Such a process may be executed by the SCTD 100 using an optical element such as element 1610. The process may begin, for instance, when a sample is available or when a sample is being taken.

As shown, the process may retrieve (at 3010) a necessary (or minimum) sample volume. Such a volume may be retrieved from the cartridge, from a database or look-up table, received from a user, and/or other appropriate resource. The volume may be expressed as a count value or other discrete value associated with different measurement algorithms of different embodiments.

Next, the process may activate (at 3020) the appropriate pump associated with the measurement. Such a pump may be similar to pumps 315 or 1620-1635.

The process may then determine (at 3030) whether fluid is detected at the location of the flow pathway associated with the optical sensor 1610 (and/or other appropriate elements). Such detection may be based on detection of a leading edge 2170 such as that described above. The process may iteratively or continuously attempt to detect fluid until the process determines that fluid has been detected, at which point, the process may activate (at 3040) a counter or other timing algorithm.

Such a counter may be a digital and/or analog timer. In some embodiments, the counter may specify a duration during which the fluid is detected. In other embodiments, the counter may specify a number of pump motor pulses to be applied (or a duration during which pulses are applied). The counter may be incremented at regular intervals (e.g., each clock period) when used to measure duration of time.

In some embodiments, as described above, the sensor 1610 output may be converted to a digital or analog signal. In such cases, the signal may be analyzed in various appropriate ways in order to generate a "count" value (where such a value, in addition to being a literal counter or timer, may include any appropriate signal analysis). For instance, some embodiments may integrate the signal to calculate an area under a curve that may be used as the count value in order to determine a volume. As another example, the signal may be associated with various thresholds that may be used to activate or deactivate the counter (e.g., the counter value may increase when the signal is above a threshold and be held constant when the signal is below the threshold).

Next, the process may determine (at 3050) whether the sample is complete (i.e., whether the specified volume has been collected). Such a determination may be made based on whether a specified count threshold has been met or exceeded (and/or other appropriate analysis such as comparison of area to a threshold value).

If the process determines (at 3050) that the sample is not complete, the process may repeat operations 3040-3050 until the process determines (at 3050) that the sample is complete. In addition, the process may continue to monitor whether fluid is detected and may determine (at 3050) that the sample is complete when no more fluid is detected at the monitored portion of the fluid pathway. Such a determination may be made based on a gap in fluid detection having a minimum width or time duration, a sensor signal that drops below a specified threshold, etc.

If the process determines (at 3050) that the threshold volume has been collected, the process may stop (at 3060) the counter, deactivate (at 3070) the pump, send (at 3080) a completion message to other components or devices, and then may end.

Figure 31:
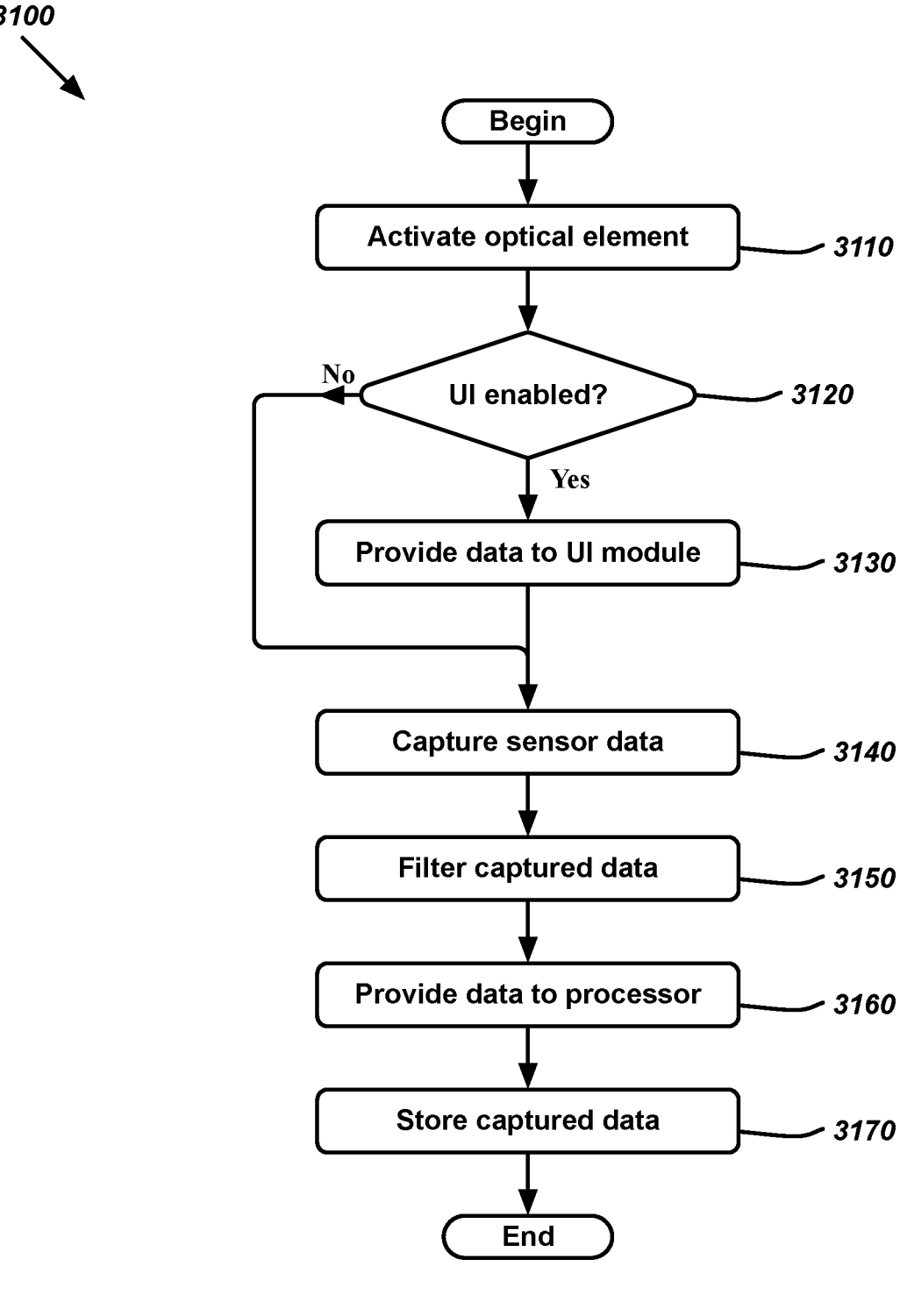
FIG. 31 illustrates a flow chart of an exemplary process that measures fluid parameters within the exemplary embodiments of the sample processing module included in the sample collection and testing device of FIG. 1.

FIG. 31 illustrates a flow chart of an exemplary process that measures fluid parameters within the exemplary embodiments of the sample processing module included in the sample collection and testing device 110. Such a process may be executed by the SCTD 100 using an optical element such as element 1610. The process may begin, for instance, when the SCTD 100 is powered on.

As shown, process 3100 may activate (at 3110) an optical element of some embodiments (e.g., element 1610). In addition, some embodiments may perform various calibration operations. Such operations could include, for instance, measuring absorber output with the emitter disabled, measuring absorber output with the emitter at maximum power and no cartridge inserted. As another example, some cartridges may include test fluids that may be used for calibration (e.g., a clear fluid and a red fluid) such fluids may be used only for calibration or may be associated with various substances used by the particular test cartridge (e.g., a blood thinner may be clear while an active agent may be dyed red).

Next, the process may determine (at 3120) whether the UI is enabled. Such a determination may be made based on various relevant factors (e.g., default parameters, test-specific parameters, user selections, etc.). If the UI is enabled, the process may capture data (e.g., using camera 1250) and provide (at 3130) the captured data to a UI module (e.g., by passing data from UI interface 1260 to UI module 1350). Photo or video data may then be displayed by the UI 120 of some embodiments.

After determining (at 3120) that the UI is not enabled, or after providing (at 3130) data to the UI module, process 3100 may capture (at 3140) sensor data using a resource such as sensor 1220. Such data may be digitized using an element such as digitizer 1230.

Next, the process may filter (at 3150) the captured data. Such filtering may include, for instance, averaging or other smoothing, gain or other normalizing adjustments, color filtering or other signal processing, etc. The filtering may be performed by a resource such as filter 1240.

Process 3100 may then provide (at 3160) the filtered captured data to a processor or other appropriate resource (e.g., controller 1320).

Finally, the process may store (at 3170) the captured data and then may end. Such data may be stored locally and/or transmitted to various other resources (e.g., user devices, servers, etc.).

In some embodiments, process 3100 may utilize feedback in order to optimize performance during a measurement operation. Such feedback may include, for instance, inputs received via UI 120 (e.g., a user may manually adjust gain or sensitivity). In some embodiments, the feedback may be generated automatically based on received data (e.g., if all measured values have fallen within a limited range, gain or sensitivity may be increased).

Some embodiments provide a test cartridge that includes an adjustable lancet (or needle). The adjustable lancet is controlled by a controller. The adjustable lancet automatically detects a subject's finger, adjusts the lancet's height, pricks the finger to draw blood, moves a tube to collect the blood, moves the tube away from the finger, and empties the blood from the tube into a vial or receptacle.

The adjustable lancet may include safety features to prevent the lancet to trigger when the subject's fingernail is facing the lancet, to control the amount that the lancet pierces the subject's finger, and/or to prevent the reuse of a test cartridge for multiple persons or multiple times by the same person. The adjustable lancet may include a massager wheel and/or a pressure bar to rub the subject's finger after the finger is pierced to facilitate drawing of the blood from the finger.

Figure 32:
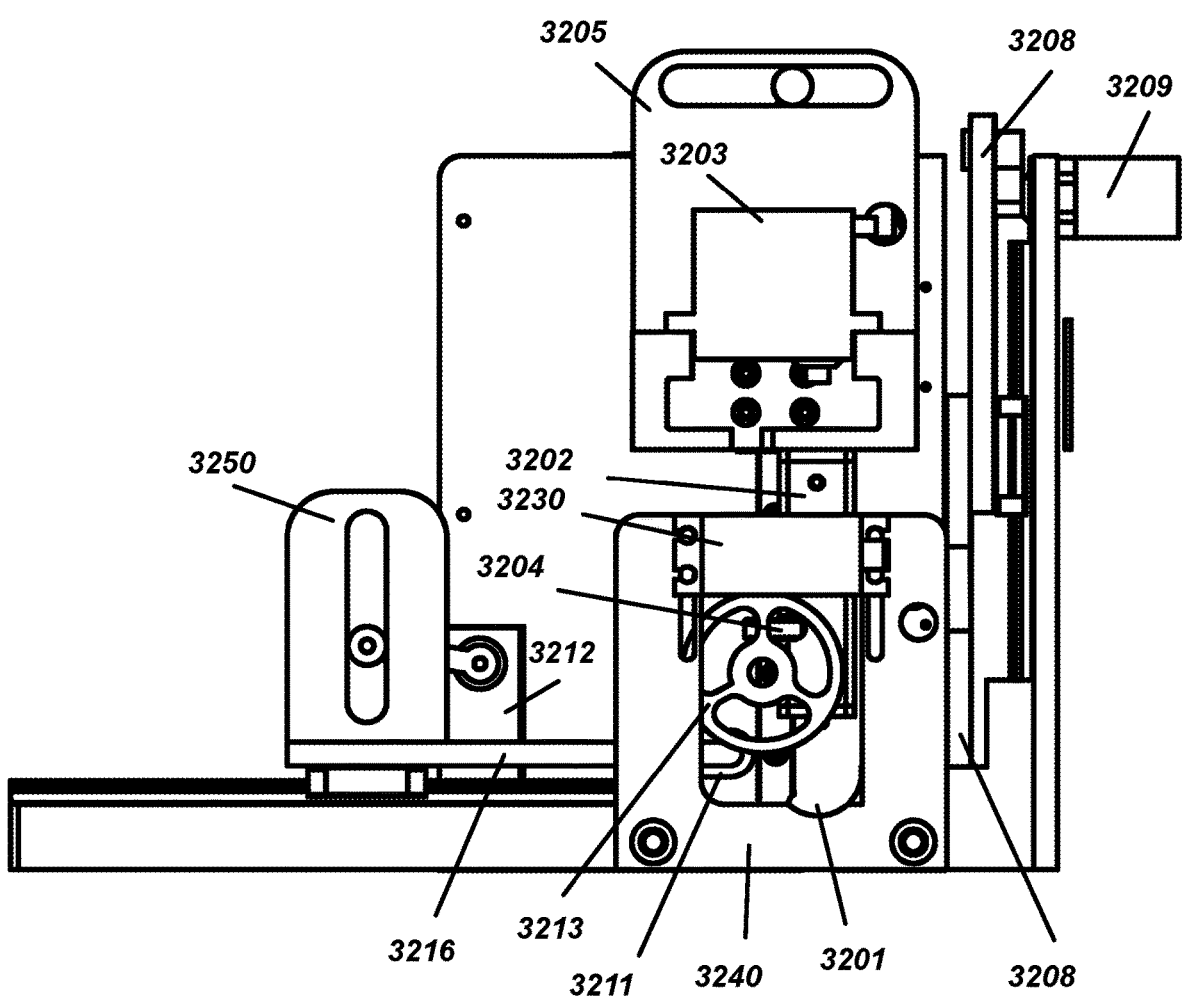
FIG. 32 illustrates a perspective view of an exemplary embodiment of an adjustable lancet assembly used by the sample collection and testing device of FIG. 1.
Figure 33:
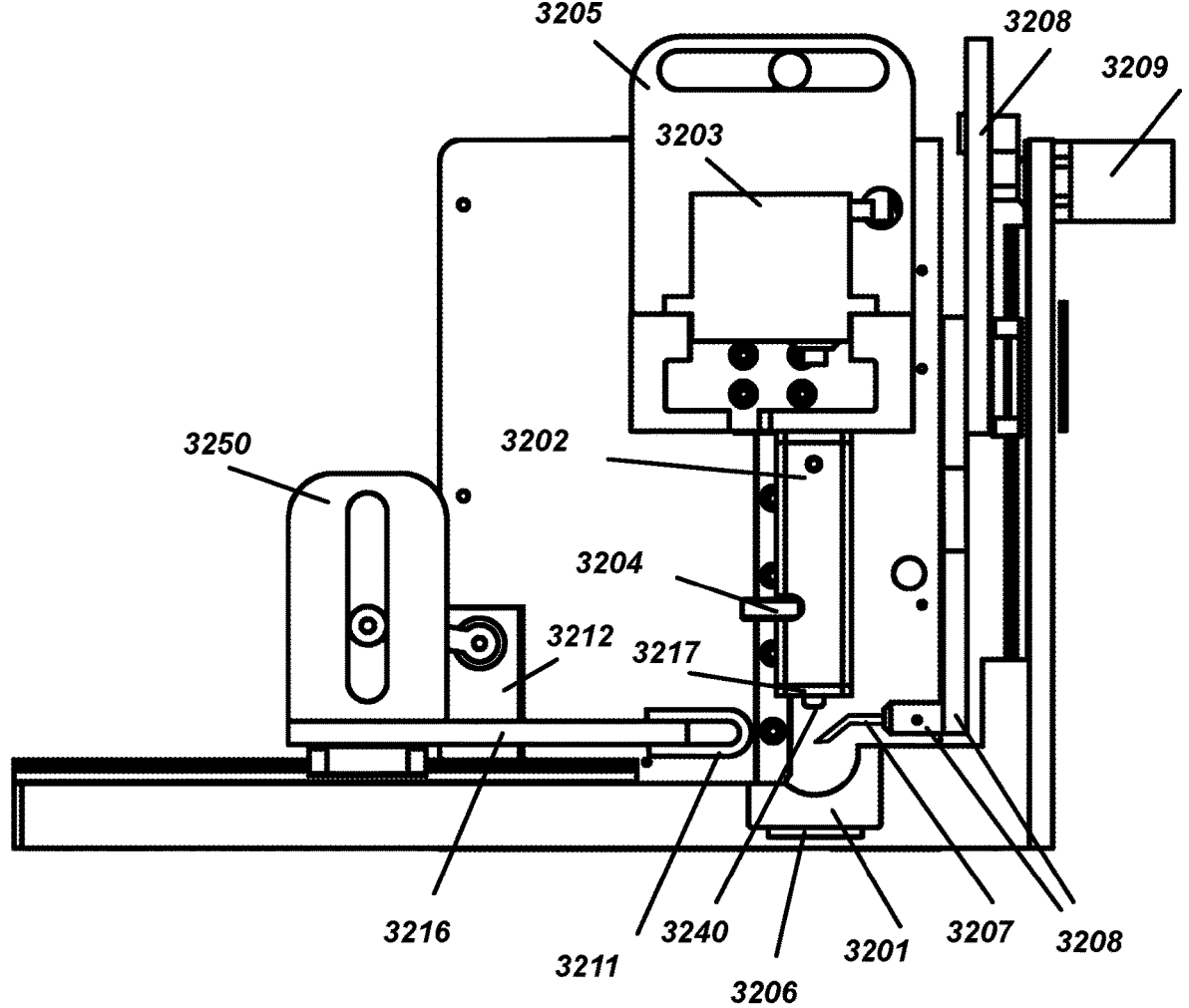
FIG. 33 illustrates a perspective view of the exemplary adjustable lancet assembly of FIG. 32 with the finger massager assembly removed.
Figure 34:
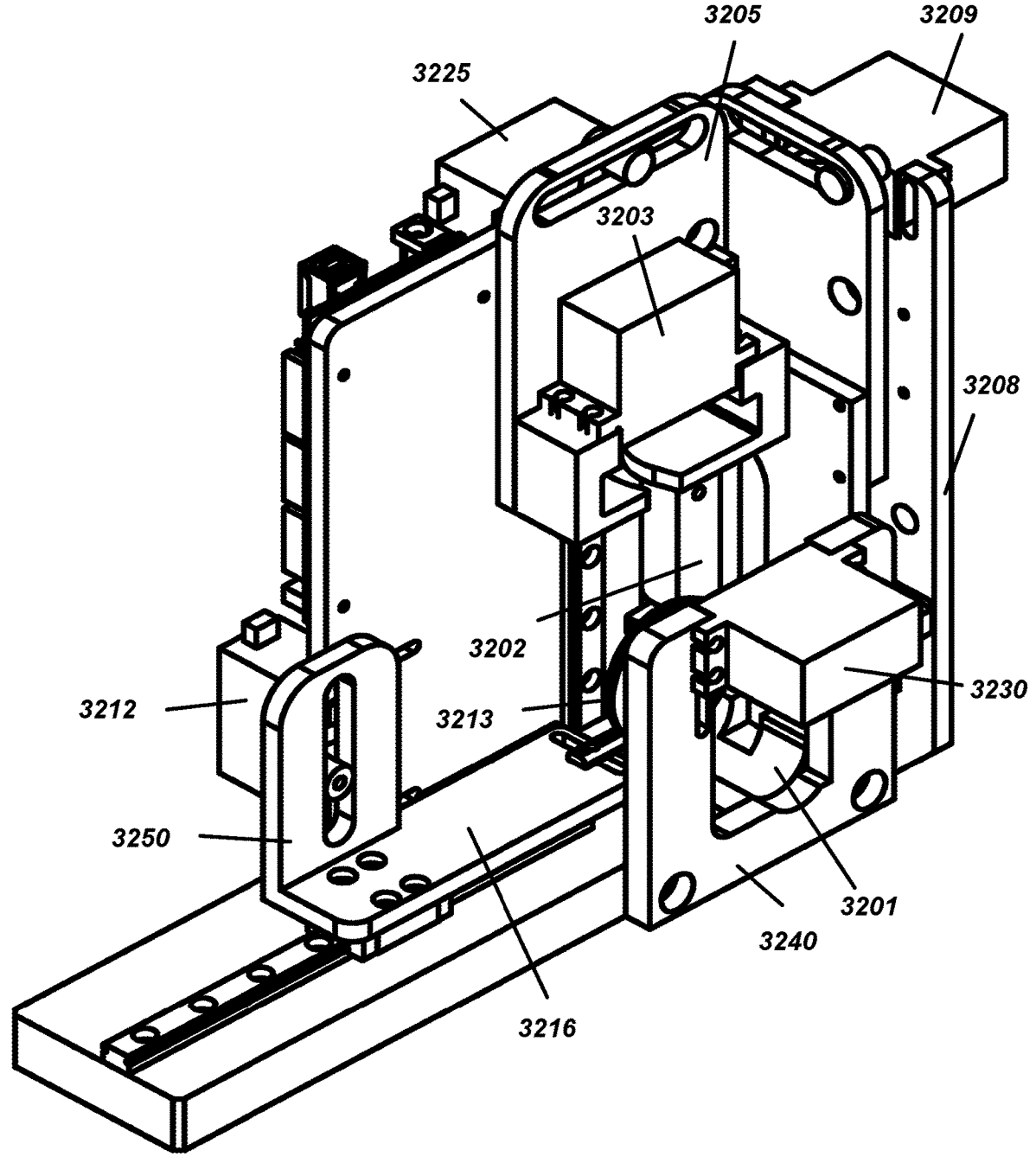
FIG. 34 illustrates a side elevation view of the exemplary adjustable lancet assembly of FIG. 32.
Figure 35:
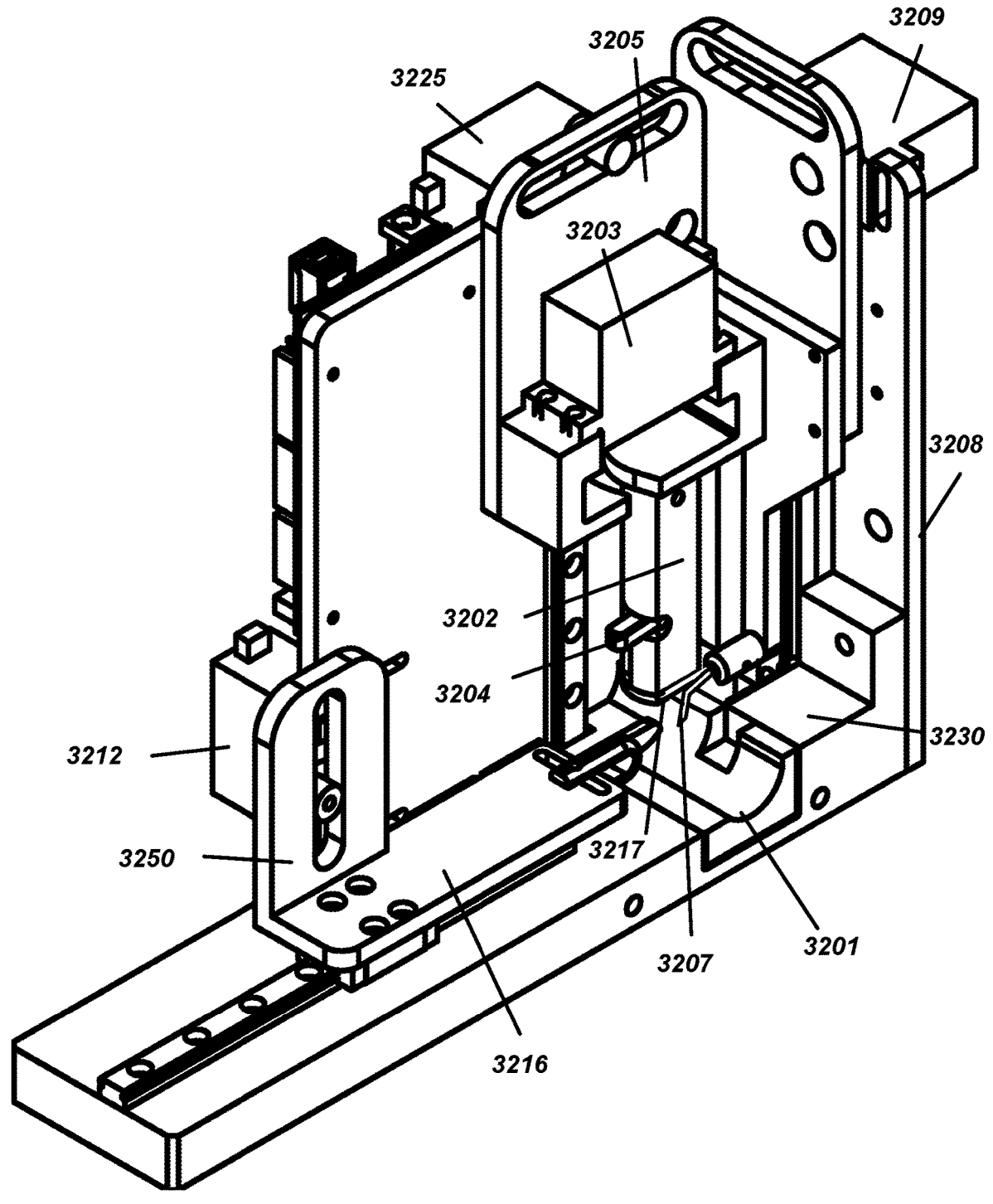
FIG. 35 illustrates a side elevation view of the exemplary adjustable lancet assembly of FIG. 33.

FIG. 32 illustrates a perspective view of an exemplary embodiment of an adjustable lancet assembly 3200 used by the sample collection and testing device of FIG. 1. FIG. 33 illustrates a perspective view of the exemplary adjustable lancet assembly 3200 of FIG. 32 with the massager 3213 and the plate 3240 holding the massager 3213 removed. FIG. 34 illustrates a side elevation view of the exemplary adjustable lancet assembly 3200 of FIG. 32. FIG. 35 illustrates a side elevation view of the exemplary adjustable lancet assembly 3200 of FIG. 32 with the massager wheel 3213 and the plate 3217 holding the massager wheel 3213 removed.

As shown in FIGS. 32-35, the adjustable lancet assembly 3200 may include a finger receptacle 3201, a lancet housing 3202, a servo motor 3225 for moving the lancet housing 3202, a trigger handle 3204 for releasing the lancet, a servo motor 3203 for releasing the trigger handle 3204, a movable plate 3205 connected to the lancet housing 3202 and the servo motor 3203, a force (or pressure) sensor 3206, a tube 3207 to pick up blood, a movable plate 3208 connected to the tube 3207, a servo motor 3209 that controls the movement of the plate 3208, a pump (not shown) connected to the end of the tube 3207, a pressure bar 3211, a servo motor 3212 the controls the movement of the pressure bar 3211, a finger massager wheel 3213, a servo motor (not shown) to move the tube 3207 forward and backward, one or more sensors and one or more light sources (shown in FIG. 36) to detect the fingernail, a handle 3216 connected to the pressure bar 3211, a lancet housing cap 3217, a plate 3240 connected to the massager wheel 3213, a servo motor 3225 to move the plate 3205 up and down, a servo motor 3230 to swing the massager wheel 3213, and a protrusion 3240.

Operation of the adjustable lancet may be controlled by a controller. The controller may be an electronic device that is able to execute instructions and/or process data. The controller may include a processor and may be able to at least partly direct the operations of the other components. The controller may be associated with a local memory (not shown) that is able to store instructions and/or data. The controller may be the same as the controller 1320 (FIG. 13) or the cartridge controller 1410 (FIG. 14) or may be a separate electronic device (not shown).

The finger receptacle 3201 is sized and shaped appropriately for a human finger. During operation, the finger is placed with the fingertip facing up towards the lancet housing 3202 and the fingernail facing down (in the pictured orientation). Some embodiments provide a safety mechanism that detects which side of the finger is facing the lancet. If it is the nail side is facing the lancet, the adjustable lancet's controller may generate an warning signal and may stop the operation of the adjustable lancet to prevent the possibility of the subject's fingernail being pierced by the lancet.

Figure 36:
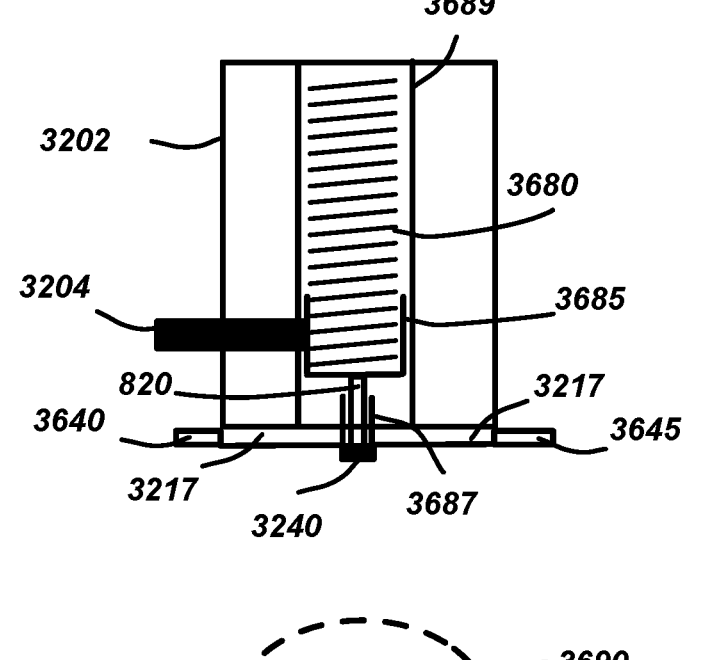
FIG. 36 illustrates a front elevation view of an exemplary embodiment of the finger receptacle and the lancet housing of FIGS. 32-35.

FIG. 36 illustrates a front elevation view of an exemplary embodiment of the finger receptacle 3201 and the lancet housing 3202 of FIGS. 32-35. The finger receptacle 3201 may have different shapes to accommodate different design goals. For example, the side 3670 may be longer than the side 3675 (as shown in FIGS. 32-35) to provide control the movements of the massager 3213, as described below.

The finger receptacle 3201 may include different mechanisms to ensure the subject's finger 3690 is placed on the finger receptacle 3201 with the fingertip facing the lancet. For example, in some embodiments, the side 3680 that touches the finger may be made of a transparent material such as, for example and without limitations, glass, clear plastic, etc. These embodiments may include one or more light sensors 3630 (e.g., photodetector(s)) and one or more light sources 3635 (e.g., LED light source(s), laser(s), bulb, and/or other optical components).

The light source(s) 3635 may direct light to the finger through the transparent side 3650 of the finger receptacle 3201. The light reflected from the finger is then sensed by the light sensor(s) 3630. The light that is reflected from a fingernail is different than the light reflected from the finger's skin. The sensed light may then be analyzed (e.g., by the adjustable lancet's controller) to determine whether the fingernail is facing down (opposite the lancet). Otherwise, the controller may generate a warning signal and stop the operation of the adjustable lancet.

The light sensor(s) and the light source(s) in different embodiments may be placed in different locations. For example, in addition to, or in lieu of the light sensor(s) 3630 and the light source(s) 3635, some embodiments may include the light sensor(s) 3640 and the light source(s) 3645 that are located on the lancet housing 3202 (e.g., on the lancet housing's body or lancet housing's cap 3217).

With reference to FIGS. 32-35, the adjustable lancet 3200 may include a force (or pressure) sensor 3206. The force sensor 3206, for example and without limitations, may be a force-sensing resistor that includes a material whose resistance changes when a force, pressure, or mechanical stress is applied to it. The force sensor 3206 may be communicatively coupled to the adjustable lancet's controller. Based on the changes in the value of the force sensor's resistance, the controller may determine whether a finger is placed on the finger receptacle 3201 (e.g., to activate the light source(s) 3635 and/or 3640).

The force sensor 3206 may also be used to determine whether the lancet housing 3202 (e.g., the protrusion 3240) has touched the finger. The lancet assembly located inside the lancet housing 3202 may include a spring 3680, a cap 3685, a channel (or groove) 3689, a guide 3687, and a lancet or needle 820. The lancet may be similar to the lancet 820 of FIG. 8. The lancet assembly may also include the trigger handle 3204, a cap 3217, and a protrusion 3240. The protrusion 3240 may be made of a material such as plastic, rubber, smooth metal and may slightly (e.g., and without limitations, 1-5 millimeters) project out of the cap 3217. The protrusion 3240 may include a hole (not shown) on its center to allow the lancet 820 to come out. The cup 3685 may be shaped and sized appropriately to move along channel 3689 such that lancet alignment is maintained through guide 3687.

During operation, the adjustable lancet's controller slowly moves the plate 3205 (FIGS. 32-35) down by controlling the corresponding servo motor 3225 (FIGS. 34-35). The lancet housing 3202 and the servo motor 3203 are connected to the plate 3205 and also move down. The force (or pressure) is continuously monitored by the force sensor 3206.

Figure 37:
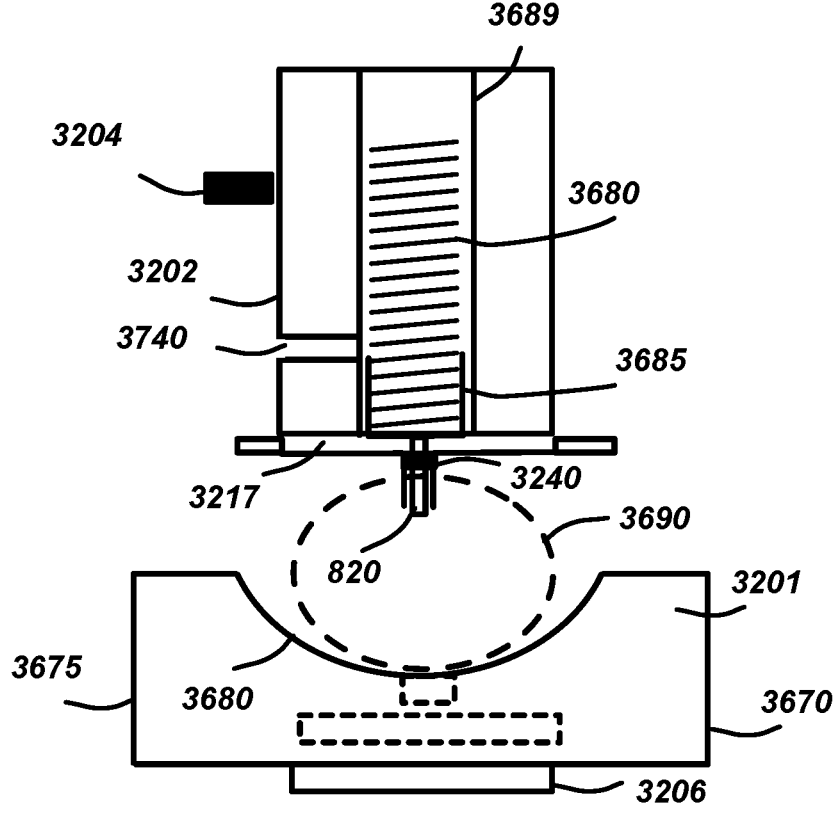
FIG. 37 illustrates a front elevation view of the exemplary embodiment of the finger receptacle and the lancet housing of FIG. 36 when the lancet housing is lowered to touch the subject's finger.

FIG. 37 illustrates a front elevation view of the exemplary embodiment of the finger receptacle 3201 and the lancet housing 3202 of FIG. 36 when the lancet housing 3202 is lowered such that the protrusion 3240 has touched the subject's finger 3690. Once the protrusion 3240 touches the finger 3690, the force (or pressure) reaches a predefined threshold, the controller stops the plate 3205. The controller may then move the plate 3205 back up by a small amount to relieve the protrusion's pressure from the subject's finger 3690. The amount the plate 3205 is moved up may be programmable in some embodiments.

The controller may then release the lancet 820. The lancet 820 may move out of the opening on the protrusion 3240 and prick the finger 3690. The lancet 820 is then automatically removed from the finger either automatically by a spring (not shown) or the controller may move the plate 3205 up and thereby move the lancet 820 and the lancet housing 3202 away from the finger.

The lancet 820 may be released by controlling the servo motor 3203 to release the trigger handle 3204. The spring 3680 may sit in the cup 3685 and may apply pressure to the cup 3685. The trigger handle 3204 (as shown in FIG. 36)

may sit in a slot 3740 (more clearly shown in FIG. 37) in the lancet housing 3202 and may prevent the cup 3685 to move down.

The controller may control the servo motor 3203 to move a handle (not shown) to move the trigger handle 3204 out of the slot 3740 (as shown in FIG. 37, in this example the trigger handle 3204 has rotated by approximately 90 degrees). Once the trigger handle is moved out of way, the spring 3680 may push the cup 3685 and the lancet 820 towards the finger 3690. With reference to FIG. 37, once the cup 3684 touches the cap 3217, the cap 3217 prevents the cup 3684 and the lancet 820 to move any further, thereby preventing the lancet 820 to penetrate the finger 3690 more than a predetermined amount.

With reference to FIGS. 32-35, once the finger is pricked, a certain amount of blood may come out of the fingertip. In order to facilitate drawing blood, the adjustable lancet 3200 may include a massager wheel 3213 and/or a pressure bar 3211. The massager wheel 3213 is shown in FIGS. 32 and 34 and is removed from FIGS. 33 and 35 in order to show the components that are behind the massager wheel 3213.

The massager wheel 3213 may be covered by a flexible material such as rubber, silicone, foam, plastic, etc., and may massages the fingertip in order to draw additional blood. The massager wheel 3213 may be connected to a shaft (not shown). The controller of the adjustable lancet 3200 may control the shaft by the servo motor (3230) to move the massager wheel 3213 like a pendulum (e.g., in a left to right direction in the pictured orientation).

The shaft keeps the massager wheel 3213 at a position where the massager wheel 3213 near the area that is pricked by the lancet. The location and the pendulum movement of the shaft is configured such that the massager wheel 3213 may touch the fingertip at a location close to where the finger is pricked. The flexible material on the massager wheel 3213 may deforms when it touches the finger in order to accommodate finger diameter of different persons.

With further reference to FIGS. 32-35, the pressure bar 3211 may be connected to a shaft 3216 and the shaft 3216 may be connected to the plate 3250. The plate 3250 and the shaft 3216 may be moved towards and away from the finger (e.g., in a left and right directions in the pictured orientation) by the servo motor 3212, which may be controlled by the adjustable lancet's controller. The pressure bar 3211 may be made of (or be covered by) a flexible material such as rubber, silicone, foam, plastic, etc., and may apply pressure to the side of the finger in order to draw additional blood. The operations of the massager wheel 3213 and/or the pressure bar 3211 may simulate massaging the finger of a subject by a person.

Once the massager wheel 3213 and the pressure bar 3211 are stopped, the tube 3207 may be moved to come in touch with the blood to collect the blood. The tube 3207 may be a capillary tube (e.g., and without limitation, a tube with a diameter of 0.5 millimeter to 3 millimeter) with an open end to touch the blood come out of the fingertip. The other end of the tube 3207 may be connected to a larger tube (not shown) made of silicone or other appropriate material. The larger tube may be connected to a pump (not shown) to facilitate drawing the blood in the tube 3207. The pump may be a bi-directional peristaltic pump similar to the pumps 1620-1635 of FIGS. 16-17 or the pumps 1830 of FIG. 18.

The tube 3207 may be made, for example and without limitations, of plastic, metal (e.g., steel), or other appropriate material. The tube 3207 may be connected to the plate 3208. The servo motor 3209 may be connected to the plate 3208 and may be controlled by the adjustable lancet's controller to move the tube up and down and side to side in the pictured orientation.

The controller may control the servo motor 3209 to move the tube 3207 down and another servo motor (not shown) to move the tube left (in the pictured orientation) towards the fingertip. At the same time, the controller may turn on the pump to run for a specified period of time to pick up the blood from the fingertip. The tube is moved to a position that is in line with the needle and where it pricks the finger. For example, the vertical plate where the lancet 820 (FIG. 37) may move and the distance 3670 that the lancet 820 may go down may be programmed into the controller and the controller may use this information to move the tube such that the open end of the tube 3207 comes in touch with the blood drawn out of the finger.

The pump may then be stopped and the tube may be moved back by the controller using the servo motor 3209 and the plate 3208. The open end of the tube 3207 may be moved into a vial or a receptacle (not shown) and the pump may be turned on in the reverse direction for a specified period of time to push the blood that is in the tube 3207 into the vial or receptacle. In some embodiments, the blood may be directly deposited in a microfluid system for example and without limitations, through a sample connection element 1605 (FIG. 16) instead of a vial or receptacle.

Using the massager wheel 3213 and/or the pressure bar 3211, moving of the tube, collecting of blood by the tube, reversing of the pump, and removing of the blood from the tube may be repeated several times to collect a certain amount of blood. In some embodiments, the pump may not be reversed and the desired amount of blood may be collected through the tube 3207 in a continuous operation.

The lancet housing 3202 and the components inside the lancet housing 3202 (e.g., the lancet 830, etc.), the tube 3207, the pressure bar 3211, the massager wheel 3213 may be disposable and may be included in a disposable cartridge. The housing of the cartridge is not shown in FIGS. 32-35 for simplicity. The location and sizes of different components of the adjustable lancet assembly may be different that the location and size of the components of FIGS. 32-35 in order to fit the disposable components in a disposable cartridge and/or to minimize the overall size of the adjustable lancet assembly and the SCTD.

The adjustable lancet 3200 may include a communication module such as the communication module 1510 of FIG. 15 that may provide NFC and/or other communication capabilities. The module may have an associated storage. Such elements may allow used cartridges to be "tagged" such that the cartridges are prevented from being used by multiple users or multiple times by the same user. The massager wheel 3213 and the pressure bar 3211, in some embodiments, may be replaceable. For example, massager wheel 3213 and the pressure bar 3211 may be clipped into their places and may be replaced with new massager wheel 3213 and the pressure bar 3211 for each different subject.

Some embodiments may provide a tray or container that may include many disposable test cartridges, each cartridge with a disposable adjustable lancet such as lancet 820 of FIGS. 32-37. In these embodiments, once taking blood sample from a subject is completed, the vial, receptacle, or microfluid system that has received the blood from the tube 3207 is electronically labelled with the subject's information (e.g., name, patient identification number, etc.) and the associated disposable cartridge is removed. The same process is then repeated from the next subject.

Figure 38A:
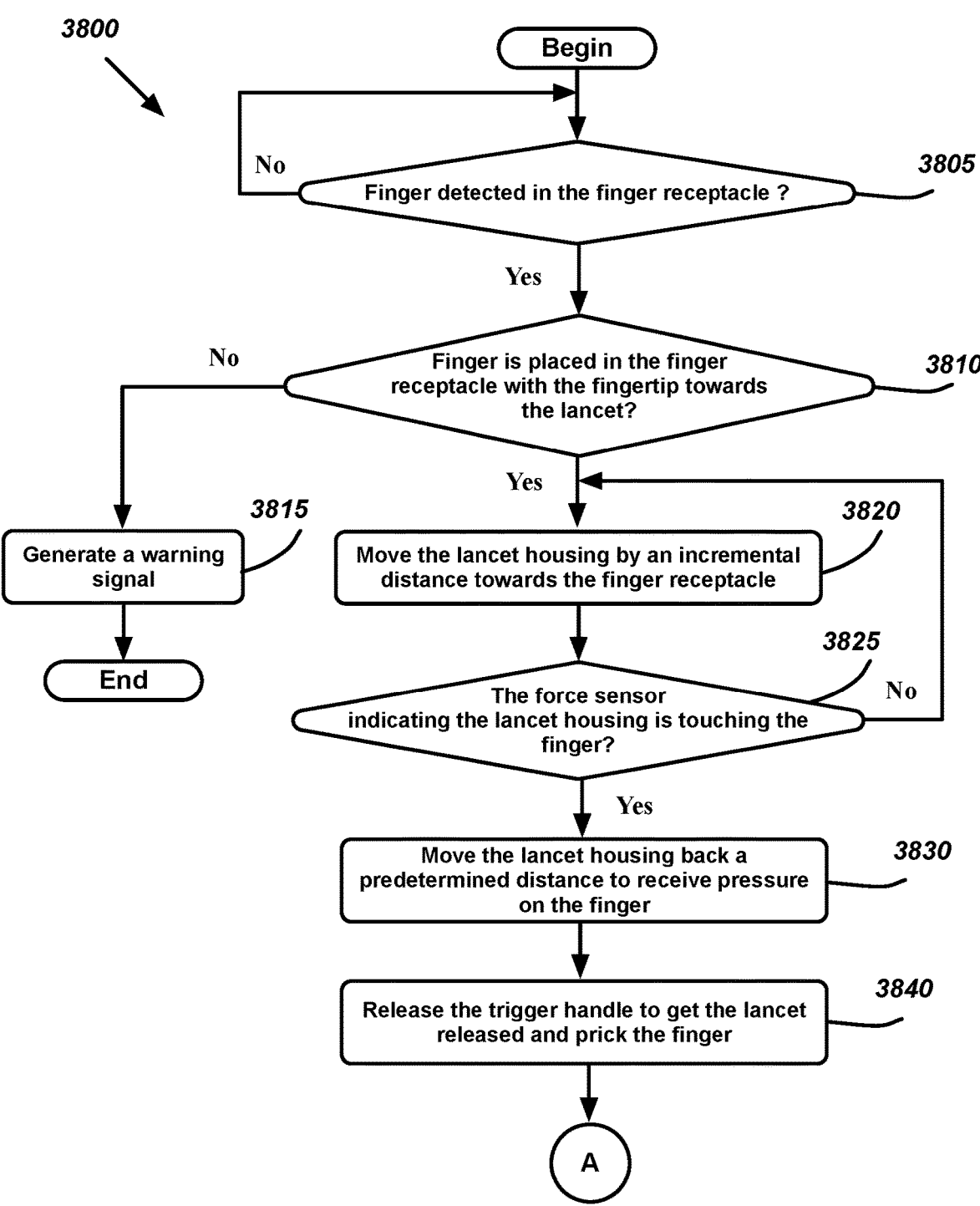
FIGS. 38A-38B illustrate a flow chart of an exemplary process that controls the adjustable lancet of FIGS. 32-37.
Figure 38B:
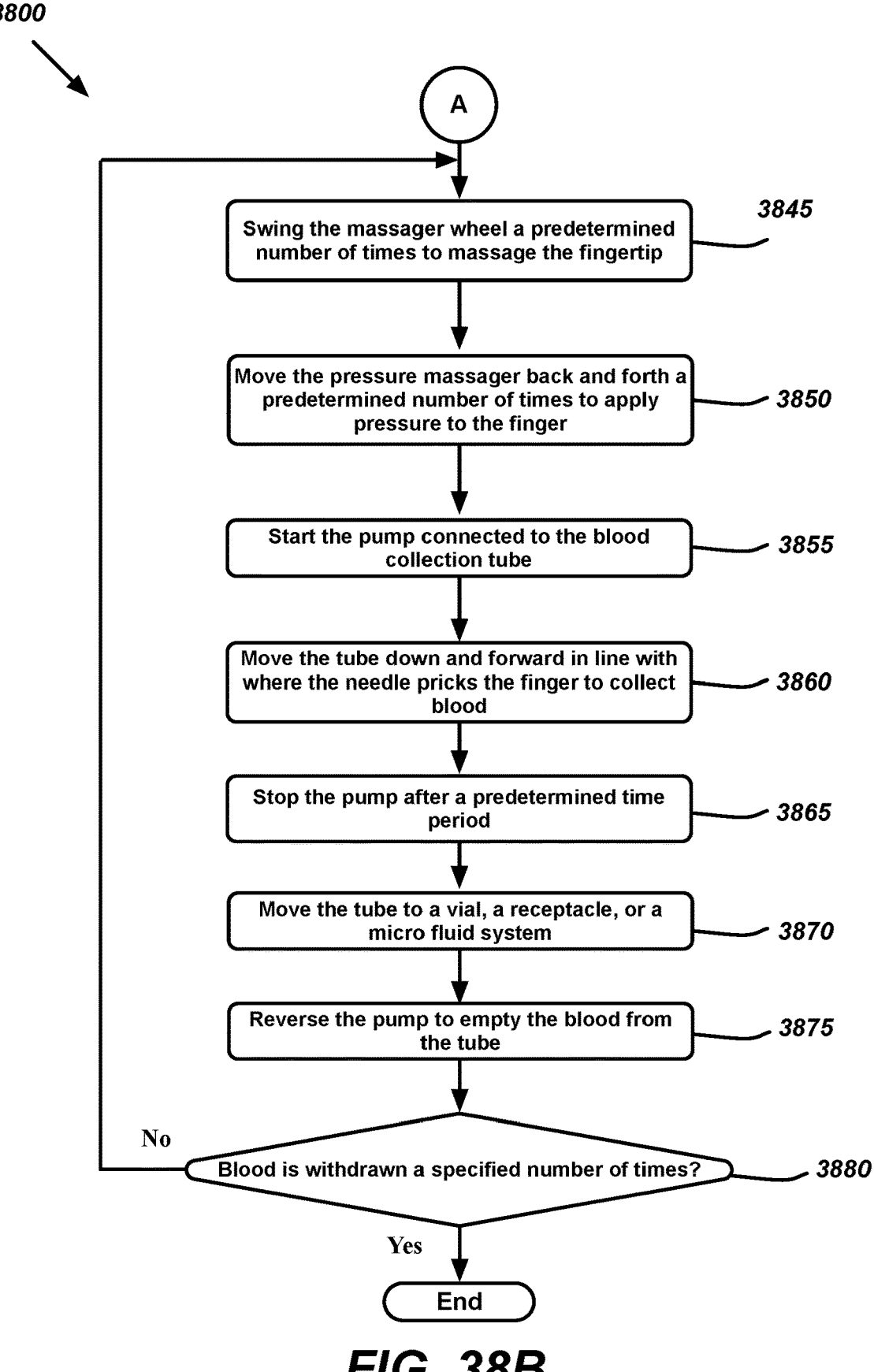

FIGS. 38A-38B illustrate a flow chart of an exemplary process 3800 that controls the adjustable lancet of FIGS. 32-37. Such a process may be executed by the SCTD 100. As shown, process 3800 may determine (at 3805) whether a finger is detected in the finger receptacle. For example, in some embodiments, the force sensor 3206 (FIG. 36) may detect an increase in the pressure applied to the force sensor 3206 by the finger receptacle 3201 when a subject's finger 3690 is placed in finger receptacle 3201. The process 3800 may compare an increase in the force measured by the force sensor with a range of increases in the force and determine that the measured increase in the force is attributed to a finger placed in the receptacle. In some other embodiments, the light source(s) 3635 and the light sensor(s) 3630 and/or the light source(s) 3640 and the light sensor(s) 3645 may be used to detect the finger. In some other embodiments, the process 3800 may receive a signal indicating a finger is in the finger receptacle when a button on the SCTD is pressed, when a signal is received from an external device, when power is received at the adjustable lancet assembly, etc.

When a finger is not detected, the process 3800 may return to 3805 and may repeat the operation 3805 until a finger is detected. Otherwise, the process 3800 may determine (at 3810) whether the finger is placed in the finger receptacle with the fingertip towards the lancet. For example, the process may use the light source(s) 3635 and the light sensor(s) 3630 and/or the light source(s) 3640 and the light sensor(s) 3645 of FIG. 36 to determine whether the fingertip is toward the lancet (and the fingernail is away from the lancet). As described above with reference to FIG. 36, the light source(s) may direct light to the finger and the light reflected from the finger is then sensed by the light sensor(s). The sensed light may then be analyzed to determine whether the fingernail is facing opposite the lancet.

When the finger is not placed in the receptacle with the fingertip towards the lancet, the process 3800 may generate (at 3815) a warning signal. The process 3800 may then end. The warning signal may be either a visual signal (e.g., a light turned on or off, a message displayed on a UI associated with the SCTD 100, etc.), may be an audible signal, may be an electronic signal sent to a device outside the SCTD 100, etc.

When the finger is placed in the receptacle with the fingertip towards the lancet, the process 3800 may move (at 3820) the lancet housing by an incremental distance towards the finger receptacle. The process 3800 may then determine (at 3825) whether the force sensor (e.g., the force sensor 3206 of FIGS. 36-37) has indicated the lancet housing is touching the finger. For example, the process 3800 may determine that the lancet housing's protrusion 3240 is touching the finger 3690 based on the increase in the resistance of the force sensor caused by the force excreted by the lancet housing 3202 to the finger 3690 and by the force excreted by the finger 3690 to the receptacle 3201. The process 3800 may compare the increase in the force measured by the force sensor with a range of increases in the force and determine that the measured increase in the force is attributed to the lancet housing touching the finger.

When the process 3800 determines that lancet housing is not touching the finger, the process 3800 may return to 3820, which was described above. Otherwise, the process 3800 may move (at 3830) the lancet housing back a predetermined distance (e.g., a few millimeters) to relieve the pressure on the finger. The process 3800 may then release (at 3840) the trigger handle (e.g., the trigger handle 3204) to get the lancet 820 released and prick the finger.

The process 3800 may then swing (at 3845) the massager wheel (e.g., the massager wheel 3213) a predetermined number of times to massage the fingertip to draw additional blood. The process 3800 may also move (at 3850) the pressure bar (e.g., the pressure bar 3211) back and forth a predetermined number of times to apply pressure to the finger to draw additional blood.

The process 3800 may then start (at 3855) the pump connected to the blood collection tube (e.g., the tube 3207). The process 3800 may then move (at 3860) the tube down and forward in line with where the needle pricks the finger to collect blood. The process 3800 may then stop (at 3865) the pump after a predetermined time period.

The process 3800 may then move (at 3870) the tube to a vial, a fluid receptacle, or a microfluid system. The process 3800 may then reverse (at 3875) the pump to empty the blood from the tube into the vial, the receptacle, or the microfluid system. The process 3800 may then determine (at 3880) whether the blood is withdrawn a specified number of times. If not, the process 3800 may proceed to 3845 to repeat operations 3845-3880. Otherwise, the process 3800 may end. In the embodiments that the blood is drawn from the tube in a continuous operation, operation 3880 may be skipped.

Figure 39:
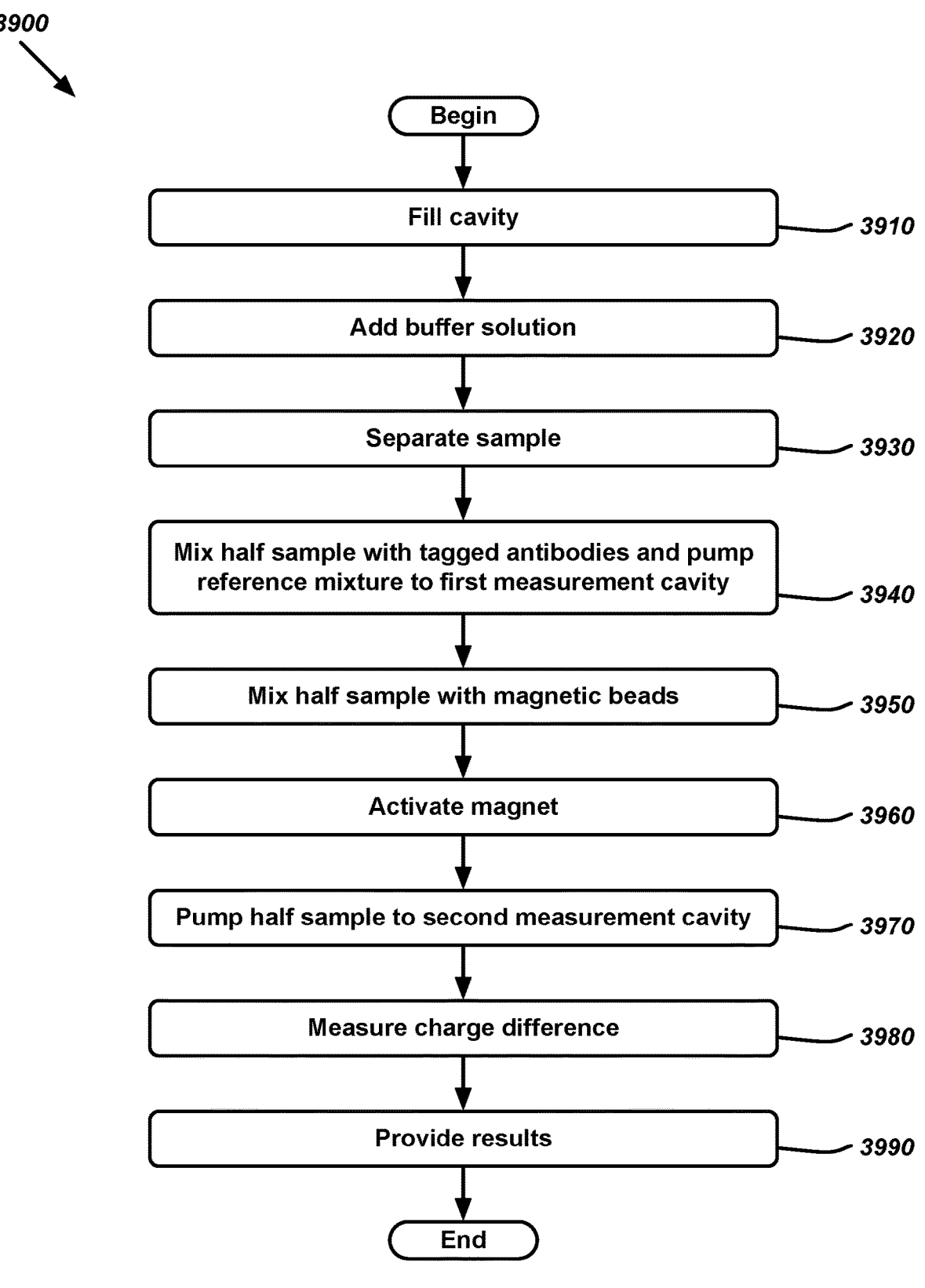
FIG. 39 illustrates a flow chart of an exemplary process that processes a sample using the sample processing module of FIG. 16.

FIG. 39 illustrates a flow chart of an exemplary process 3900 that processes a sample using the sample processing module 110 of FIG. 16. Such a process may be executed by the SCTD 100. The process may begin after a sample is taken, such as described above in reference to operation 2650 and process 2700.

As shown, process 3900 may fill (at 3910) a first cavity (e.g., cavity 1640). Such a cavity may be filled using a first pump (e.g., pump 1620) and a first optical sensor (e.g., sensor 1610) to provide a specified amount of fluid to the cavity (e.g., cavity 1640). Some embodiments may apply one thousand pulses, for example, to the pump in order to move one microliter of blood, with an accuracy of approximately one nanoliter.

In some embodiments, the optical sensor (e.g., sensor 1610) may be placed before a pump (e.g., pump 1620) such that when fluid is detected at the optical sensor, a stepper motor of the pump may be operated for a number of pulses in order to move a defined amount of fluid. Such sensor placement may result in improved accuracy by eliminating additional fluid that may be retained past the pump and later pulled into the associated cavity.

Next, the process may add (at 3920) a buffer solution. The buffer solution may be stored in a second cavity (e.g., cavity 1645) and moved into the first cavity using a second pump (e.g., pump 1625). The second pump may then be reversed and the mixture moved into the second cavity. Such operations may be performed over multiple iterations to thoroughly mix the solution.

The process may then separate (at 3930) the sample into halves (and/or other portion ratios). A third pump (e.g., pump 1630) and second optical sensor (e.g., sensor 1635) may be used to accurately measure the appropriate amount of fluid (whether half or some other ratio) and move that amount into a third cavity (e.g., cavity 1650), while retaining a reference sample in the second cavity. The process may mix (at 3940) that sample with the contents of the third cavity. The third cavity may include electrically charged (and/or otherwise tagged) HAAH antibodies (or any other appropriate antibody).

In addition, the second pump may be used to pump (at 3940) the reference half sample in the second cavity to the first measurement cavity (e.g., cavity 1640). The third pump may move the mixture in the third cavity between the third cavity and the second cavity to thoroughly mix the solution.

At this point, any HAAH molecules in the blood sample will attach to the HAAH antibodies (or the target molecules will attach to other types of charged antibodies).

After mixing (at 3940) the sample with the antibodies, some embodiments may wait for a specified time to allow proper mixing of the sample and the antibody to take place. The wait time may vary depending on various relevant factors (e.g., test type, temperature, accuracy needed, etc.). The wait time may be a programmable parameter of the SCTD 100.

Next, the process may mix (at 3950) the half sample in the third cavity with the content of a fourth cavity (e.g., cavity 1655) using a fourth pump (e.g., pump 1635). The fourth cavity may include HAAH and magnetic beads that attach to any leftover HAAH antibodies that have not been attached to HAAH molecules in the blood.

The process may then activate (at 3960) the electromagnet. Next, the process may use the fourth pump to move (at 3970) the contents of the third cavity to the fourth cavity (or second measurement cavity), excluding the contents that are retained in the third cavity by the electromagnet.

The process may then measure (at 3980) the charge difference between the charge of the first cavity and the charge of the fourth cavity. The difference is proportional to the density of HAAH in the blood and may be provided as the final output of the process. After providing (at 3990) the results of the charge difference measurement, the process may end.

In addition, the results and/or other parameters (e.g., optical measurement waveforms, count values, subject information, test parameters, etc.) may be stored for future reference and analysis.

HAAH molecules (and HAAH antibodies) are described as one example only. Other embodiments may utilize various other antibodies such that the density of any target molecules in a sample may be determined.

Figure 40:
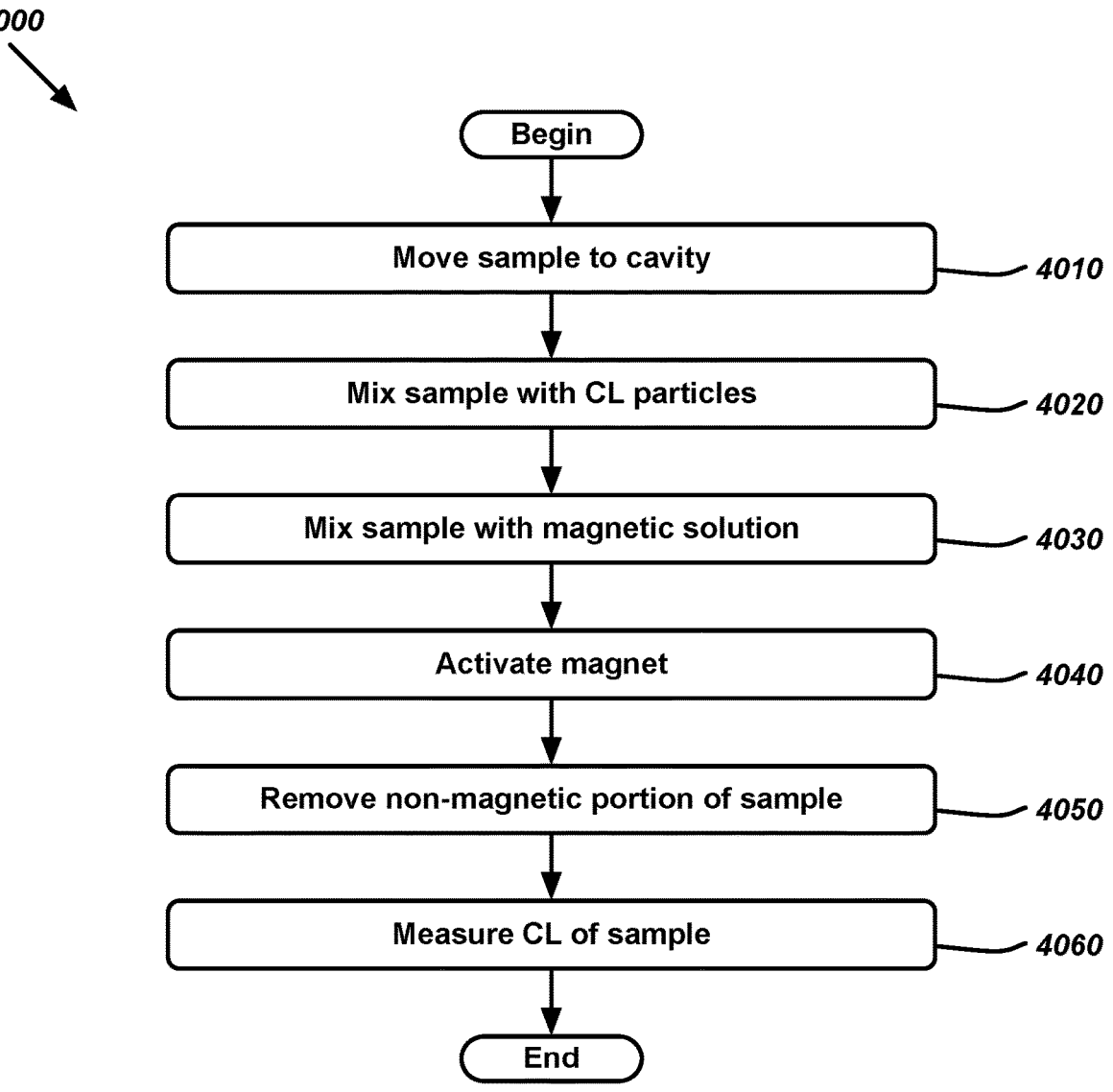
FIG. 40 illustrates a flow chart of an exemplary process that processes a sample using the sample processing module of FIG. 17.

FIG. 40 illustrates a flow chart of an exemplary process 4000 that processes a sample using the sample processing module of FIG. 17. Such a process may be executed by the SCTD 100. The process may begin after a sample is taken, such as described above in reference to operation 2650 and process 2700.

As shown, process 4000 may move (at 4010) the sample to a first cavity such as cavity 1640. Such a sample may be collected via sample collection element 1605 and pump 1620. The operations of the pump may be at least partly controlled based on data provided from a measurement element such as element 1610. The first cavity may be pre-filled with a buffer solution.

Next, the process may mix (at 4020) the sample and buffer solution with a CL agent attached to an antibody (e.g., CL attached to HAAH antibody). A second cavity, such as cavity 1645, may be pre-filled with such antibodies. A pump such as pump 1625 may be used to mix the contents of the first and second cavities by moving the mixture between the cavities several times.

The process may then mix (at 4030) the sample with the complementary molecule attached to magnetic beads such as those described above (e.g., HAAH protein attached to magnetic beads). A third cavity (e.g., cavity 1650) may be pre-filled with such a solution and the sample may be mixed using pump 1630 to move the mixture between the second and third cavities.

Next, the process may activate (at 4040) the electromagnet (e.g., magnet 1660) and then remove (at 4050) the non-magnetic portion of the sample mixture. The non-magnetic portion may be removed using pump 1630, for instance, such that the non-magnetic portion (which includes the bound CL agents and antibodies) may be retained in the second cavity.

Finally, the process may measure (at 4060) the CL of the mixture in the second cavity and then may end. Such a measurement may be made using a detector such as detector 1700 described above. The measurement may be provided to various appropriate resources, such as a processor, user device, etc. Likewise, the measurement may be provided by a UI 120 of some embodiments.

Figure 41:
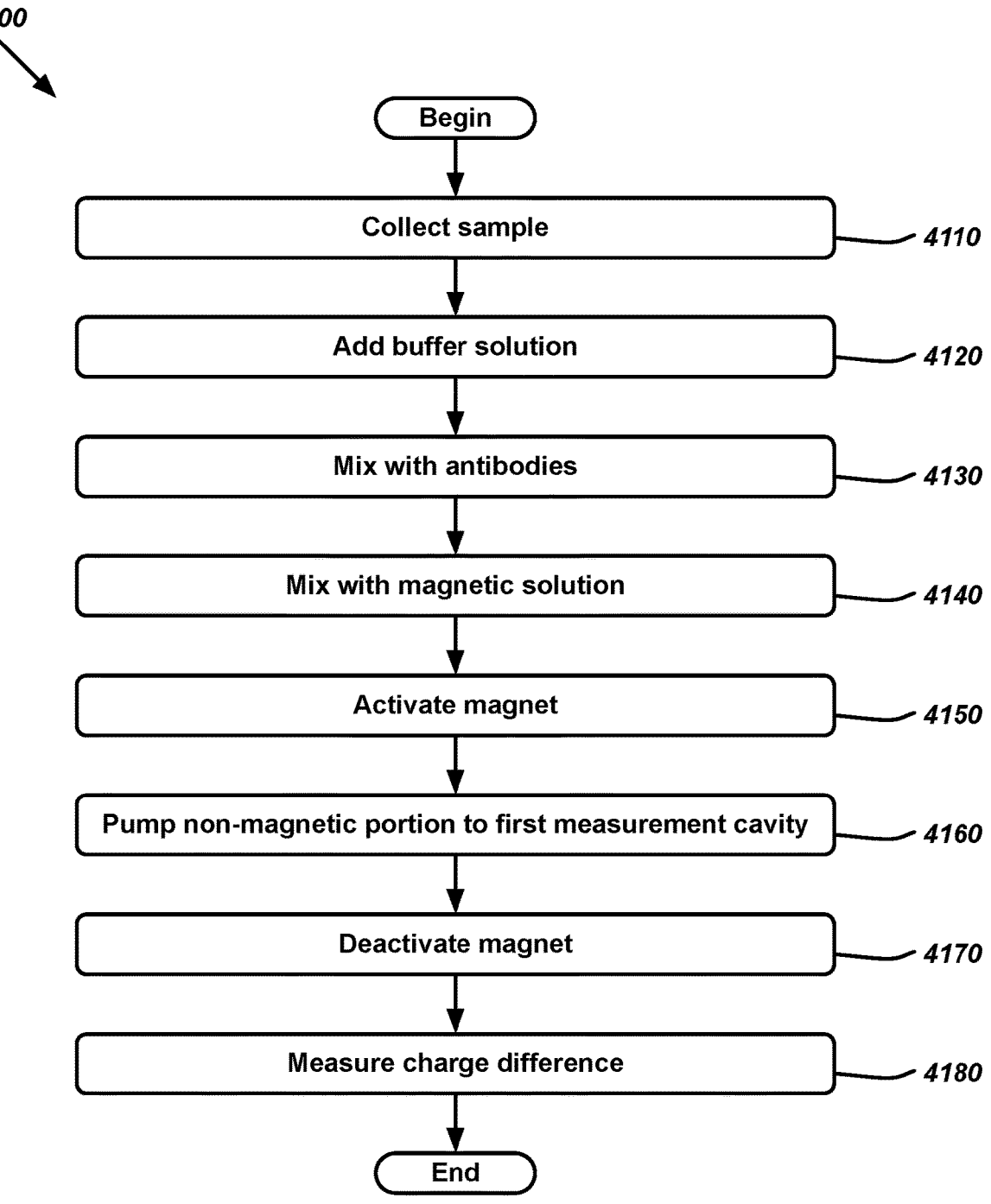
FIG. 41 illustrates a flow chart of an exemplary process that processes a sample using the sample processing module of FIG. 18.

FIG. 41 illustrates a flow chart of an exemplary process 4100 that processes a sample using the sample processing module 110 of FIG. 18. Such a process may be executed by the SCTD 100. The process may begin after a sample is taken, such as described above in reference to operation 2650 and process 2700.

As shown, process 4100 may collect (at 4110) a sample. Such a sample may be collected via sample collection element 1810 using a first pump 1830, first and second measurement elements 1820, and a first cavity (C1) 1840.

Next, the process may add (at 4120) a buffer solution to the sample. The buffer solution may be moved to the first cavity (C1) 1840 using a second pump 1830, third and fourth measurement elements 1820, and a pre-filled cavity (BS) 1850. As above, the solution may be moved between cavity (BS) and cavity (C1) several times to thoroughly mix the solution. Some portion of the mixture (usually 50%) may be retained in some embodiments (e.g., within cavity (C1)) for future analysis.

The process may then mix (at 4130) the mixture with electrically charged antibodies by moving a portion (usually 50%) of the contents of cavity (C1) to cavity (C2) while also moving the contents of cavity (AB) into cavity (C2) as well. The pre-filled cavity (AB) may include such antibodies, which may be mixed with the mixture of cavity (C1). The mixing of such elements may be performed using a combination of the pumps 1830, where some pumps may act as valves at any given time while one or more pumps may be used to move the contents of various cavities along the fluid pathway to other cavities.

Next, the process may mix (at 4140) the mixture in cavity (C2) with a certain agent or protein (e.g., HAAH protein) attached to magnetic beads. Pre-filled cavity (MB) may include such a magnetic solution. The mixture may be retained in cavity (C2). The process may then activate (at 4150) the electromagnet 1870 such that the magnetic beads (and associated particles) are retained in the cavity (C2).

Process 4100 may then pump (at 4160) the non-magnetic portion of the mixture in cavity (C2) to a third measurement cavity (C3). Next, the process may deactivate (at 4170) the magnet.

Finally, the process may measure (at 4180) the charge difference between the first measurement cavity (C1) and the third measurement cavity (C3) and then may end. Alternatively, different embodiments may perform various other measurements (e.g., charge, impedance or conductance, pH level, color or other visual attributes, and/or any other measurable attribute of the fluid).

The measured value may be provided to various appropriate resources, such as a processor 1320, user device 1310, etc.

One of ordinary skill in the art will recognize that processes 2600-4100 are exemplary in nature and different embodiments may perform such processes in various different ways. For instance, the various operations may be performed in different orders. As another example, some embodiments may include additional operations and/or omit various operations. Further, some embodiments may divide the processes into multiple sub-processes and/or combine multiple processes into a macro process. Some operations, and/or sets of operations may be performed iteratively, and/or based on some criteria other than those described above.

III. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 42:
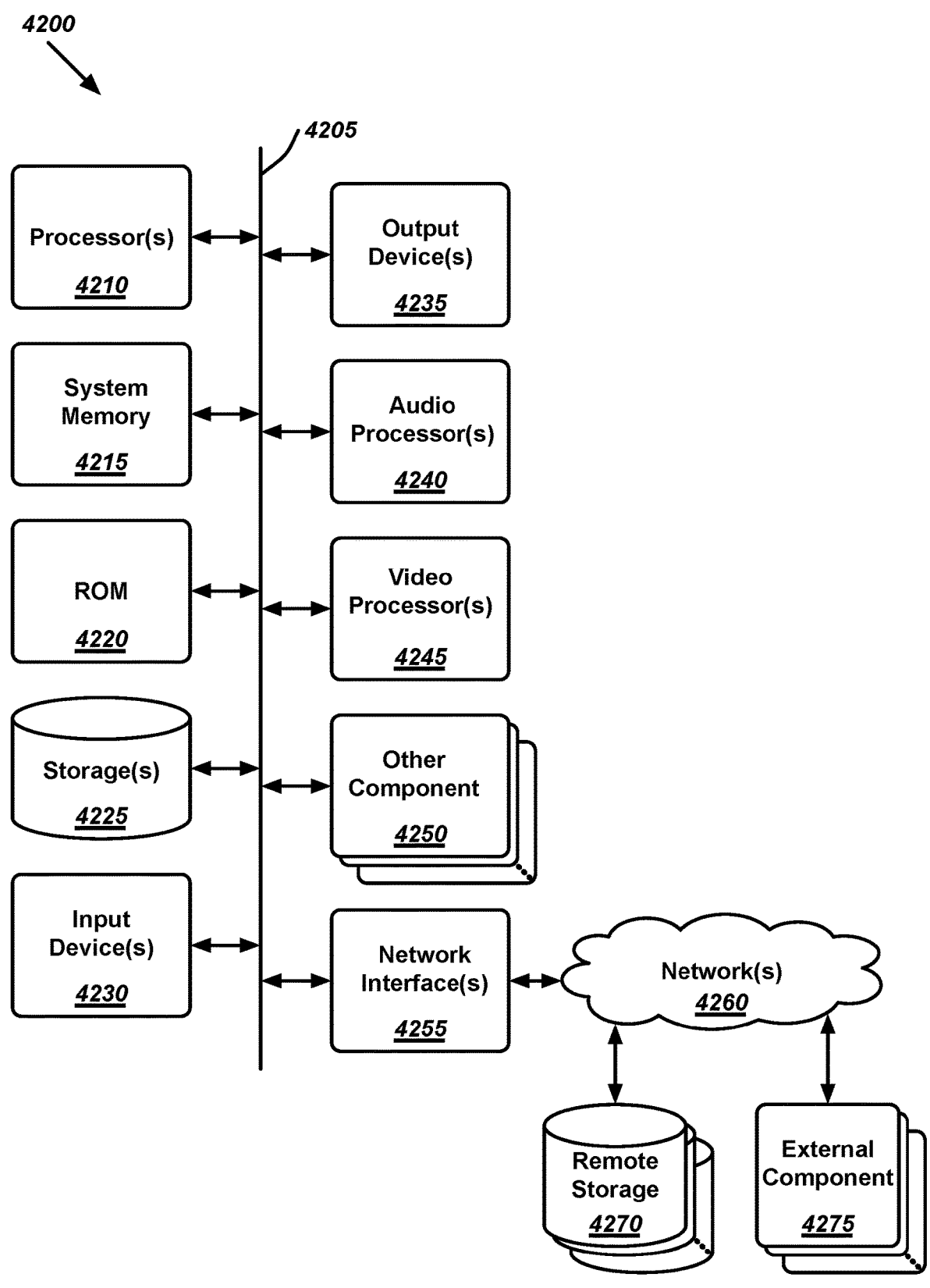
FIG. 42 illustrates a schematic block diagram of an exemplary computer system used to implement some embodiments.

FIG. 42 illustrates a schematic block diagram of an exemplary computer system 4200 used to implement some embodiments. For example, the system and devices described above in reference to FIG. 1-FIG. 25 may be at least partially implemented using computer system 4200. As another example, the processes described in reference to FIG. 26-FIG. 41 may be at least partially implemented using sets of instructions that are executed using computer system 4200.

Computer system 4200 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 4200 may include at least one communication bus 4205, one or more processors 4210, a system memory 4215, a read-only memory (ROM) 4220, permanent storage devices 4225, input devices 4230, output devices 4235, audio processors 4240, video processors 4245, various other components 4250, and one or more network interfaces 4255.

Bus 4205 represents all communication pathways among the elements of computer system 4200. Such pathways may include wired, wireless, optical, and/or other appropriate communication pathways. For example, input devices 4230 and/or output devices 4235 may be coupled to the system 4200 using a wireless connection protocol or system.

The processor 4210 may, in order to execute the processes of some embodiments, retrieve instructions to execute and/or data to process from components such as system memory 4215, ROM 4220, and permanent storage device 4225. Such instructions and data may be passed over bus 4205.

System memory 4215 may be a volatile read-and-write memory, such as a random access memory (RAM). The system memory may store some of the instructions and data that the processor uses at runtime. The sets of instructions and/or data used to implement some embodiments may be stored in the system memory 4215, the permanent storage device 4225, and/or the read-only memory 4220. ROM 4220 may store static data and instructions that may be used by processor 4210 and/or other elements of the computer system.

Permanent storage device 4225 may be a read-and-write memory device. The permanent storage device may be a non-volatile memory unit that stores instructions and data even when computer system 4200 is off or unpowered. Computer system 4200 may use a removable storage device and/or a remote storage device as the permanent storage device.

Input devices 4230 may enable a user to communicate information to the computer system and/or manipulate various operations of the system. The input devices may include keyboards, cursor control devices, audio input devices and/ or video input devices. Output devices 4235 may include printers, displays, audio devices, etc. Some or all of the input and/or output devices may be wirelessly or optically connected to the computer system 4200.

Audio processor 4240 may process and/or generate audio data and/or instructions. The audio processor may be able to receive audio data from an input device 4230 such as a microphone. The audio processor 4240 may be able to provide audio data to output devices 4240 such as a set of speakers. The audio data may include digital information and/or analog signals. The audio processor 4240 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 4245 (or graphics processing unit) may process and/or generate video data and/or instructions. The video processor may be able to receive video data from an input device 4230 such as a camera. The video processor 4245 may be able to provide video data to an output device 4240 such as a display. The video data may include digital information and/or analog signals. The video processor 4245 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 4250 may perform various other functions including providing storage, interfacing with external systems or components, etc.

Finally, as shown in FIG. 42, computer system 4200 may include one or more network interfaces 4255 that are able to connect to one or more networks 4260. For example, computer system 4200 may be coupled to a web server on the Internet such that a web browser executing on computer system 4200 may interact with the web server as a user interacts with an interface that operates in the web browser. Computer system 4200 may be able to access one or more remote storages 4270 and one or more external components 4275 through the network interface 4255 and network 4260. The network interface(s) 4255 may include one or more application programming interfaces (APIs) that may allow the computer system 4200 to access remote systems and/or storages and also may allow remote systems and/or storages to access computer system 4200 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

Each of the processes described herein, including the processes 2600, 2700, 2800, 2900, 3000, 3100, 3800, 3900, 4000, and 4100 are illustrated as a collection of blocks in a logical flow graph, which represent a sequence of operations that may be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks may be combined in any order and/or in parallel to implement the processes. Additionally, any number of the described blocks may be optional and eliminated to implement the processes.

It should be recognized by one of ordinary skill in the art that any or all of the components of computer system 4200 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

What is claimed is:

1. A sample collection and testing device, comprising:
   a processor;
   a lancet;
   a lancet housing encompassing the lancet;
   a massager wheel;
   a first shaft connected to the massager wheel;
   a pressure bar; and
   a second shaft connected to the pressure bar;
   wherein the processor is configured to:
      move the lancet housing by an incremental distance;
      determine that the lancet housing has not touched the finger of the person;
      repeat the moving of the lancet housing by the incremental distance until determining that the lancet housing has touched the finger; and
      move the lancet housing away from the finger by a predetermined distance to relieve pressure on the finger;
      trigger the lancet to prick a finger of a person;
      swing, after triggering the lancet, the first shaft in a pendulum like movement to make one or more contacts between the massager wheel and the finger at a location close to an area on the finger that is pricked by the lancet; and move the second shaft toward and away from the finger one or more times to apply pressure to a side of the finger.

2. The sample collection and testing device of claim 1 further comprising:

a servo motor, wherein the processor is configured to control the first shaft by the servomotor.

3. The sample collection and testing device of claim 1, wherein a location of the first shaft and the pendulum like movement of the first shaft are configured such that the massager wheel touches the finger at a location close to where the finger is pricked.

4. The sample collection and testing device of claim 1, wherein the first shaft is configured to keep the massager wheel at a position where the massager wheel is near an area of the finger that is pricked by the lancet.

5. The sample collection and testing device of claim 1, wherein the massager wheel is covered with a flexible material comprising one of a rubber, silicone, foam, and plastic.

6. The sample collection and testing device of claim 5, wherein the flexible material is configured to deform to accommodate finger sizes of different persons.

7. The sample collection and testing device of claim 1 further comprising:

a servo motor, wherein the processor is configured to control the second shaft using the servomotor.

8. The sample collection and testing device of claim 1, wherein the pressure bar is covered with a flexible material comprising one of rubber, silicone, foam, and plastic.

9. The sample collection and testing device of claim 1, wherein the processor is configured to move the lancet away from the finger prior to moving the second shaft back and forth one or more times to apply pressure to a side of the finger.

10. The sample collection and testing device of claim 1, wherein the lancet, the massager wheel, and the pressure bar are in a disposable cartridge, and wherein the processor is reusable for a plurality of disposable cartridges.

11. The sample collection and testing device of claim 1, wherein the processor is configured to move the lancet away from the finger prior to swinging the first shaft to make the one or more contacts between the massager wheel and the finger.

12. The sample collection and testing device of claim 1 further comprising:

a tube; and a pump configured to cause blood to move in or out of the tube;

wherein the processor is configured to:

move the tube to touch the finger at a location in a vicinity of where the lancet pricks the finger; and start the pump to pull in blood from the finger into the tube.

13. The sample collection and testing device of claim 12, wherein the processor is configured to:

stop the pump a period of time after starting the pump; and move the tube away from the finger.

14. The sample collection and testing device of claim 12, wherein the processor is configured to:

move the tube to a receiving device; and start the pump in a reverse direction to empty the blood from the tube into the receiving device.

15. An automated method of massaging a finger after a lancet of a sample collection and testing device pricks the finger, the sample collection and testing device comprising a lancet housing encompassing the lancet, a massager wheel, a first shaft connected to the massager wheel, a pressure bar, and a second shaft connected to the pressure bar, the method comprising:

by a processor of the sample collection and testing device:

moving the lancet housing by an incremental distance;

determining that the lancet housing has not touched the finger of the person;

repeating the moving of the lancet housing by the incremental distance until determining that the lancet housing has touched the finger;

moving the lancet housing away from the finger by a predetermined distance to relieve pressure on the finger;

triggering the lancet to prick a finger of a person;

after triggering the lancet, swinging the first shaft in a pendulum like movement to make one or more contacts between the massager wheel and the finger at a location close to an area on the finger that is pricked by the lancet; and moving the second shaft toward and away from the finger one or more times to apply pressure to a side of the finger.

16. The automated method of claim 15 further comprising moving the lancet away from the finger by the processor of the sample collection and testing device prior to swinging the first shaft to make the one or more contacts between the massager wheel and the finger.

17. The automated method of claim 15 further comprising moving the lancet away from the finger by the processor of the sample collection and testing device prior to moving the second shaft back and forth one or more times to apply pressure to a side of the finger.

18. The automated method of claim 15, the sample collection and testing device comprising a tube and a pump configured to cause blood to move in or out of the tube, the method further comprising:

by the processor of the sample collection and testing device:

moving the tube to touch the finger at a location in a vicinity of where the lancet pricks the finger; and starting the pump to pull in blood from the finger into the tube.

19. The automated method of claim 18 further comprising: by the processor of the sample collection and testing device:

stopping the pump a period of time after starting the pump; and moving the tube away from the finger.

20. The automated method of claim 18 further comprising: by the processor of the sample collection and testing device:

moving the tube to a receiving device; and starting the pump in a reverse direction to empty the blood from the tube into the receiving device.

* * * * *